(12) United States Patent
Newman et al.

(10) Patent No.: US 11,820,973 B2
(45) Date of Patent: Nov. 21, 2023

(54) METHODS AND SYSTEM FOR INTERFERING WITH VIABILITY OF BACTERIA AND RELATED COMPOUNDS AND COMPOSITIONS

(71) Applicant: CALIFORNIA INSTITUTE OF TECHNOLOGY, Pasadena, CA (US)

(72) Inventors: Dianne K. Newman, Brookline, MA (US); Ryan C. Hunter, Little Canada, MN (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 390 days.

(21) Appl. No.: 16/885,131

(22) Filed: May 27, 2020

(65) Prior Publication Data

US 2020/0362299 A1 Nov. 19, 2020

Related U.S. Application Data

(60) Division of application No. 15/420,022, filed on Jan. 30, 2017, now Pat. No. 10,689,613, which is a continuation of application No. 13/456,172, filed on Apr. 25, 2012, now Pat. No. 9,926,526.

(60) Provisional application No. 61/478,746, filed on Apr. 25, 2011.

(51) Int. Cl.
| | |
|---|---|
| C12N 1/36 | (2006.01) |
| C12N 1/20 | (2006.01) |
| A61K 38/44 | (2006.01) |
| A61K 45/06 | (2006.01) |
| A61P 31/04 | (2006.01) |

(52) U.S. Cl.
CPC ............. *C12N 1/20* (2013.01); *C12N 1/36* (2013.01)

(58) Field of Classification Search
CPC . A61P 11/00; A61P 31/04; C12N 1/36; C12N 1/20
See application file for complete search history.

(56) References Cited

U.S. PATENT DOCUMENTS

| | | |
|---|---|---|
| 10,689,613 B2 | 6/2020 | Newman et al. |
| 10,913,936 B2 | 2/2021 | Newman et al. |
| 2008/0075730 A1 | 3/2008 | Storey et al. |
| 2010/0124554 A1* | 5/2010 | Newman et al. .......... 424/170.1 |
| 2017/0283763 A1 | 10/2017 | Newman et al. |
| 2021/0032603 A1 | 2/2021 | Newman et al. |
| 2022/0175892 A1 | 6/2022 | Newman et al. |

FOREIGN PATENT DOCUMENTS

| | | |
|---|---|---|
| WO | 93/21511 A1 | 10/1993 |
| WO | 2022/099024 A1 | 5/2022 |

OTHER PUBLICATIONS

Liu Y. et al., "Synergistic Activities of an Efflux Pump Inhibitor and Iron Chelators against Pseudomonas aeruginosa Growth and Biofilm Formation", Antimicrobial Agents and Chemotherapy, Sep. 2010, vol. 54, No. 9, pp. 3960-3963. (Year: 2010).*
Yang Z. et al., "Isolation, Identification, and Degradation Characteristics of Phenazine-1-Carboxylic Acid-Degrading Strain *Sphingomonas* sp. DP58", Current Microbiology, 2007, vol. 55, pp. 284-287. (Year: 2007).*
Corrected Notice of Allowance Action for U.S. Appl. No. 15/466,839, filed Mar. 22, 2017, on behalf of California Institute of Technology, dated Sep. 23, 2020. 5 Pages.
EP Decision to grant for EP Application No. 12775958.7 filed on Apr. 25, 2012, dated Feb. 2, 2018. 1 Page.
Final Office Action for U.S. Appl. No. 15/394,138, filed Dec. 29, 2016 on behalf of California Institute of Technology, dated Jul. 2, 2020. 10 Pages.
Gammaproteobacteria, Wikipedia entry retrieved on Mar. 23, 2020 from https://en.wikipedia.org/wiki/Gammaproteobacteria . 3 Pages.
Notice of Allowance for U.S. Appl. No. 15/466,839, filed Mar. 22, 2017 on behalf of California Institute of Technology, dated Sep. 11, 2020. 8 Pages.
Notice of Allowance for U.S. Appl. No. 15/466,839, filed Mar. 22, 2017 on behalf of California Institute of Technology, dated Jun. 4, 2020. 11 Pages.
Pseudomonas, Wikipedia entry retrieved on Mar. 23, 2020 from https://en.wikipedia.org/wiki/Pseudomonas. 12 Pages.
Bellin, D.L., et al., "Electrochemical camera chip for simultaneous imaging of multiple metabolites in biofilms." *Nature communications*, Jan. 27, 2016. 7(1): pp. 1-10 (11 pages).
Blommel, P.G., et al., "Enhanced bacterial protein expression during auto-induction obtained by alteration of lac repressor dosage and medium composition." *Biotechnology Progress*, Published on Web May 17, 2007. 23(3): pp. 585-598 (15 pages).
Cheluvappa, R., "Standardized chemical synthesis of Pseudomonas aeruginosa pyocyanin." *MethodsX*, 2014. 1: p. 67-73 (8 pages).
Cornforth, D.M., et al., "Quantitative framework for model evaluation in microbiology research using Pseudomonas aeruginosa and cystic fibrosis infection as a test case." *MBio*, 2020. 11(1): e03042-19. pp. 1-16 (17 pages).
Galloway, N.R., et al., "Rapid cloning for protein crystallography using type IIS restriction enzymes." *Crystal growth & design*, 2013. 13(7): p. 2833-2839 (8 pages).
Jo, J., et al., "Interdependency of respiratory metabolism and phenazine-associated physiology in Pseudomonas aeruginosa PA14." *Journal of bacteriology*, Feb. 2020. 202(4): pp. 1-18 (19 pages).
Khersonsky, O., et al., "Automated design of efficient and functionally diverse enzyme repertoires." *Molecular cell*, Oct. 4, 2018. 72(1): p. 178-186. e5. (16 pages).
Kragh et al. "Role of Multicellular Aggregates in Biofilm Formation" *mBio, American Society for Microbiology*. Mar. 22, 2016. vol. 7, No. 2. pp. 1-11. (12 pages).

(Continued)

*Primary Examiner* — Satyendra K Singh
(74) *Attorney, Agent, or Firm* — Steinfl + Bruno LLP

(57) ABSTRACT

Provided herein are methods and systems for interfering with viability of bacteria and related compounds and compositions.

17 Claims, 19 Drawing Sheets

Specification includes a Sequence Listing.

(56) References Cited

OTHER PUBLICATIONS

Meirelles, L.A. and D.K. Newman, "Both toxic and beneficial effects of pyocyanin contribute to the lifecycle of Pseudomonas aeruginosa." *Molecular microbiology*, Oct. 23, 2018. 110(6): pp. 995-1010. (17 pages).
Meirelles, L.A., et al., "Bacterial defenses against a natural antibiotic promote collateral resilience to clinical antibiotics." *PLoS biology*, Mar. 10, 2021. 19(3): e3001093. pp. 1-42 (43 pages).
Meylan, S., et al., "Carbon sources tune antibiotic susceptibility in Pseudomonas aeruginosa via tricarboxylic acid cycle control." *Cell chemical biology*, Feb. 16, 2017. 24(2): pp. 195-206. (14 pages).
Miroux, B. et al., "Over-production of proteins in *Escherichia coli*: mutant hosts that allow synthesis of some membrane proteins and globular proteins at high levels." *Journal of molecular biology*, 1996. 260(3): pp. 289-298. (11 pages).
Netzer, R., et al., "Ultrahigh specificity in a network of computationally designed protein interaction pairs." *Nature communications*, 2018. 9(1): pp. 1-13. (14 pages).
Non-Final Office Action for U.S. Appl. No. 15/394,138, filed Dec. 29, 2016, on behalf of California Institute of Technology, dated Sep. 16, 2021. 11 Pages.
O'Toole, G.A., "Microtiter dish biofilm formation assay." *Journal of visualized experiments: JoVE*, 2011(47). pp. 1-2. (3 pages).
Ruddy, J., et al., "Sputum tobramycin concentrations in cystic fibrosis patients with repeated administration of inhaled tobramycin." *Journal of aerosol medicine and pulmonary drug delivery*, 2013. 26(2): pp. 69-75. (8 pages).
Saunders, S.H., et al., "Extracellular DNA promotes efficient extracellular electron transfer by pyocyanin in Pseudomonas aeruginosa biofilms." *Cell*, Aug. 20, 2020. 182(4): pp. 919-932. (35 pages).
Schiessl, K.T., et al., "Phenazine production promotes antibiotic tolerance and metabolic heterogeneity in Pseudomonas aeruginosa biofilms." *Nature communications*, 2019. 10(1): pp. 1-10. (11 pages).
Sezonov, G., D. Joseleau-Petit, and R. d'Ari, "*Escherichia coli* physiology in Luria-Bertani broth." *Journal of bacteriology*, Dec. 2007. 189(23): pp. 8746-8749 (5 pages).
Spero, M.A. and D.K. Newman, "Chlorate specifically targets oxidant-starved, antibiotictolerant populations of Pseudomonas aeruginosa biofilms." *MBio*, Sep. 25, 2018. vol. 9(5): e01400-18. pp. 1-16 (17 pages).
Stewart, P.S., "Diffusion in biofilms." *Journal of bacteriology*, Mar. 2003. 185(5): p. 1485-1491 (8 pages).
Tang, X.X., et al., "Acidic pH increases airway surface liguid viscosity in cystic fibrosis." *The Journal of clinical investigation*, Mar. 2016. Vo. 126(3): pp. 879-891. (15 pages).
Thomsen M.C.F. et al., "Seq2Logo: a method for construction and visualization of amino acid binding motifs and sequence profiles including sequence weighting, pseudo counts and two-sided representation of amino acid enrichment and depletion" *Nucleic acids research*, May 25, 2012. vol. 40(W1): p. W281-W287. (8 pages).
Vandrisse, C. et al., "New high-cloning-efficiency vectors for complementation studies and recombinant protein overproduction in *Escherichia coli* and *Salmonella enterica*." *Plasmid*, 2016. 86: p. 1-6. (10 pages).
Vandrisse C. M. et al., "Computationally designed pyocyanin demethylase acts synergistically with tobramycin to kill recalcitrant Pseudomonas aeruginosa biofilms" *PNAS*, vol. 118 No. 12, Mar. 15, 2021, pp. 1-10. (10 pages).
Walters III, M.C., et al., "Contributions of antibiotic penetration, oxygen limitation, and low metabolic activity to tolerance of Pseudomonas aeruginosa biofilms to ciprofloxacin and tobramycin." *Antimicrobial agents and chemotherapy*, Jan. 2003. vol. 47(1): p. 317-323. (8 pages).
Warszawski, S., et al., "Optimizing antibody affinity and stability by the automated design of the variable light-heavy chain interfaces." *PLoS computational biology*, Aug. 23, 2019. 15(8): p. e1007207. (25 pages).
Zhu, K., et al., "Universal antibiotic tolerance arising from antibiotic-triggered accumulation of pyocyanin in Pseudomonas aeruginosa." *PLoS biology*, Dec. 16, 2019. 17(12): pp. 1-9 e3000573. (9 pages).
Final Office Action for U.S. Appl. No. 15/394,138, filed Dec. 29, 2016, on behalf of California Institute of Technology, dated Mar. 24, 2022. 10 Pages.
International Search Report and Written Opinion for International PCT Application No. PCT/US2021/058275 filed on Nov. 5, 2021, on behalf of California Institute of Technology, dated Mar. 3, 2022. 13 Pages.
Aisen P., Leibman A. 1968; The stability constant of the Fe3+ conalbumin complexes. Biochemical and Biophysical Research Communications 30:407-413.
Danzer, K., "Selectivity and specificity in analytical chemistry. General considerations and attempt of a definition and quantification," *Fresenius J Anal Chem* 369, pp. 397-402. Mar. 2001. https://doi.org/10.1007/s002160000684.
Hedstrom, L., "Enzyme Specificity and Selectivity," In eLS, (Ed.). Feb. 15, 2010. https://doi.org/10.1002/9780470015902.a0000716.pub2.
Restriction Reguirement for U.S. Appl. No. 17/520,345, filed Nov. 5, 2021 on behalf of California Institute of Technology, et al, dated Feb. 6, 2023. 25 pages.
Restriction Reguirement issued by the USPTO for U.S. Appl. No. 17/027,587, dated Jan. 12, 2023, 9 pages.
Advisory Action for U.S. Appl. No. 15/394,138, filed Dec. 29, 2016, on behalf of California Institute of Technology, dated Sep. 22, 2022. 8 Pages.
Alekshun, M.N. "New advances in antibiotic development and discovery." *Expert Opinion on Investigational Drugs* 14(2). 2005. pp. 117-134. 18 Pages.
Angehrn, Peter, et al. "New antibacterial agents derived from the DNA gyrase inhibitor cyclothialidine." Journal of medicinal chemistry 47.6 (2004): 1487-1513.
Chin-A-Woeng, T.F.C. et al., "Introduction of the phzH gene of Pseudomonas chlororaphis PCL1391 extends the range of biocontrol ability of phenazine-1-carboxylic acid-producing *Pseudomonas* spp. Strains", (2001) Mol. Plant-Microbe Interact., vol. 14, No. 8, pp. 1006-1015.
He, Ze, and Michael D. Toney. "Direct detection and kinetic analysis of covalent intermediate formation in the 4-amino-4-deoxychorismate synthase catalyzed reaction." Biochemistry 45.15 (2006): 5019-5028.
Heeb, S., et al. "Regulatory Roles of the GacS/GacA two-component system in plantassociated and other Gram-negative bacteria", MPMI vol. 14, No. 12, 2001, pp. 1351-1363, submitted Jul. 18, 2001 (13 pages).
Levin, Anna S., et al. "Intravenous colistin as therapy for nosocomial infections caused by multidrug-resistant Pseudomonas aeruginosa and Acinetobacter baumannii." Clinical Infectious Diseases 28.5 (1999): 1008-1011.
Mavrodi, D.V. et al., "A Seven-Gene Locus for Synthesis of Phenazine-1-Carboxylic Acid by Psuedomonas fluorescens 2-79", (May 1998), J. Bacteriol., vol. 180, No. 9, pp. 2541-2548.
Maynard, Adam et al. "Antibiotic Kormicin A Kills Bacteria by Producing Reactive Oxygen Species" Journal of Bacteriology, vol. 201, Issue 11, 300718-18, Jun. 2019. pp. 1-11.
Mcdonald, M. et al. "Phenazine Biosynthesis in Pseudomonas fluorescens: Branchpoint from the Primary Shikimate Biosynthetic Pathway and Role of Phenazine-1,6-dicarboxylic Acid", J. Am. Chem. Soc., 2001, 123, 38, pp. 9459-9460.
Merriam-Webster entry for "pathway," as available Apr. 25, 2009, retrieved Oct. 16, 2022 from the WayBackMachine.com (1 page).
Non-Final Office Action issued by the USPTO for U.S. Appl. No. 15/394,138, dated Nov. 10, 2022, 15 pages.
Ohara, Hiroshi, and Toyozo TERASIMA. "Lethal effect of mitomycin-C on cultured mammalian cells." GANN Japanese Journal of Cancer Research 63.3 (1972): 317-327.
Pierson III, L.S. et al., "Molecular analysis of genes encoding phenazine biosynthesis in the biological control bacterium Pseudomonas aureofaciens 30-84", (Dec. 1995) FEMS Microbiol. Lett., vol. 134, Issue 2-3, pp. 299-307.

(56) References Cited

OTHER PUBLICATIONS

Printout from Merriam-Webster for the entry "selecting" as of Apr. 22, 2009. 1 page.
Printout from Merriam-Webster for the entry "selectivity" as of Apr. 22, 2009. 1 page.
Printout from Merriam-Webster for the entry "specificity" as of Apr. 22, 2009. 1 page.
Reimmann, C. et al., "The global activator GacA of Pseudomonas aeruginosa PAO positively controls the production of the autoinducer N-butyryl-homoserine lactone and the formation of the virulence factors pyocyanin, cyanide, and lipase", Molecular Microbiology (1997), 24(2), 309-319.
System—Definition by Merriam-Webster, Dated: Dec. 6, 2010 2 pages.
Vandrisse C. M. et al., "Leveraging the soil-clinic axis for the development of novel microbial therapeutics", Poster. The Weizmann-Caltech Symposium on the Carbon Cycle. Rehovot, Israel, Feb. 2020.
Vessman, J., et al., "Selectivity in analytical chemistry (IUPAC Recommendations 2001)," *Pure and Applied Chemistry*, vol. 73, No. 8, 2001, pp. 1381-1386. 6 Pages. https://doi.org/10.1351/pac200173081381.
Wang, Dongping, et al., "Roles of the Gac-Rsm pathway in the regulation of phenazine biosynthesis in Pseudomonas chlororaphis 30-84", MicrobiologyOpen 2013, 2(3): 505-524.
Wikipedia entry for "Proteobacteria," as published Oct. 25, 2007, retrieved Dec. 31, 2020 from the WayBack Machine, online: //web.archive.org (3 pages).
Wikipedia entry for "Protozoa," as published Nov. 29, 2007, retrieved Dec. 31, 2020 from the WayBackMachine.com (2 pages).
Yaeger, R.G. Excerpts of Medical Microbiology, "Chapter 77 Protozoa: Structure, Classification, Growth, and Development," published 1996 (7 pages).
International Preliminary Report on Patentability for International PCT Application No. PCT/US2021/058275 filed Nov. 5, 2021, on behalf of California Institute of Technology. dated May 19, 2023. 7 Pages.
Merriam-Webster, "demethylate", (Year: 2023). Website: www.merriam-webster.com/dictionary/demethylate, 2023.
Non-Final Office Action for U.S. Appl. No. 15/394,138 filed Dec. 29, 2016 on behalf of California Institute of Technology et al. dated Jun. 16, 2023. 41 pages.
Non-Final Office Action for U.S. Appl. No. 17/027,587, filed Sep. 21, 2020 on behalf of California Institute of Technology. dated May 8, 2023. 31 pages.
Non-Final Office Action for U.S. Appl. No. 17/520,345 filed Nov. 5, 2021 on behalf of California Institute of Technology, et al. dated Jun. 1, 2023. 51 pages.
Notice of Allowance for U.S. Appl. No. 15/394,138 filed Dec. 29, 2016 on behalf of California Institute of Technology et al. dated Apr. 4, 2023. 9 pages.
Notification of Reopening of Prosecution Due to Consideration of an Information Disclosure Statement Filed After Mailing of a Notice of Allowance for U.S. Appl. No. 15/394,138 filed Dec. 29, 2016 on behalf of California Institute of Technology et al. dated May 16, 2023. 4 pages.
Printout of Merriam Webster's definition of "disrupt" 2005 (1 pg). Downloaded through the Wayback Machine.
Struder, R.A. et al. Review Article: Residue mutations and their impact on protein structure and function: detecting beneficial and pathogenic changes. Biochem J. (2013) 449, 581-594.

\* cited by examiner

METHODS AND SYSTEM FOR INTERFERING WITH VIABILITY OF BACTERIA AND RELATED COMPOUNDS AND COMPOSITIONS

CROSS REFERENCE TO RELATED APPLICATIONS

The present application is divisional of U.S. patent application Ser. No. 15/420,022, filed on Jan. 30, 2017, which in turn, is a continuation of U.S. patent application Ser. No. 13/456,172, filed on Apr. 25, 2012, which in turn, claims priority to U.S. Provisional Application No. 61/478,746 filed on Apr. 25, 2011 and entitled "Methods and systems for interfering with viability of Bacteria and Related Compounds and compositions", each of which are incorporated herein by reference in their entirety.

FIELD

The present disclosure relates to methods and systems for interfering with viability of bacteria and related compounds and compositions.

BACKGROUND

Bacteria viability has been the focus of research in the field of biological analysis, in particular when aimed at medical applications such as therapeutic or diagnostic application.

Whether for pathological examination or for fundamental biology studies, several methods are commonly used for the detection and interference with the viability of bacteria.

Although various methods, systems and compositions have been developed to interfere, and in particular, reduce bacterial viability to the extent of killing the bacteria, antibiotic resistance and additional defense mechanisms of the microorganism have made development of methods, systems and compositions able to interfere and in particular inhibit bacterial viability particularly challenging.

SUMMARY

Provided herein, are methods and systems and related compounds and compositions that in several embodiments are suitable for reducing antibiotic resistance and/or survivability of bacteria. In several embodiments, compositions, methods and systems herein described are expected to be suitable to treat and/or prevent bacterial infection in vitro or in vivo.

According to a first aspect, a method and system to interfere with viability of bacteria is described, the method comprising inactivating a phenazine and/or a phenazine related pathway in the bacteria to reduce survivability and/or antibiotic resistance of the bacteria. The system comprises one or more agents able to inactivate a phenazine and/or a phenazine related pathway in the bacteria and an antibiotic and/or other antimicrobial. In some embodiments of the methods and systems, the bacteria comprise persister cells.

According to a second aspect, a method and system to inactivate a bacterium is described. The method comprises contacting the bacterium with an agent capable of inactivating a phenazine and/or a phenazine related pathway in the bacterium in combination with an antibiotic and/or other antimicrobial. The system comprises one or more agents able to inactivate a phenazine and/or a phenazine related pathway in the bacteria and an antibiotic and/or other antimicrobial. In some embodiments of the methods and systems, the bacteria comprise persister cells.

According to a third aspect, a method and system for treating and/or preventing a bacterial infection in an individual is described. The method comprises administering an effective amount of one or more agents able to specifically inactivate a phenazine and/or a phenazine related pathway in the bacteria. In particular, in some embodiments, administering of one or more agents can be performed in combination with one or more antibiotics and/or other antimicrobials. The system comprises one or more agents able to specifically inactivate a phenazine and/or a phenazine related pathway in the bacteria and an antibiotic and/or other antimicrobial. In some embodiments of methods and systems, the bacteria comprise persister cells.

According to a fourth aspect, a method and system for identifying an antimicrobial is described. The method comprises contacting a microbe with a candidate agent and detecting the ability of the candidate agent of inactivating a phenazine and/or a phenazine related pathway in the bacteria. The system comprises one or more microbes and one or more agents capable of detecting phenazine and/or phenazine related pathways. In some embodiments of the methods and systems, the bacteria comprise persister cells.

According to a fifth aspect, an antimicrobial is described. The antimicrobial comprises one or more agents able to inactivate a phenazine and/or a phenazine related pathway in the bacteria. The one or more agents are in particular comprised in the antimicrobial in an amount suitable to reduce antibiotic resistance and/or survivability of bacteria. In some embodiments, the antimicrobial comprises a compatible vehicle, which can be a vehicle for effective administrating and/or delivering of the one or more agents to an individual. In some embodiments of the methods and systems, the bacteria comprise persister cells.

According to a sixth aspect, a method and system to interfere with the viability of bacteria in a medium is described, the method comprises subtracting from the medium Fe(II) alone or in combination with Fe(III) to reduce survivability and/or antibiotic resistance of the bacteria. The system comprises one or more agents capable of subtracting Fe(II) and/or Fe(III) for simultaneous combined or sequential use in the method herein described. In some embodiments, the subtracting is performed by subtracting Fe(II). In other embodiments, the subtracting is performed by subtracting Fe(II) and Fe(III) from the medium.

According to a seventh aspect an antimicrobial is described. The antimicrobial comprises one or more agents able to subtract Fe(II) from a medium suitable to host bacteria. The one or more agents are in particular comprised in the antimicrobial in an amount suitable to reduce antibiotic resistance and/or survivability of bacteria. In some embodiments, the antimicrobial comprises a compatible vehicle, which can be a vehicle for effective administrating and/or delivering of the one or more agents to an individual. In some embodiments of the methods and systems, the bacteria comprise persister cells.

The methods and systems herein described, and related compounds and compositions in several embodiments allow reducing antibiotic resistance and/or bacterial survivability according to distinct mechanism and pathways wherein phenazine functions.

The methods and systems and related compounds and compositions herein described can be used in connection with applications wherein reduction of viability of bacteria and/or reduction of antibiotic resistance is desired, which include but are not limited to medical application, drug research, biological analysis and diagnostics including but not limited to clinical applications.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

DETAILED DESCRIPTION

Figure 1:
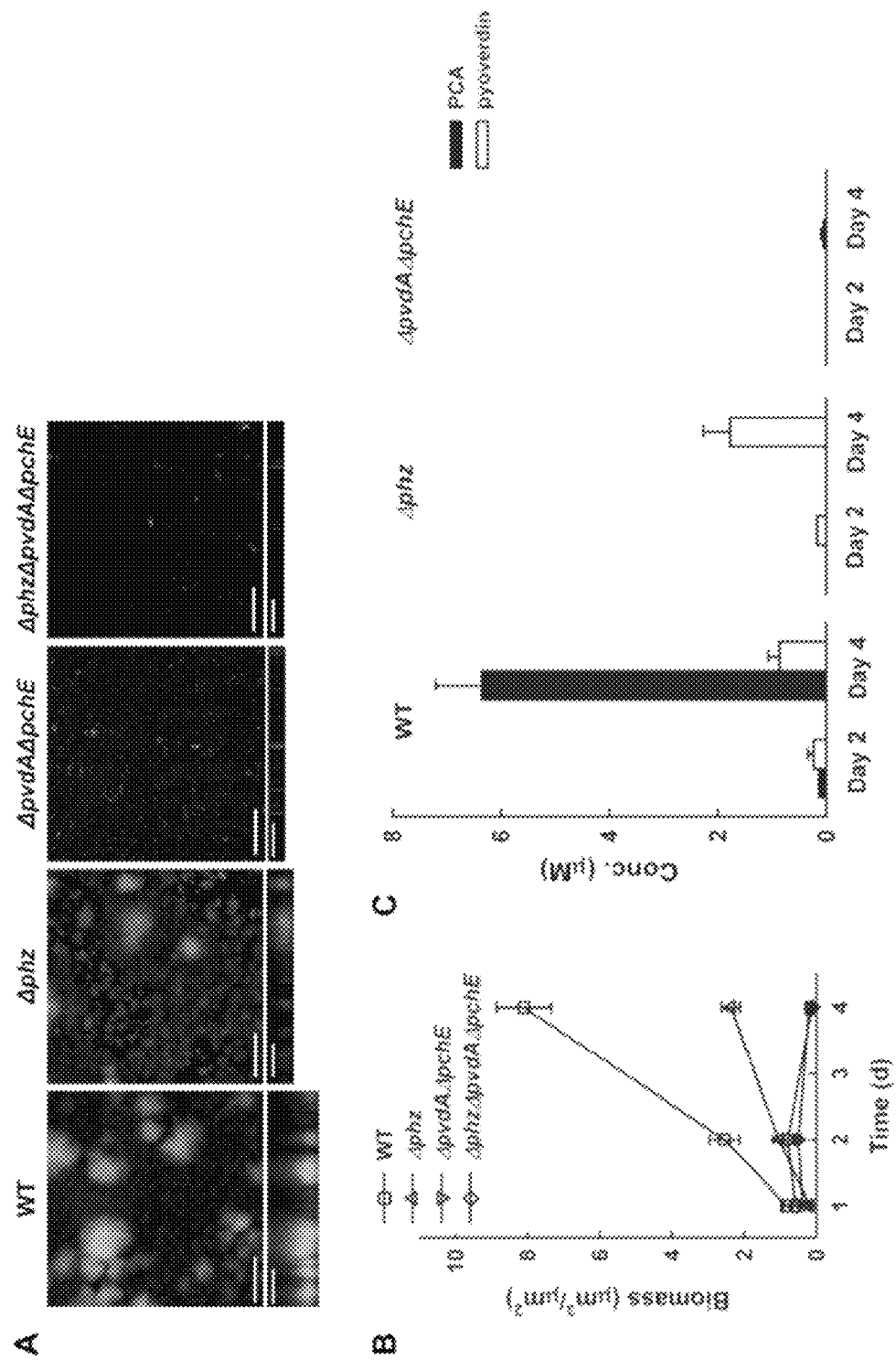
FIG. 1. The phenazine PCA can work together with the siderophore pyoverdin in promoting *P. aeruginosa* biofilm formation. (A) Confocal microscopic images of biofilms at day 4, (B) total biomass over time as inferred by COMSTAT analysis, and (C) the corresponding release of phenazine(s) and/or siderophore(s) into the biofilm effluents for YFP-labeled PA14 wild type (WT), the phenazine null strain (Δphz), the siderophore null strain (ΔpvdAΔpchE), and the phenazine-siderophore null strain (ΔphzΔpvdAΔpchE) under a flow of 1% TSB medium at 22° C. Confocal images consist of top-down views (x-y plane, top images) and side views (x-z plane, bottom images; enlarged and truncated to emphasize differences in the z dimension). Scale bars: 100 μm for top-down view images, 50 μm for side-view images. Results are representative of 6 experiments. Data reported in (B) and (C) represent the mean±SD. Related quantitative data can be found in Table 3.

Provided herein are methods and systems that are based on inactivation of phenazine and/or a phenazine related pathway.

The term "phenazine" as used herein indicates small, colorful, redox-active compounds formed by bacteria to perform diverse physiological functions. Well over 50 phenazines of bacterial origin are known. Among these phenazines, only a few of which have been given trivial names, represent every color of the visible spectrum. The absorption spectra of phenazines are characteristic, with an intense peak in the range 250-290 nm and a weaker peak at 350-400 nm. At least one main band occurs in the visible region (400-600 nm) to which the phenazines owe their colors.

The phenazine pigments are mostly water soluble and are excreted into the medium. For example, pyocyanin produced by *Pseudomonas aeruginosa*, diffuses readily into agar-solidified media which become stained blue. Some phenazines are only sparingly water soluble and precipitate. For examples, chlororaphine, a mixture of phenazine-1-carboxamide (oxychlororaphine) and its dihydro derivative, produced by *Pseudomonas chlororaphis*, accumulate as isolated emerald-green crystals at the base of agar slants. Iodinin crystallizes on the surfaces of old colonies of *Brevibacterium iodinum*, giving them a dark-purple appearance, and phenazine-1-carboxylic acid (PCA) is deposited as golden yellow crystals in colonies of *Pseudomonas aureofaciens* and in the surrounding medium.

Considerable progress has been made in elucidating the biosynthesis as well as properties of individual phenazines. Examples are provided below for two types of phenazines known as pyocyanin and phenazine-1-carboxylic acid, respectively. For more examples of the occurrence, biochemistry and physiology of phenazine production, see Turner et al., 1986, Advances in Microbial Physiology, vol. 27, page 211-275.

Pyocyanin is the phenazine characteristically produced by chromogenic strains of the pseudomonad, which is found as the blue pigment occasionally seen on infected wound dressings. More attention has been paid to pyocyanin than to any other phenazine. Pyocyanin is an organic base, blue in alkaline aqueous solutions but red when acidified. The differential solubility of these forms in chloroform and water was exploited for this pigment. Pyocyanin was found to be chemically reduced to a colorless form and spontaneously reoxidized in air, which has led to the discovery, the indicator and redox properties of the compound. Additionally, pyocyanin slowly decomposed to a yellow substance, no longer basic in nature, now known to be 1-hydroxy-phenazine.

Phenazine-1-carboxylic acid (PCA) is a yellow crystalline compound naturally produced by *P. aureofaciens*. The phenazine produced was readily extracted from acidified cultures with chloroform. Dilute alkali changed the color of the phenazine to orange-red and rendered it insoluble in chloroform. PCA isolated from cultures, in amounts of up to 1 g pigment litre$^{-1}$, was shown to have antibacterial activity towards a number of plant pathogens.

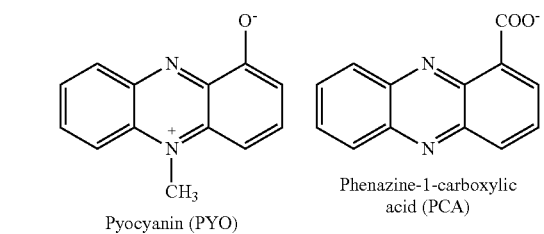

Pyocyanin (PYO)

Phenazine-1-carboxylic acid (PCA)

Phenazines can also include, but are not limited to, molecules according to the structure and formula below:

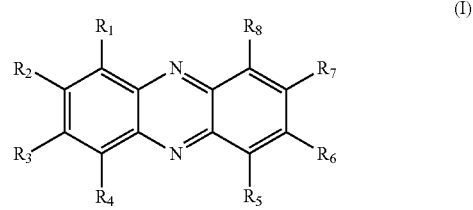

(I)

where $R_3$-$R_8$ are independently selected from hydrogen, hydroxy, alkoxy, alkyl, alkenyl, alkynyl, aryl, heteroaryl, acyl, and other groups identifiable to the skilled person.

Additionally, phenazines can include, but are not limited to, molecules according to the structures and formulas below:

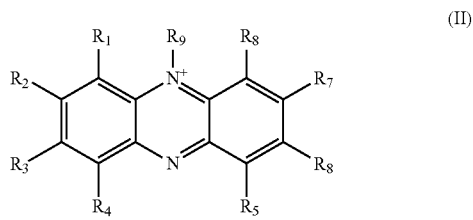

(II)

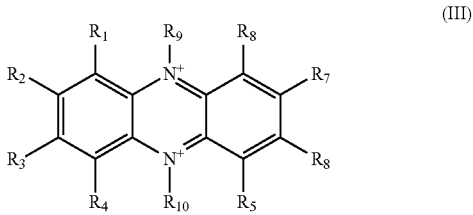

(III)

where $R_1$-$R_{30}$ are independently selected from hydrogen, hydroxy, alkoxy, alkyl, alkenyl, alkynyl, aryl, heteroaryl, acyl, and other groups identifiable to the skilled person, and one of $R_1$-$R_{10}$ is a negatively charged substituent (formal charge of −1) such as —O$^-$.

In particular, exemplary phenazine structures comprise:

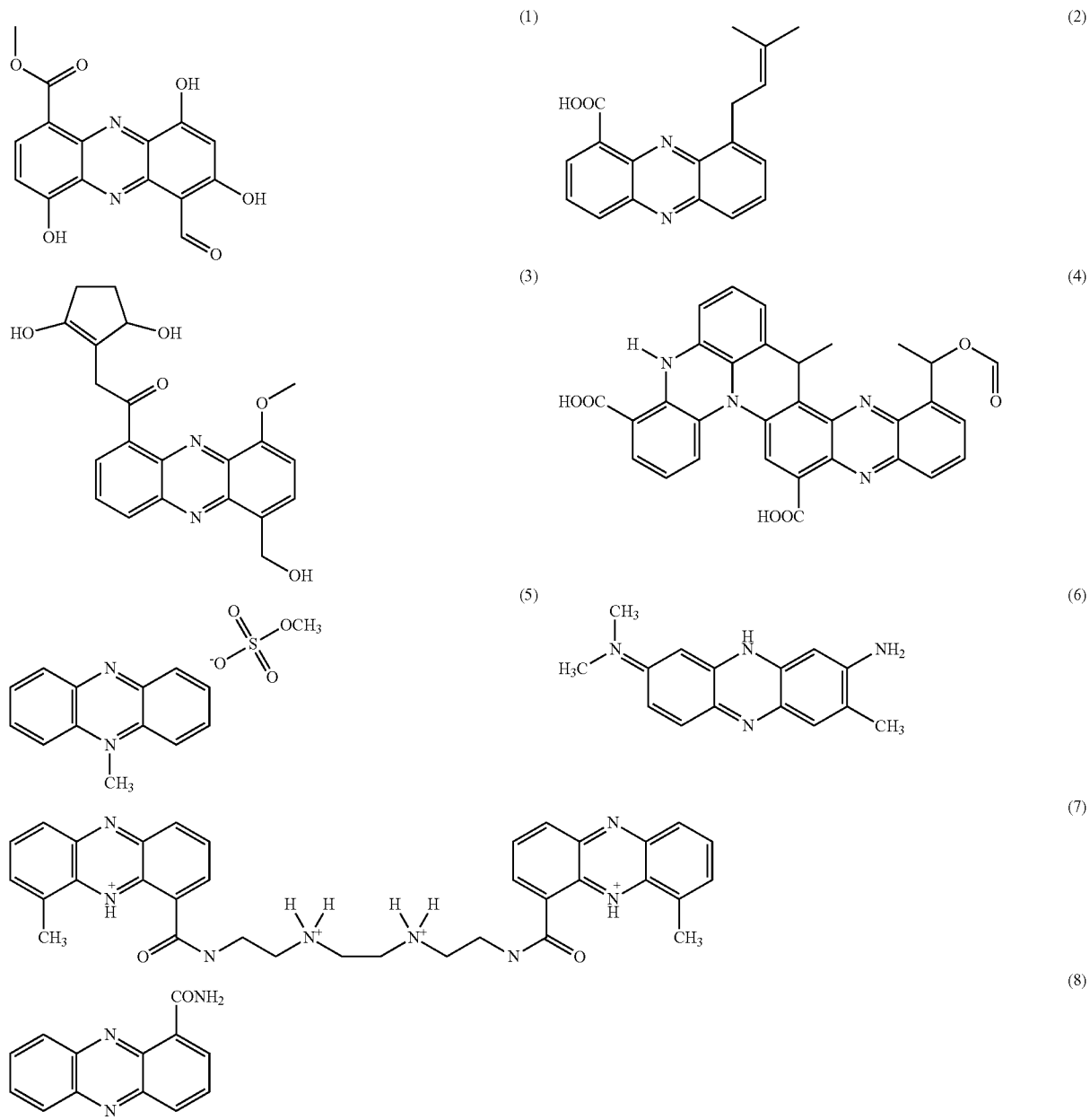

as well as additional phenazines that can be identified by a skilled person such as the exemplary phenazines described in Mentel et al. (ChemBioChem 2009, 10, 2295-2304) and Pierson et al. (Appl Microbiol. Biotechnol. 2010, 86, 1659-1670)

Production of phenazines is of obvious taxonomic value, particularly when relatively few genera are concerned. It should be noted, however, that the same pigment may be produced by unrelated bacteria and "achromogenic" strains of many phenazine-producers are common. Also, a number of strains of bacteria produce more than one phenazine. And it seems likely that all bacterial phenazines are derived from a common precursor.

Recent study has uncovered diverse physiological functions of phenazines for the cells that produce them. For example, the opportunistic pathogen *Pseudomonas aeruginosa* is the dominant pathogen that infects individuals with cystic fibrosis (CF). Production of pyocyanin by *P. aeruginosa* is responsible for the bluish tint of sputum and pus associated with *P. aeruginosa* infections in humans. Clear correlation has been demonstrated between phenazine concentration in sputum and lung function decline. Further, phenazines are found to affect bacterial community development for *P. aeruginosa*.

Several aspects of the disclosure relate, at least in part, to the discovery that phenazines function to promote antibiotic resistance and survivability of bacteria through various distinct mechanisms and pathways and that the related inactivation affect viability of the bacteria.

The term "inactivation" as used herein with reference to a pathway refers to a complete or partial inhibition of one or more of the reactions or steps in the pathway.

The terms "inhibit" and "inhibition" as used herein refers to a decrease relative to a baseline level. Accordingly, inhibition of a reaction indicates a decrease in the relative output compared to an output selected as a baseline level. Inhibition of a reaction can be detected by detecting any products or other indicator and/or parameter associated with completion of the reaction and identifiable by a skilled person. Exemplary inhibition of a reaction can be performed by contacting enzymes catalyzing the reaction with a suitable enzyme inhibitor (i.e. a molecule that decreases the enzyme activity) such that lesser quantities of intermediates and/or products are produced relative to a baseline level. Exemplary inhibition of a step or reaction can also be performed by removal of the relevant substrate and/or intermediate substance (such as, for example, subtraction of Fe(III) and/or Fe(II) in the Fe(III) reduction to Fe(II) and Fe(II) importation pathways), by removing an enzyme involved in the reaction (such as, for example, by suppressing the expression of one of the genes coding for the enzyme), by removing a reducing agent and/or starting material from an oxidation-reduction reaction such that less product is produced, by removing an ion transporter and/or pre-transported ion such that less of the ion is transported into a bacteria, and other approaches and techniques identifiable to a skilled person upon reading of the present disclosure. Accordingly an inactivated pathway in the sense of the present disclosure indicates a pathway in which any enzyme controlling a reaction in the pathway is biologically inactive or in which at least one of the reactions or steps of the pathway is otherwise inhibited, e.g. by deleting one or more genes encoding for enzymes of the pathway and/or by subtracting the relevant substrate and/or intermediate.

The term "pathway" as used herein refers to a biological process comprising one or more chemical or biological reactions or steps in which at least one substance is transformed, produced, and/or acquired by a bacteria. The one or more reactions or steps comprised in the pathway can involve molecules such as, for example, proteins, enzymes, cofactors, oxidizing/reducing agents, signaling molecules, metal ions, and others identifiable to a skilled person upon reading of the present disclosure that participate in the transformation, production and/or acquisition of the substance by a bacteria. In embodiments wherein pathway involves a bacterial cell signaling molecule, the pathway indicates signal transduction through cascade reactions of a series of signaling molecules as part of a complex system of communication that governs basic cellular activities and coordinates cell actions. Exemplary pathways of the disclosure include, but are not limited to, phenazine biosynthesis comprising the steps of synthesizing phenazines from various starting materials (such as, for example, erythrose-4-phosphate, phosphoenol pyruvate, and/or other starting materials) through the use of enzymes (such as, for example, PhzA, PhzB, PhzE, PhzD, and others), Fe(III) reduction to Fe(II) comprising the steps of reduction of Fe(III) to Fe(II) through the use of a reducing agent (such as, for example, phenazine-1-carboxylate, pyocyanin, and/or other reducing agents), bacterial acquisition of Fe(II) comprising the steps of reduction of Fe(III) to Fe(II) by a reducing agent (such as, for example, phenazine-1-carboxylate, pyocyanin, and/or other reducing agents) and importation of Fe(II) into the bacteria by a transporter protein (such as, for example, FeoB), and other pathways identifiable to a skilled person upon reading of the present disclosure.

The term "phenazine-related pathway" as used herein refers to either a pathway in which a phenazine is a starting material, intermediate, or product, or alternatively, any pathway in which at least one of the one or more of the steps comprised in the pathway are mediated by a phenazine. Exemplary pathways in which a phenazine is a starting material, intermediate, or product include, but are not limited to, phenazine biosynthesis, phenazine cycling, quorum sensing, and other pathways identifiable to a skilled person upon reading of the present disclosure. Exemplary pathways in which one or more of the steps of the pathway are promoted or mediated by a phenazine include, but are not limited to, reduction of Fe(III) to Fe(II) by phenazine, bacterial Fe(II) acquisition in which the Fe(II) is obtained, and other processes identifiable to a skilled person upon reading of the present disclosure.

The term "bacteria" as used herein as used herein refers to several prokaryotic microbial species which include but are not limited to Gram-negative and positive bacteria, such as, but not limited to, *Pseudomonas, Brevibacterium, Coryneform Bacteria, Nocardia Brevibacterium linens, Brevibacterium, Burkholderia cenocepecia, Methanosarcina mazei, Mycobacterium abscessus, Pantoea agglomerans, Pectobacterium atrosepticum, Pelagio variabilis, Pseudomonas fluorescens, Streptomyces anulatus, Streptomyces cinnamonensis*, and related species that produce phenazines to facilitate various physiological functions identifiable to a skilled person upon reading of the present disclosure. More specifically, the wording "Gram-negative bacteria" refers to bacteria that do not retain crystal violet dye in the Gram staining protocol. In contrast, the wording "Gram-positive bacteria" refers to are those that are stained dark blue or violet by Gram staining.

In some embodiments, the bacteria comprise persister cells which typically constitute a small portion of a culture which is tolerant to killing by lethal doses of bactericidal antibiotics. Persister bacterial cells can be identified, for example, by exposure of logarithmic or stationary cultures of the bacteria to antibiotics using concentrations exceeding five times the minimum inhibitory concentration for each antibiotic. Persister numbers can be determined by plating the antibiotic-treated cultures on LB agar plates and subsequent counting of colony forming units representing the cell numbers which survived antibiotic exposure. Other methods for identification of persister cells will be known by a skilled person, and can be found, for example, in Möker et al. ("*Pseudomonas aeruginosa* increases formation of multidrug-tolerant persister cells in response to quorum-sensing signaling molecules." In J Bacteriol. 2010 April; 192(7): 1946-55. Epub 2010 Jan. 22).

In some embodiments, phenazine related pathways comprise phenazine-mediated bacterial biofilm formation, phenazine-mediated iron acquisition and phenazine mediated intracellular redox balancing of bacteria (See Example 1-15)

In some embodiments, a phenazine related pathway comprises a phenazine-mediated signaling pathway of the bacteria. Specifically, in some embodiments, the bacteria have a motile and a sessile state and the signaling pathway triggers a transition from the motile to the sessile state (see Examples 6-15).

In some embodiments, one or more phenazine related pathways comprise central metabolic pathways of the bacteria (see Examples 11-15).

In some embodiments, the one or more phenazine related pathways comprise transportation of phenazines in and/or out of the bacterial cell. In other, embodiments, phenazine related pathways comprise intracellular phenazine mediated redox hemostasis of the bacteria.

In some embodiments a method and system to interfere with viability of bacteria is described, the method comprising inactivating a phenazine and/or a phenazine-related pathway in the bacteria to reduce survivability and/or antibiotic resistance of the bacteria.

The term "viability" as used here in refers to whether or not a bacterial cell is able to maintain itself or recover its potentiality. Viable cells in the sense of the present disclosure are cells able to, or capable of recover the ability to, form colonies and biofilms on or in a solid or liquid medium. The term "medium" as used herein indicates an environment that is suitable to support growth of microorganisms or cells. In particular, suitable medium comprise growth medium or culture medium in a liquid or gel designed to support the bacteria in vitro, as well as tissues and other suitable environment within a host (including a human host) in vivo. Methods for evaluating the viability of bacteria after the use of the methods and systems for interference with viability of bacteria described herein include, but are not limited to measurement of colony forming units, cell counts such as that described by Wang et al. (J. Bacteriol. 2010, 192, 365-369), and other methods identifiable to a skilled person upon the reading of the present disclosure.

In some embodiments, inactivation of a phenazine or phenazine-related pathway can be performed by using small interfering RNA (siRNA) techniques to suppress the expression of proteins involved in the pathway.

The term "small interfering RNA (siRNA)" as used herein refers to a class of double stranded RNA molecules, typically of 20-25 nucleotides in length, that play varying roles in biology including suppression of gene expression and are identifiable by a skilled person. Appropriate siRNA sequences can be selected based on the sequence of the gene that is to be suppressed, for example, by use of a sequence designer such as InvivoGen's online siRNA designer (available at the filing date at the www page sirnawizard.com), or by other methods known to a skilled person. The siRNA oligonucleotide sequences can then be introduced into the bacteria, for example, by culturing them with the bacteria of interest to suppress the expression of the gene of interest (as seen, for example, in Yanagihara et al., J. Antimicrob. Chemotherapy 2005, 57, 122-126). Additional methods for interfering with gene expression by RNA interference are identifiable by a skilled person (see, for example, Lehner et al. "How to use RNA interference" Briefings in Functional Genomics and Proteomics, 2004, 3, 68-83) and can include, but are not limited to use of micro RNA (miRNA), small nucleolar RNA (snoRNA), and others identifiable to a skilled person.

In some embodiments, inactivating a phenazine or phenazine-related pathway can be performed by inhibiting synthesis of the phenazine in the bacteria (Example 1). An example of the pathways for phenazine biosynthesis in bacteria is illustrated in Mentel et al. (ChemBioChem 2009, 10, 2295-2304) and reported in the scheme herein below.

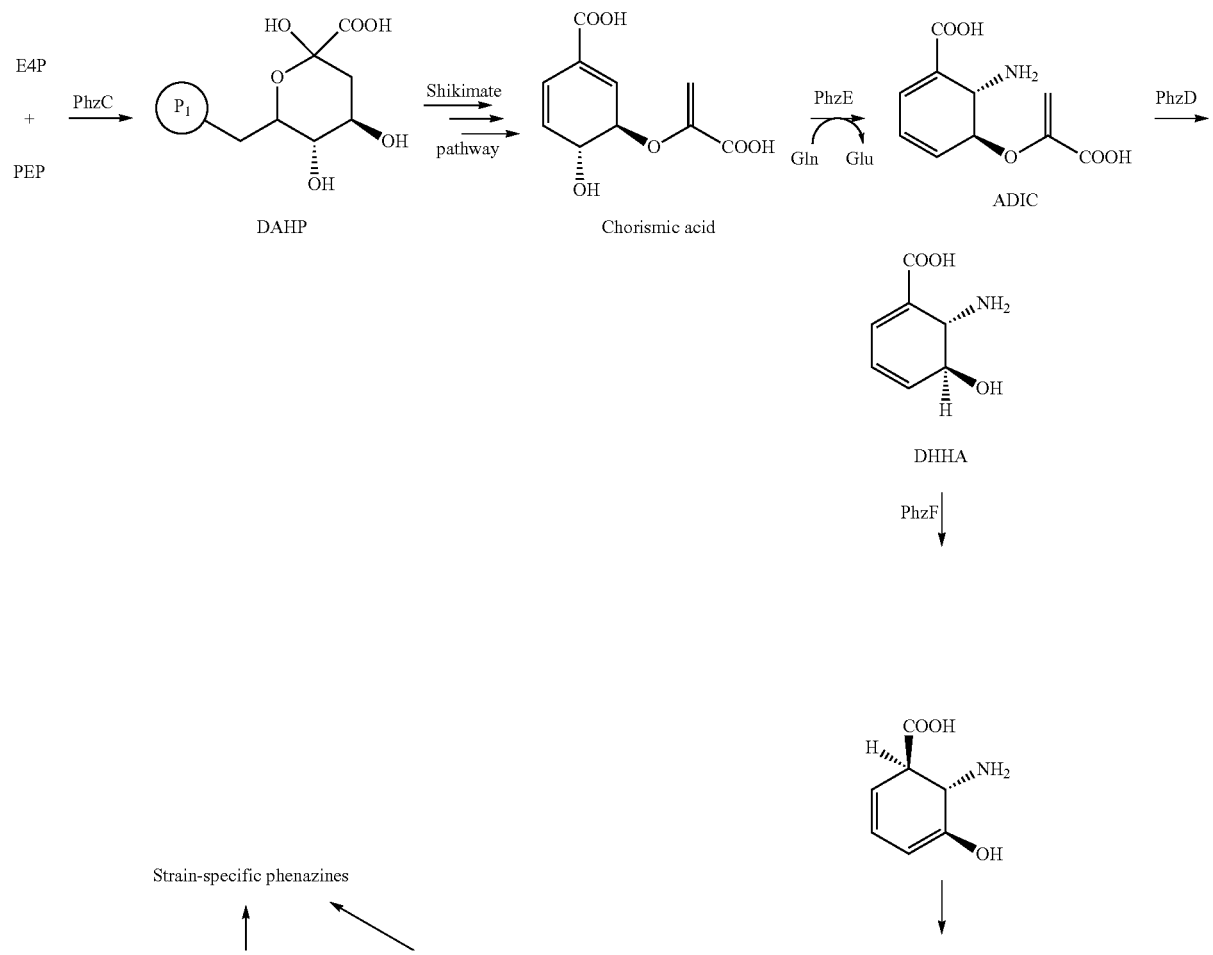

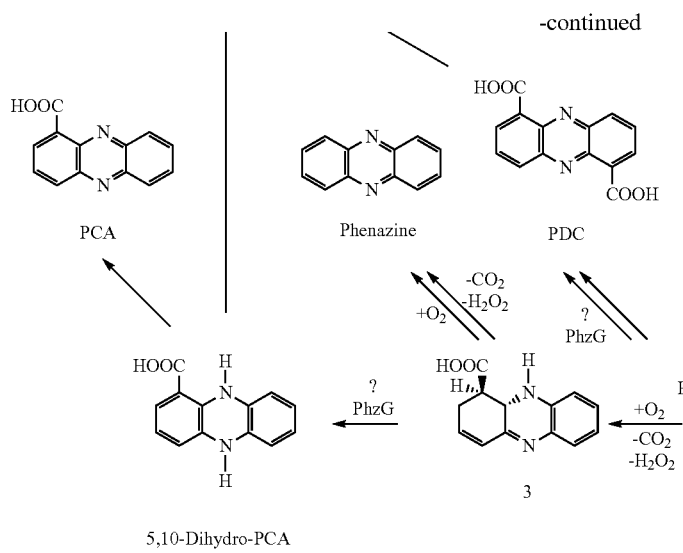
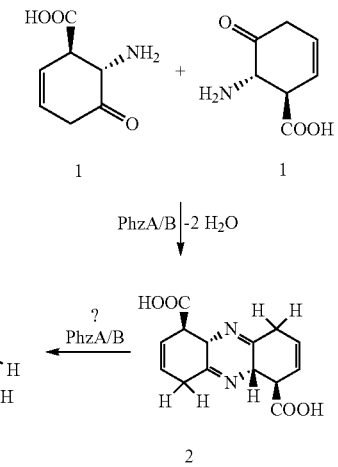

In some embodiments, inhibiting synthesis of a phenazine in the bacteria can be performed by inactivating phenazine biosynthetic genes (see, for example, Example 1), e.g. by blocking transcription and/or blocking translation of said genes. Exemplary phenazine biosynthetic genes include, but are not limited to, genes coding for the phenazine biosynthesis proteins such as PhzA, PhzB, PhzC, PhzD, PhzE, PhzF, PhzF1, PhzF2, PhzG, PhzG1, PhzG2, PhzM, PhzH, PhzS and other proteins and homologs identifiable to a skilled person, such as those indicated in Mentel et al (ChemBioChem 2009, 10, 2295-2304) and Dietrich et al. (Molecular Microbiology 2006, 61, 1308-1321). In some of those embodiments, inactivating can be performed for example by blocking transcription through the siRNA techniques described herein.

In particular, in some embodiments, inhibiting synthesis of the phenazine can be performed by inactivating the relevant biosynthetic pathway, e.g. by inhibiting specific enzymes involved in the synthesis of phenazine from the relevant starting compound (e.g. erythrose-4-phosphate and phosphoenol pyruvate) such as PhzF, an essential diaminopimelate epimerase-like enzyme (Blankenfeldt, PNAS 2004, 101, 16431-16436) which can be inhibited by an aziridino diaminopimelate (see Pillai et al. Proc. Natl, Acad. Sci. 2006, 103, 8668-8673). Other enzymes involved in phenazine biosynthesis that can be inhibited in accordance with the present disclosure and their respective inhibitors are identifiable by a skilled person upon reading of the present disclosure, and include, but not limited to, inhibition of PhzG, a flavin-dependent oxidase (see Parsons et al. Acta Crystallographica Section D, 2004, 60, 2110-2113) by $N^5,N^{10}$-methylene-5,6,7,8-tetrahydrofolate, an inhibitor of the flavin-dependent oxidase FDTS (see Wang et al. FEBS J. 2009, 276, 2801-2810), and inhibition of PhzE by divalent ions such as, but not limited to, $Zn^{2+}$, $Mn^{2+}$, and $Ni^{2+}$ (as seen, for example, in Li et al. J. Biol. Chem. 2011, 286, 18213).

In some embodiments, inactivating a phenazine or phenazine-related pathway is performed by inactivating a phenazine-mediated signaling pathway. In some embodiments, inactivating a phenazine-mediated signaling pathway is performed by inactivating one or more signaling molecules in the phenazine-mediated signaling pathway.

In particular, in some embodiments, the one or more signaling molecules are in the form of a protein. In other embodiments, the signaling molecules are direct or indirect effectors of phenazines in the pathway. Signaling molecule can be identified by a skilled person, and include, but are not limited to, signaling molecules mentioned in Dietrich et al. (Molecular Microbiology 2006, 61, 1308-1321). Specifically, in some embodiments, the one or more signaling molecules comprise acyl homoserine lactones such as, for example 3-oxo-dodecanoyl-homoserine lactone (3-oxo-$C_{12}$-HSL) and butanoylhomoserine lactone ($C_4$—HSL), and quinolones such as, for example, the *pseudomonas* quinolone signal (PQS). (see, for example, Example 17 and Dietrich et al. Molecular Microbiology 2006, 61, 1308-1321).

In some embodiments, inactivating one or more signaling molecules is performed by inhibiting expression of one or more genes in the bacteria coding for signaling molecules in the pathway. In an exemplary embodiment, the gene suppressed is the pqsH gene, which codes for the protein PqsH that synthesizes PQS, and it is suppressed as described above by using the siRNA techniques herein described (see, for example, Example 17 and Dietrich et al. Molecular Microbiology 2006, 61, 1308-1321).

In particular, in some embodiments, inactivating a phenazine or phenazine-related pathway can be performed by inactivating one or more proteins that recognize signaling molecules. In some of those embodiments, the one or more proteins comprise proteins that recognize acyl homoserine lactones such as 3-oxo-$C_{12}$-HSL and $C_4$—HSL. Examples of proteins that recognize acyl homoserine lactones include, but are not limited to, LasR and RhlR. In an exemplary embodiment, LasR and RhlR are inactivated by suppressing the genes lasR and rhlR using the siRNA techniques herein described. Additional methods of inactivating the proteins such as LasR, RhlR, and PhzAl-G1 can be identified by a skilled person upon reading of the present disclosure (see, for example, Example 17 and Dietrich et al. Molecular Microbiology 2006, 61, 1308-1321).

Additional signaling molecules suitable in the methods and systems herein described, are identifiable by a person skilled in the art upon reading of the present disclosure. In an exemplary embodiment, identification of signaling molecule can be performed by generating mutant bacterial strains with defective phenazine biosynthetic pathways, for example, by transposing the relevant DNA sequences and identifying from the gene sequences the related proteins involved in phenazine biosynthesis e.g. by using the techniques of Gallagher et al. (J. Bacteriol. 2002, 184, 6472-6480; incorporated herein by reference in its entirety).

In some embodiments, inactivating a phenazine or phenazine-related pathway can be performed by interfering with quorum sensing of bacteria and in particular with the proteins and other molecules involved in the related pathway, which is more particularly associated with phenazine biosynthesis (see Example 17).

Figure 19:
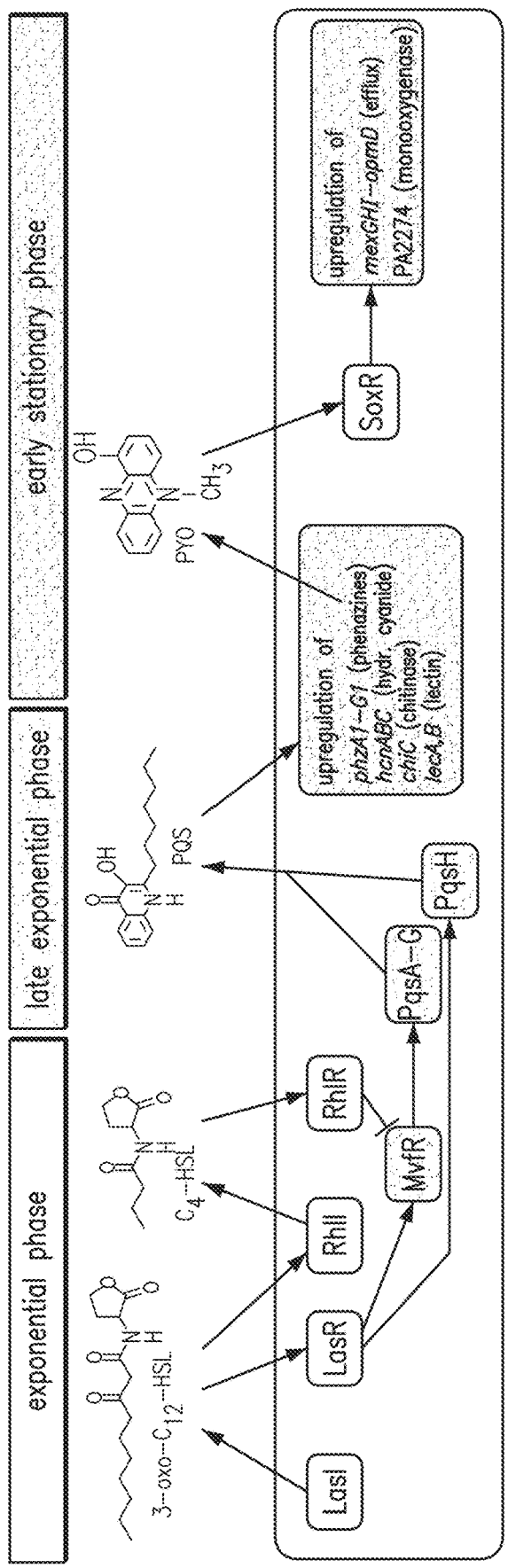
FIG. 19: Schematic illustration of a Model of the QS network in *P. aeruginosa* PA14. The PA14 QS from Dietrich et al. (Molecular Microbiology 2006, 61, 1308-1321)

The term "quorum sensing" as used herein refers to a system of stimulus and response correlated to bacterial population density typical of certain bacteria identifiable by a skilled person. Bacteria having quorum sensing, use quorum sensing to coordinate gene expression according to the density of their local population. Bacteria that use quorum sensing constantly produce and secrete certain signaling molecules (called autoinducers or pheromones). These bacteria also have a receptor that can specifically detect the signaling molecule (inducer). When the inducer binds the receptor, it activates transcription of certain genes, including those for inducer synthesis. There is a low likelihood of a bacterium detecting its own secreted inducer. Thus, in order for gene transcription to be activated, the cell must encounter signaling molecules secreted by other cells in its environment. When only a few other bacteria of the same kind are in the vicinity, diffusion reduces the concentration of the inducer in the surrounding medium to almost zero, so the bacteria produce little inducer. However, as the population grows, the concentration of the inducer passes a threshold, causing more inducer to be synthesized. This forms a positive feedback loop, and the receptor becomes fully activated. Activation of the receptor induces the upregulation of other specific genes, causing all of the cells to begin transcription at approximately the same time. A model of a bacterial quorum sensing network and its association with phenazine synthesis can be seen, for example, in Dietrich et al. (Molecular Microbiology 2006, 61, 1308-1321) and is illustrated in FIG. 19.

In some embodiments, interfering with the quorum sensing of the bacteria can be performed by inhibiting transcription and/or translation of the phenazine biosynthetic genes. In an exemplary embodiment, interfering with quorum sensing can be performed using siRNA oligonucleotides corresponding to the gene sequences of pqsH (as seen, for example, in Gallagher et al. J. Bacteriol. 2002, 184, 6472-6480). In particular, in some embodiments siRNA oligonucleotides corresponding to the gene sequences of pqsH can be added to the bacteria and be incorporated into the bacteria using methods and techniques identifiable by a skilled person upon reading of the present disclosure. In some embodiments, the siRNA oligonucleotides can then interfere with the expression of pqsH which in turn can result in the inhibited biosynthesis of *Pseudomonas* quinolone signal (PQS) and subsequently results in reduced phenazine biosynthesis as seen, for example, in Dietrich et al. (Molecular Microbiology 2006, 61, 1308-1321). Additional genes to target by siRNA methods described herein include, but are not limited to, other genes that code for proteins involved in quorum sensing such as, but not limited to, LasR, RhlI, RhlR, MvfR and others, as indicated in, for example, Dietrich et al. (Molecular Microbiology 2006, 61, 1308-1321) (see, for example, Example 17).

In another exemplary embodiment, bacterial strains can be grown in the presence of quorum-sensing inhibitors such as, tobramycin (see, for example, Babic "Tobramycin at subinhibitory concentration inhibits the RhlI/R quorum sensing system in a *Pseudomonas aeruginosa* environmental isolate" Infectious Diseases 2010, 10:148 and Garske et al. Pathology 2004, 36, 571-575) or furanone C-30 (Hentzer et al. EMBO J. 2003 Aug. 1; 22(15): 3803-3815), or others identifiable to a skilled person.

In some embodiments, inactivating a phenazine related pathway can be performed by inactivating intracellular phenazine mediated redox hemostasis of the bacteria is performed by inhibiting phenazine-mediated electron shuttling of the bacteria. In a non-limiting example, the phenazine-mediated electron shuttling of the bacteria is inhibited by inhibiting the biosynthesis of phenazines as described above. (See Examples 6-15).

In some embodiments, inactivating a phenazine or phenazine related pathway can be performed by reducing the amount of phenazine in bacteria, e.g. by any of techniques and approaches herein described performed to reduce rather than minimize the amount of phenazine synthesized by bacteria (see, for example, Example 1). The amount of phenazine in the bacteria before and after reduction of the quantity of phenazine according to the methods described herein can be measured by methods identifiable to a skilled person upon reading of the present disclosure. For example, the quantity of phenazine in bacterial culture before and after reduction of the quantity of phenazine can be measured by directly loading the filtrate of the culture onto a HPLC column and analyzing the filtrate as done by Dietrich et al. (Molecular Microbiology 2006, 61, 1308-1321). Additional quantification techniques can be identified by a skilled person and can include, for example, using time-lapsed spectral multiphoton fluorescence microscopy of Sullivan et al., (ACS Chemical Biology 2011, 6, 893-899) to monitor phenazine concentrations within bacterial cells in vivo both before and after reduction of the phenazine levels.

In some embodiments, reducing the amount of phenazine in bacteria can be performed by enhancing phenazine degradation endogenously and/or exogenously.

In particular, in some embodiments, enhancing phenazine degradation can be performed by expressing and/or delivering a protein that degrades phenazines. In an exemplary embodiment, a DNA sequence of a phenazine-degrading protein can be delivered by introduction of the DNA sequence into a bacterium via a vector (e.g. viral vector), or other techniques identifiable by a skilled person upon reading of the present disclosure, and the DNA sequence expressed in the bacteria to produce the phenazine-degrading protein. In another embodiment, phenazine-degrading proteins can be expressed in other bacteria and then isolated and purified to afford phenazine-degrading proteins suitable for extracellular degradation of phenazine (see for example, Examples 15 and 18).

In some embodiments, inactivating a phenazine or phenazine-related pathway is performed by providing the bacteria with one or more phenazine-degrading enzymes. Bacteria that degrade phenazines have been isolated and identified (see Examples 15 and 18).

In some embodiments, enzymes degrading a phenazine can be identified by first identifying a bacterium capable of phenazine degradation. The identification can be performed, for example, by constructing a bacterial "enrichment culture" by defining a minimal growth medium where a phenazine (PCA, PYO, and additional phenazines identifiable by a skilled person) is provided as either (or both) the sole source of carbon or nitrogen. If growth is observed after many rounds of serial dilutions, phenazine-degraders can be isolated by plating the enrichment culture on an agar plate with the same medium composition. Single colonies are picked, and streaked to fresh plates, and visually checked for purity. Once pure, the 16S rDNA is sequenced and the organism can be phenotypically characterized. Other methods for identifying a bacterium capable of phenazine degradation would be identifiable to a skilled person upon reading of the present disclosure. Once a bacterium capable of degrading phenazine is identified, one or more particular enzymes responsible for phenazine degradation in the bacterium can be identified, for example, by biochemical approach and/or genetic approaches (see, for example, Examples 15 and 18).

In an exemplary embodiment, the bacteria capable of producing phenazine-degrading enzymes are *Sphingomonas* sp. DP58 (see Yang et al. Current Microbiology 2007, 55, 284-287 and Chen et al. Biodegradation 2008, 19, 659-667).

In particular, a biochemical approach can comprise performing an activity assay, for example based on absorption or fluorescence a phenazine over time and a subsequent purifying of cell fractions to promote a disappearance of phenazine.

A genetic approach can comprise employing transposition mutagenesis to make a collection of random mutants and screening them for an inability to grow on a minimal medium plus the phenazine, as described, for example, in Gallagher et al. (J. Bacteriol. 2002, 184, 6472-6480).

Further to these methods, once an enzyme is identified, the specificity of the enzyme can be altered using directed evolution, such that following directed evolution the enzyme can recognize either a specific phenazine, a broader range of phenazines, and/or to improve efficiency of the enzyme. In an exemplary embodiment, the genetic sequence corresponding to the phenazine degrading enzyme can be randomly mutated using error-prone PCR or another technique identifiable to the skilled person to produce a library of mutated genetic sequences. The proteins expressed by the mutant sequences can be screen for phenazine degrading activity against specific or broad ranges of phenazines, for example, by the spectrophotometric measurement of phenazine levels over time. The proteins thus identified to be able to degrade a specific phenazine or broad range of phenazines can be synthesized, for example, in a bacterium using recombinant DNA techniques known to the skilled person (see, for example, Examples 15 and 18).

In other embodiments, reducing the amount of phenazine in bacteria is performed by modifying the phenazines (e.g. chemically) to interfere and in particular minimize phenazine uptake by the bacteria. Exemplary modifications include, but are not limited to, direct chemical modification of the phenazines such as, epoxidation of reactive double bonds, alkylation of nucleophilic groups, acylation of nucleophilic groups, electrophilic aromatic substitution of one or more hydrogen atoms on the phenazines, and other chemical modifications identifiable to a skilled person using reaction conditions identifiable to a skilled person.

In some embodiments, inactivating a phenazine or phenazine related pathway is performed by inhibiting transportation of phenazines in and/or out of a bacterial cell. In particular, in some embodiments, inhibiting transportation of phenazines in and/or out of a bacterial cell can be performed by blocking one or more phenazine exporters of bacteria. Suitable bacterial phenazine exporter inhibitors include, but are not limited to, Phe-Arg-β-naphthylamide (PAβN), Pro-D-hPhe-3-aminoquinolone (MC-04,124), and MexAB-OprM-specific EPI D13-9001, and others identifiable to a skilled person upon reading of the present disclosure (additional inhibitors can be found, for example, in Hirakata et al., 2009, Int. J. Antimicrob. Agents, 34:343-346, and Askoura, Libyan J Med, 2011, 6, 5870). In an exemplary embodiment, bacteria can be inoculated onto an agar plate into which has been incorporated a phenazine exporter inhibitor such as done, for example, by Saenz et al. (J. Antimicrob. Chemotherapy 2004, 544) and the efficacy of inhibition determined, for example, by the method of Fritsche et al (Antimicrobial Agents and Chemotherapy, 2005, 49, 1468-1476).

In some embodiments, the one or more phenazine exporters of bacteria comprise RND efflux pumps of the mexGHI-opmD variety. (see Example 17). In an exemplary embodiment, the activity of the efflux pump mexGHI-opmD can be inhibited by, for example, preventing its expression with appropriate siRNA oligonucleotides as described above.

In some embodiments, the bacterium is *Pseudomonas aeruginosa*, and the one or more phenazine export proteins of bacteria can be encoded by genes PA4205, PA4206, PA4207 and/or PA4208, and the phenazine exportation is disrupted by deleting of these genes or by decreasing their expression. In an exemplary embodiment, gene sequences can be deleted by generating the appropriate integration cassette connected to the upstream and downstream regions flanking the genes to be deleted and transforming the generated recombinant DNA into the bacterial genome, for example, in a liquid culture, as done for example by Berardinis et al. ("A complete collection of single-gene deletion mutants of *Acinetobacter baylyi* ADP1" Molecular Systems Biology 2008 4: 174) and Dietrich et al. (Molecular Microbiology 2006, 61, 1308-1321). (See, for example, Example 1)

In some embodiments, inhibiting transportation of phenazines in and/or out of a bacterial cell is performed by blocking a protein involved in modifying phenazines to be recognized by a phenazine exporter of bacteria (see Example 17). Proteins involved in modifying phenazines to be recognized by a phenazine exporter include, but are not limited to, the phenazine-decorating PhzM, PhzS, and PhzH indicated by Dietrich et al. (Molecular Microbiology 2006, 61, 1308-1321). These proteins, while required for addition of functional groups, are not required for protein export. Methods for blocking these proteins include, but are not limited to, the use of inhibitors as with PhzF above, and the use of siRNA oligonucleotides to suppress their expression as described above.

In some embodiments, the bacterium is *Pseudomonas aeruginosa*, and the phenazine related pathway is redox sensing of bacteria and the protein involved is the protein encoded by gene PA2274 (see Example 17). The expression of such a gene can be suppressed by use of the siRNA oligonucleotides as described above. Alternatively, as the coded enzyme is a flavin-dependent monooxygenase, it is expected to be inhibited by $N^5,N^{10}$-methylene-5,6,7,8-tetrahydrofolate in substantially the same manner as PhzG above.

In some embodiments, inhibiting transportation of phenazines in and/or out of a bacterial cell can be performed by blocking one or more MFS transporters involved in phenazine import/export of bacteria herein described.

In some embodiments, the bacterium is *Pseudomonas aeruginosa*, and the one or more MFS transporters involved in phenazine import/export of bacteria can be encoded by the genes PA3718 and/or PA4233. In an exemplary embodiment, the MFS transporters encoded by genes PA3718 and/or PA4233 can be blocked by suppression of their expression by their genes using the siRNA techniques described herein. In an alternative, non-limiting example, the MFS transporters can be blocked using the inhibitor Phe-Arg-β-naphthylamide and the methods of Saenz et al. (J. Antimicrob. Chemotherapy 2004, 544) and Fritsche et al. (Antimicrobial Agents and Chemotherapy, 2005, 49, 1468-1476). Additional inhibitor would be identifiable to a skilled person and can include, for example, inhibitors described by Vecchione et al. (Antimicrob. Agents and Chemotherapy, 2009, 53, 4673-4677) (see, for example, Example 1 and Dietrich et al. Molecular Microbiology 2006, 61, 1308-1321).

In some embodiments, inactivating a phenazine or phenazine related pathway is performed by converting at least a portion of the phenazine of the bacteria to an inactive form. Specifically, in some embodiments, converting at least a portion of the phenazine to an inactive form is performed by inhibiting intracellular reduction and/or extracellular oxidation of phenazines of the bacteria. In an exemplary embodiment, inhibition of intracellular reduction of phenazines can be performed by growing bacterial cultures in a bacterial growth medium, for example, containing compounds with structures analogous to phenazines capable of inhibiting the intracellular reduction of phenazines including, but not limited to, methylene blue, paraquat, and others identifiable to a skilled person. In another exemplary embodiment, extracellular oxidation of phenazine can be inhibited by removing a oxidant, such as Fe(III), (see, for example, Hernandez et al. Applied and Environmental Microbiology 2004, 70, 921-928) by growing bacterial cultures in a bacterial growth medium containing an Fe(III) chelator such as, for example, conalbumin as indicated, for example, by Wang et al. (J. Bacteriol. 2011, 193, 3606-3617). Additional methods of inhibiting intracellular reduction and/or extracellular oxidation of phenazines of the bacteria will be identifiable to a skilled person upon reading of the present disclosure.

Therefore, inactivating phenazines can be performed in some embodiments, by interfering with phenazine uptake and/or intracellular processing of the bacteria (see Example 14). Thus, in some embodiments, converting at least a portion of the phenazine to an inactive form can be performed by modifying phenazines (e.g. chemically) to interfere with phenazine uptake and/or intracellular processing of bacteria.

In some embodiments, inactivating a phenazine or phenazine-related pathway comprises impairing phenazine-mediated bacterial biofilm development in the bacteria.

As used herein the term "biofilm" indicates an aggregate of microorganisms in which cells adhere to each other on a surface. These adherent cells are frequently embedded within a self-produced matrix of extracellular polymeric substance (EPS). Biofilms can form on living or non-living surfaces and can be prevalent in natural, industrial and hospital settings. The microbial cells growing in a biofilm are physiologically distinct from planktonic cells of the same organism, which, by contrast, are single-cells that can float or swim in a liquid medium. Formation of a biofilm begins with the attachment of free-floating microorganisms to a surface. These first colonists adhere to the surface initially through weak, reversible adhesion via van der Waals forces. If the colonists are not immediately separated from the surface, they can anchor themselves more permanently using cell adhesion structures such as pili. When the biofilm growth is balanced with that of biofilm dispersion, the biofilm is considered "mature." Methods to quantify and measure biofilms will be known to a skilled person and can include, for example, the COMSTAT method of Heydorn et al. (Microbiology 2000, 146, 2395-2407).

In some embodiments, the phenazine-mediated bacterial biofilm development comprises phenazine-mediated iron acquisition of bacteria. Iron has been shown to be involved as a signal in bacterial biofilm formation (see, for example, Banin et al. PNAS, 2005, 102, 11076-11081). Phenazines have been shown to mediate iron acquisition in bacterial biofilm development, for example, by reduction of insoluble Fe(III) to more soluble Fe(II) (See, for example, Wang et al. J. Bacteriol. 2011, 193, 3606-3617, and Examples 1-6).

In some embodiments, inactivating a phenazine related pathway comprises inactivating phenazine-mediated iron acquisition of bacteria. In an exemplary embodiment, the inactivation of the phenazine-mediated iron acquisition is performed by reducing the amount of phenazine in bacteria, e.g. by any of techniques and approaches herein described to reduce the amount of phenazine available to reduce Fe(III) to Fe(II) prior to acquisition by the bacteria (see, for example, Examples 1-6).

In other embodiments, the inactivation of the phenazine-mediated iron acquisition is performed by subtracting iron from the medium hosting the bacteria.

The term "subtraction" as used herein with reference to iron refers to the at least partial removal of iron in any of its oxidation states from a bacteria or its local environment such that the subtracted iron is not able to be acquired or otherwise used by the bacteria. Exemplary iron subtraction can be performed by ion exchange, precipitation of the iron, sequestration of the iron, and other approaches and techniques identifiable to the skilled person upon reading of the present disclosure.

In some embodiments, the subtracting is performed by use of iron chelators. The term "chelator" as used herein refers to a molecule capable of binding a metal ion (e.g. iron) by forming multiple bonds to the metal. Chelators can be biological molecules (such as, hemoglobin, transferrin, lactoferrin, conalbumin and ferritin; or siderophores such as deferoxamine, deferiprone, deferasirox, 2,2-dipyridyl, 1,10-phenanthroline, Ferrozine® and Enterobactin; or others identifiable to a skilled person) or organic chelators (such as EDTA, diethylenetriamine, ethylenediamine, N,N',N"-tris (2-pyridylmethyl)-1,3,5-cis,cis-triaminocyclohexane (tachpyr), and others identifiable to a skilled person).

In other embodiments, inactivating the pathway of phenazine-mediated iron acquisition by bacteria is performed by inhibiting Fe(II) acquisition by bacteria. In particular, in some embodiments, inhibiting Fe(II) acquisition by bacteria can be performed by inhibiting cytoplasmic membrane Fe(II) transporter of bacteria. In some embodiments, the Fe(II) transporter is the cytoplasmic membrane protein FeoB or a homologues protein thereof identifiable to a skilled person (such as, but not limited to, FeoB1 and FeoB2; see, for example, Dasper et al. The Journal of Biological Chemistry 2005, 280, 28095-28102, and Example 3 below). Other suitable cytoplasmic membrane Fe(II) transporters can be identified by a skilled person, and can include those in bacteria which substantially do not grow anaerobically on Fe(II). In an exemplary embodiment, the inhibition of FeoB can be performed by suppressing FeoB expression using the siRNA techniques described above. In an additional non-limiting example, due to FeoB being a transporter of divalent iron, FeoB can be inhibited by inhibitors of other divalent metal transporters such as, but not limited to, NSC306711 and NSC75600 and others identifiable to a skilled person (see, for example, Buckett et al. Am. J. Physiol. Gastrointest. Liver Physiol. 2009, 296, G798-G804).

In other embodiments, inactivating the pathway of phenazine-mediated iron acquisition can be performed by exposing bacteria to an Fe(II) chelator. Specifically, in some embodiments, the Fe(II) chelator is in the form of a protein and/or a chemical compound. In an embodiment, the activation of the Fe(II) chelator can be performed by adding the Fe(II) chelator to a bacterial culture in a way similar to the use of conalbumin to chelate Fe(III) described herein (see, for example, Example 3).

In some embodiments, the Fe(II) chelator is Ferrozine®, and activating of the Fe(II) chelator can be performed by delivering Ferrozine® into, for example, the mucus environment of bacteria (see, for example, Examples 21-22).

In some embodiments the Fe(II) chelator is in the form of an aerosol and can thus be delivered topically, e.g. directly into the lungs of a patient. Methods to deliver the Fe(II) chelator into the lungs of a patient can be identified by a skilled person using, for example, the methods of Corkery ("Inhalable Drugs for Systemic Therapy" Respiratory Care 2000, 45, 931-835) (see, for example, Examples 19-20).

In other embodiments, the Fe(II) chelator is a host protein, and activating a Fe(II) chelator comprises regulating of one or more host genes encoding a host Fe(II) chelator. Fe(II) chelating host proteins are identifiable to a skilled person can include, but not be limited to, apoferritin and methods for regulating the host genes encoding the host Fe(II) chelators can be identified by a skilled person and can include, but not be limited to, use of the siRNA techniques described above.

In some embodiments, inactivating the pathway of phenazine-mediated iron acquisition of bacteria can be performed by inhibiting phenazine-mediated Fe (III) reduction to Fe(II) (see, for example, Examples 1-4). In an exemplary embodiment, the phenazine-mediated Fe(III) reduction to Fe(II) can be inhibited by reducing amount of Fe(III) available to a bacterial culture by a suitable addition of iron chelator such as conalbumin, to the bacterial culture. As seen in Example 3 and, for example, and in Wang et al. (J. Bacteriol. 2011, 193, 3606-3617) the biofilm development was impaired when in presence of conalbumin. Other iron-binding molecules usable in this method would be identifiable to skilled person and can include, for example, EDTA, desferrioxamine, hemoglobin, transferrin, lactoferrin, and ferritin.

In some embodiments, inactivating the pathway of phenazine-mediated iron acquisition can be performed by activating a Fe(III) chelator in the bacteria. Specifically, in some embodiments, the Fe(III) chelator is in the form of a protein and/or a chemical compound (see Examples 19-22). In exemplary embodiment, the activation of the Fe(III) chelator can be performed by adding the Fe(III) chelator to a bacterial culture the in a way similar to the use of conalbumin to chelate Fe(III) to inhibit its reduction to Fe(II) described above in reference to Example 3 below. In another non-limiting example, a DNA sequence of a Fe(III) chelating protein delivered by introduction of the DNA sequence into a bacteria via a virus, or another technique identifiable to a skilled person upon reading of the present disclosure, and the DNA sequence expressed in the bacteria to produce the Fe(III) chelating protein. Appropriate Fe(III) chelating proteins can include, but are not limited to, hemoglobin, transferrin, lactoferrin, and ferritin.

In some embodiments, the Fe(III) chelator is conalbumin, and activating a Fe(III) chelator can be performed by delivering conalbumin into the mucus environment of bacteria (see, for example, Examples 3 and 21-22).

In some embodiments the Fe(III) chelator is in the form of an aerosol and can thus be delivered directly into the lungs of a patient. Methods to deliver the Fe(III) chelator into the lungs of a patient can be identified by a skilled person using, for example, the methods of Corkery ("Inhalable Drugs for Systemic Therapy" Respiratory Care 2000, 45, 931-835) (see, for example, Examples 19-20).

In other embodiments, the Fe(III) chelator is a host protein, and activating a Fe (III) chelator comprises regulating of one or more host genes encoding a host Fe(III) chelator. Fe(III) chelating host proteins are identifiable to a skilled person can include, but not be limited to, hemoglobin, transferrin, lactoferrin, conalbumin, and ferritin, and methods for regulating the host genes encoding the host Fe(III) chelators can be identified by a skilled person and can include, but not be limited to, use of the siRNA techniques described above (see, for example, Example 3 and 21-22).

In some embodiments herein described, iron chelation can be used to inhibit pathogenic microbial biofilms in vitro and in vivo.

In some embodiments, Fe(II) and Fe(III) chelators can be activated in combination to substantially minimize and/or disrupt biofilm growth as exemplified in Examples 21-22. In these embodiments, Fe(II) and Fe(III) chelators can act synergistically to substantially prevent and/or disrupt biofilm growth as also exemplified in Examples 21-22.

In some embodiments the Fe(II) chelator to be used in combination with an Fe(III) chelator is Ferrozine®. In some embodiments the Fe(III) chelator to be used in combination with an Fe(II) chelator is conalbumin. In some embodiments, the Fe(II) chelator and Fe(III) chelator administered in combination can be Ferrozine® and conalbumin (see, for example, Examples 21-22).

In particular, in some embodiments, the combination of activation of Fe(II) and Fe(III) chelators in combination can be used to target mature biofilms. Mature biofilms are of significance, for example, because increased resistance to antibiotics (see, for example, Ito et al. Applied and Environmental Microbiology 2009, 75, 4093-4100 and Example 22).

Thus, in some embodiments, a method for interfering with viability of bacteria comprises activating a combination of Fe(II) and Fe(III) chelators to substantially prevent and/or disrupt biofilm growth. In these embodiments, Fe(II) and Fe(III) chelators can act synergistically to substantially prevent and/or disrupt biofilm growth and can be used to target mature biofilms. (See, for example, Example 22).

The ability of the combination of Fe(II) and Fe(III) chelators in substantially preventing and/or disrupting biofilm growth can be due to the appreciable levels of ferrous iron [Fe(II)] which can exist in the majority of CF lung which can compromise Fe(III) chelation therapy under hypoxic or anoxic conditions. Such appreciable levels of Fe(II) can be due to localized hypoxic microenvironments exist which can stabilize Fe(II) (see, for example, Examples 19-22).

Thus, in some embodiments, a treatment for cystic fibrosis (CF) patients comprises administering Fe(II) and Fe(III) chelators in combination to substantially prevent and/or disrupt biofilm growth. (See, for example, Examples 19-22).

In some embodiments, compositions for substantially preventing and/or reducing biofilms are described. The composition comprises one or more agents able to inactivate a phenazine and/or a phenazine related pathway in the bacteria to reduce survivability of bacteria. (See, for example, Examples 1-5 and 19-22).

In some embodiments the composition comprises an Fe(II) chelator and an Fe(III) chelator. In some embodiments, the Fe(II) chelator is Ferrozine® and is comprised in the composition in an amount ranging between about 10 and about 1000 µM. In some embodiments, the Fe(III) chelator is conalbumin and is comprised in the composition in an amount ranging between about 10-1000 µM (see, for example, Examples 1-5 and 21-22).

In some embodiments, the composition comprises Ferrozine® in an amount ranging between about 10 and about 1000 µM and conalbumin Ferrozine® in an amount ranging between 10-1000 µM (see, for example, Examples 1-5 and 21-22).

In some embodiments, the composition comprises Ferrozine® in an amount of approximately 200 µM (see, for example, Examples 1-5 and 21-22).

In some embodiments, the composition comprises conalbumin in an amount of approximately 100 µM (see, for example, Examples 1-5 and 21-22).

In some embodiments, the composition comprising administering a combination of the Fe(II) chelator and the Fe(III) chelator to reduce biofilm accumulation by greater than approximately 20%. In some embodiments, composition comprising the combination of the Fe(II) chelator and the Fe(III) chelator reduces biofilm accumulation by greater than approximately 50% (see, for example, Examples 21-22).

In some embodiments, a method and system to interfere with the viability of bacteria is described, the method comprising the chelation of Fe(II) alone/or Fe(III) to reduce survivability and/or antibiotic resistance of the bacteria.

In some embodiments, Fe(II) and Fe(III) chelators can be activated in combination to substantially prevent and/or disrupt biofilm growth as exemplified in Examples 21-22. In these embodiments, Fe(II) and Fe(III) chelators can act synergistically to substantially prevent and/or disrupt biofilm growth as also exemplified in Examples 21-22.

In some embodiments the Fe(II) chelator to be used in combination with an Fe(III) chelator is Ferrozine®. In some embodiments the Fe(III) chelator to be used in combination with an Fe(II) chelator is conalbumin. In some embodiments, the Fe(II) chelator and Fe(III) chelator administered in combination can be Ferrozine® and conalbumin (see, for example, Examples 21-22).

In particular, in some embodiments, the combination of activation of Fe(II) and Fe(III) chelators in combination can be used to target mature biofilms. Mature biofilms are of significance, for example, because increased resistance to antibiotics (see, for example, Ito et al. Applied and Environmental Microbiology 2009, 75, 4093-4100).

Thus, in some embodiments, a method for interfering with viability of bacteria comprises activating a combination of Fe(II) and Fe(III) chelators to substantially prevent and/or disrupt biofilm growth. In these embodiments, Fe(III) and Fe(II) chelators can act synergistically to substantially prevent and/or disrupt biofilm growth and can be used to target mature biofilms. (See Example 22).

The ability of the combination of Fe(III) and Fe(II) chelators in substantially preventing and/or disrupting biofilm growth can be due to the appreciable levels of ferrous iron [Fe(II)] which can exist in the majority of CF lung which can compromise Fe(III) chelation therapy under hypoxic conditions. Such appreciable levels of Fe(II) can be due to localized hypoxic microenvironments exist which can stabilize Fe(II) (see, for example, Examples 19-22).

Thus, in some embodiments, a treatment for cystic fibrosis (CF) patients comprises administering Fe(III) and Fe(II) chelators in combination to substantially prevent and/or disrupt biofilm growth. (See, for example, Examples 19-22).

In some embodiments, compositions for substantially preventing and/or reducing biofilms are described. The composition comprises one or more agents able to chelate Fe(II) and/or Fe(III) to reduce survivability of bacteria. (See, for example, Examples 19-22).

In some embodiments the composition comprises an Fe(II) chelator and an Fe(III) chelator. In some embodiments, the Fe(II) chelator is Ferrozine® and is comprised in the composition in an amount ranging between about 10 and about 1000 µM. In some embodiments, the Fe(III) chelator is conalbumin and is comprised in the composition in an amount ranging between about 10 and about 1000 µM (see, for example, Examples 1-5 and 21-22).

In some embodiments, the composition comprises Ferrozine® in an amount ranging between about 10 and about 1000 µM and conalbumin Ferrozine® in an amount ranging between 10-1000 µM (see, for example, Examples 1-5 and 21-22).

In some embodiments, the composition comprises Ferrozine® in an amount of approximately 200 µM (see, for example, Examples 1-5 and 21-22).

In some embodiments, the composition comprises conalbumin in an amount of approximately 100 µM (see, for example, Examples 1-5 and 21-22).

In some embodiments, the composition comprising a combination of the Fe(II) chelator and the Fe(III) chelator reduces biofilm accumulation by greater than approximately 20%. In some embodiments, composition comprising the combination of the Fe(II) chelator and the Fe(III) chelator reduces biofilm accumulation by greater than approximately 50% (see, for example, Examples 21-22).

In some embodiments, the methods mentioned above can further comprise degrading phenazines in vivo and/or in vitro using methods and systems herein described.

Further, in some embodiments, a method and system for treating and/or preventing a bacterial infection in an individual is described. The method comprises administering an effective amount of one or more agents able to selectively inactivate phenazine and/or a phenazine related pathway in the bacteria, in particular in combination with an antibiotic and/or other antimicrobial. The system comprises one or more agents able to specifically inactivate a phenazine and/or a phenazine related pathway in the bacteria and an antibiotic and/or other antimicrobial (see, for example, Examples 19-22).

Further, in other embodiments, a method and system for treating and/or preventing a bacterial infection in an individual is described. The method comprises administering an effective amount of one or more agents able to selectively chelate Fe(II) and/or Fe(III), in particular in combination with an antibiotic and/or other antimicrobial. The system comprises one or more agents able to specifically chelate Fe(II) and/or Fe(III) and an antibiotic and/or other antimicrobial (see, for example, Examples 1-5 and 19-22).

In particular, in some embodiments, a method for treating and/or preventing bacterial infection associated with cystic fibrosis is described. The method comprises administering a therapeutically effective amount of a combination of Fe(III) and Fe(II) chelators to an individual (see, for example, Examples 19-22).

In some embodiments the administering can be performed by way of an aerosol comprising the Fe(III) and Fe(II)

chelators, however other forms of administration, identifiable by a skilled person, can be used.

In one embodiment, the administering of the Fe(III) and Fe(II) chelators substantially prevents and/or disrupts biofilm growth in the lungs of an individual infected with the bacteria, such as a CF patient (see, for example, Examples 19-22).

In some embodiments, Fe(III) and Fe(II) chelators can act synergistically to substantially prevent and/or disrupt biofilm growth and can be used to target mature biofilms (see, for example, Examples 19-22).

In some embodiments, the Fe(II) chelator is Ferrozine® and a therapeutically effective amount ranges from approximately 10 to approximately 1000 μM. More particularly, in some embodiments, the therapeutically effective amount of Ferrozine® is approximately 200 μM (see, for example, Examples 19-22).

In some embodiments, the Fe(III) chelator is conalbumin and a therapeutically effective amount ranges from approximately 10 to approximately 1000 μM. More particularly, in some embodiments, the therapeutically effective amount of conalbumin is approximately 100 μM (see, for example, Examples 19-22).

The term "treatment" as used herein indicates any activity that is part of a medical care for, or deals with, a condition, medically or surgically.

The term "prevention" as used herein indicates any activity which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates a physical status of the body of an individual (as a whole or as one or more of its parts), that does not conform to a standard physical status associated with a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The term "individual" as used herein in the context of treatment includes a single biological organism, including but not limited to, animals and in particular higher animals and in particular vertebrates such as mammals and in particular human beings.

The wording "selective", "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence. By "stable complex" is meant a complex that is detectable and does not require any arbitrary level of stability, although greater stability is generally preferred. The term "selective" "specific" "specifically" or "specificity" as used herein with reference to a chemical or biological activity of a first molecule to second molecule of a certain bacteria or group of bacteria refers to the ability of the first molecule to direct the activity towards the second molecule, together with substantially less to no activity between the first molecule and molecules that may be present of organisms other than the bacteria or group of bacteria.

In some embodiments, the method for treating and/or preventing a bacterial infection in an individual comprises inactivation of phenazines and/or one or more phenazine related pathways of the bacteria as describe in any of the above embodiments. In particular, the inactivation of the phenazines and/or one or more phenazine related pathways of the bacteria performed as describe in any of the above embodiments will be recognized by the skilled person as not interfering in a deleterious manner with the normal biochemical pathways of the individual.

In some embodiments, a method and system for identifying an antimicrobial is described. The method comprises contacting a microbe with a candidate agent and detecting the ability of the candidate agent of inactivating a phenazine and/or a phenazine related pathway in the bacteria. The system comprises one or more microbes and one or more agents capable of detecting phenazine and/or phenazine related pathways.

An "antimicrobial" as described herein indicates a substance that kills or inhibits the growth of microorganisms such as bacteria, fungi, or protozoans. Antimicrobial either kills microbes (microbiocidal) or prevent the growth of microbes (microbiostatic)

The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

In some embodiments, the method for identifying an antimicrobial further comprises contacting the microbe with an antibiotic and/or an additional antimicrobial to the individual.

In some embodiments, the one or more agents of inactivating a phenazine and/or a phenazine related pathway is the agent according to first aspect of the disclosure.

In some embodiments, the system for identifying an antimicrobial comprises one or more microbes and one or more agents capable of detecting phenazine and/or phenazine related pathways for simultaneous combined or sequential use in the method according to the first and second aspects of the disclosure.

In some embodiments, an antimicrobial is described. The antimicrobial comprises one or more agents able to inactivate a phenazine and/or a phenazine related pathway in the bacteria to reduce antibiotic resistance and/or survivability of bacteria and optionally a compatible vehicle for effective administrating and/or delivering of the one or more agents to an individual.

In some embodiments, a pharmaceutical composition for the treatment of cystic fibrosis is described. The pharmaceutical composition for the treatment of cystic fibrosis comprises one or more agents able to inactivate a phenazine and/or a phenazine related pathway in the bacteria to reduce survivability of bacteria. In some embodiments the pharmaceutical composition for the treatment of cystic fibrosis comprises an Fe(II) chelator and an Fe(III) chelator.

In some embodiments the pharmaceutical composition for the treatment of cystic fibrosis further comprises a suitable vehicle for effective administrating and/or delivering of the one or more agents to an individual.

In some embodiments, the Fe(II) chelator is Ferrozine® and is comprised in the pharmaceutical composition in an amount ranging between about 10 and about 1000 $\mu$M. In some embodiments, the Fe(III) chelator is conalbumin and is comprised in the pharmaceutical composition in an amount ranging between 10-1000 $\mu$M (see, for example, Examples 1-5 and 19-22).

In some embodiments, the pharmaceutical composition comprises Ferrozine® in an amount ranging between about 10 and about 1000 $\mu$M and conalbumin Ferrozine® in an amount ranging between about 10 and about 1000 $\mu$M (see, for example, Examples 1-5 and 19-22).

In some embodiments, the pharmaceutical composition comprises Ferrozine® in an amount of approximately 200 $\mu$M (see, for example, Examples 1-5 and 19-22).

In some embodiments, the pharmaceutical composition comprises conalbumin in an amount of approximately 100 $\mu$M (see, for example, Examples 1-5 and 19-22).

In some embodiments, the pharmaceutical composition comprising a combination of the Fe(II) chelator and the Fe(III) chelator reduces biofilm accumulation by greater than approximately 20%. In some embodiments, the pharmaceutical composition comprising the combination of the Fe(II) chelator and the Fe(III) chelator reduces biofilm accumulation by approximately greater than 20% or by approximately 50% (see, for example, Examples 19-22).

The term "vehicle" as used herein indicates any of various media acting usually as solvents, carriers, binders or diluents for PSA comprised in the composition as an active ingredient.

In some embodiments, the antimicrobial further comprises and antibiotic and/or an additional antimicrobial.

In some embodiments, the vehicle is a pharmaceutically acceptable vehicle and the composition is a pharmaceutical composition.

In particular some embodiments, the one or more agents can be included in pharmaceutical compositions together with an excipient or diluent and optionally with one or more antibiotics and/or other antimicrobial.

The term "excipient" as used herein indicates an inactive substance used as a carrier for the active ingredients of a medication. Suitable excipients for the pharmaceutical compositions herein disclosed include any substance that enhances the ability of the body of an individual to absorb the one or more agents. Suitable excipients also include any substance that can be used to bulk up formulations with the one or more agents to allow for convenient and accurate dosage. In addition to their use in the single-dosage quantity, excipients can be used in the manufacturing process to aid in the handling of the one or more agents. Depending on the route of administration, and form of medication, different excipients may be used. Exemplary excipients include but are not limited to anti-adherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluent include any substance that can decrease the viscosity of a medicinal preparation.

As disclosed herein, the antimicrobial agents herein described can be provided as a part of systems to perform any methods, including any of the assays described herein. The systems can be provided in the form of arrays or kits of parts. An array, sometimes referred to as a "microarray", can include any one, two or three dimensional arrangement of addressable regions bearing a particular molecule associated to that region. Usually, the characteristic feature size is micrometers.

In a kit of parts, the antimicrobial agent, candidate agents and other reagents to perform the method can be comprised in the kit independently. The antimicrobial agent can be included in one or more compositions, and each capture agent can be in a composition together with a suitable vehicle.

Additional components can include labeled molecules and in particular, labeled polynucleotides, labeled antibodies, labels, microfluidic chip, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In some embodiments, detection of a phenazine, and phenazine related activities can be carried either via fluorescent based readouts, in which the labeled antibody is labeled with fluorophore, which includes, but not exhaustively, small molecular dyes, protein chromophores, quantum dots, and gold nanoparticles. Additional techniques are identifiable by a skilled person upon reading of the present disclosure and will not be further discussed in detail.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit.

The kit can also contain, depending on the particular method used, other packaged reagents and materials (i.e. wash buffers and the like).

In some embodiments, the antimicrobial agents herein described can be included in pharmaceutical compositions together with an excipient or diluent. In particular, in some embodiments, disclosed are pharmaceutical compositions which contain at least one multi-ligand capture agent as herein described, in combination with one or more compatible and pharmaceutically acceptable vehicles, and in particular with pharmaceutically acceptable diluents or excipients. In those pharmaceutical compositions the multi-ligand capture agent can be administered as an active ingredient for treatment or prevention of a condition in an individual.

The term "excipient" as used herein indicates an inactive substance used as a carrier for the active ingredients of a medication. Suitable excipients for the pharmaceutical compositions herein described include any substance that enhances the ability of the body of an individual to absorb the multi-ligand capture agents or combinations thereof. Suitable excipients also include any substance that can be used to bulk up formulations with the peptides or combinations thereof, to allow for convenient and accurate dosage. In addition to their use in the single-dosage quantity, excipients can be used in the manufacturing process to aid in the handling of the peptides or combinations thereof concerned. Depending on the route of administration, and form of medication, different excipients can be used. Exemplary excipients include, but are not limited to, anti-adherents, binders, coatings, disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

Further advantages and characteristics of the present disclosure will become more apparent hereinafter from the following detailed disclosure by way or illustration only with reference to an experimental section.

EXAMPLES

The methods and systems and related compounds and compositions herein disclosed are further illustrated in the following examples, which are provided by way of illustration and are not intended to be limiting.

In particular, the following examples illustrate exemplary phenazine related pathways and related methods and systems according to the present disclosure. A person skilled in the art will appreciate the applicability and the necessary modifications to adapt the features described in detail in the present section, to additional solutions, methods and systems according to embodiments of the present disclosure.

The following materials and methods were used in performing the experiments illustrated in the examples herein described.

Chemicals.

Phenazine-1-carboxylate (PCA) was purified from aerobic stationary cultures of *P. fluorescens* strain 2-79 (NRRL B-15132) [1] grown in King's A medium [2] at 30° C., as previously described [3]. Pyocyanin (PYO) was purified from aerobic stationary cultures of *P. aeruginosa* strain UCBPP-PA14 [4] grown in LB at 37° C., as previously described [3]. Pyoverdin, purified according to the method described in Albrecht-Gary et al. [5], and pyochelin, characterized and synthesized according to the published procedures [6, 7], were provided by Professor Schalk's group (Institut de Recherche de l'Ecole de Biotechnologie de Strasbourg, IREBS FRE3211 CNRS/Université de Strasbourg, France). $Fe(OH)_3(s)$, referred to the Fe(III) mineral ferrihydrite, was synthesized according to the method described in Schwertmann and Cornell [8], as previously described [3]. Substantially iron-free conalbumin, 1,10-phenanthroline, hydroxylamine hydrochloride, ammonium acetate, ferrous ammonium sulfate, and carrier DNA for yeast transformation were purchased from Sigma-Aldrich. All enzymes used for DNA manipulation were purchased from New England Biolabs.

Strains, Plasmids, Primers and Growth Conditions.

In some of the examples, the strains, plasmids, and primers that are used are listed in Tables 1 and 2. For planktonic and biofilm experiments with *P. aeruginosa* PA14 strains, 0.3 g/L Bacto Tryptic Soy Broth ("1% TSB", where 1% is relative to the usual concentration of TSB medium (30 g/L); Becton Dickinson) was used as medium. Where indicated with the PA14 siderophore null strain (ΔpvdAΔpchE), 1.0 µM $Fe(OH)_3(s)$, 10 µM PCA or PYO, or 1.0 µM $Fe(OH)_3(s)$ together with 10 µM PCA or PYO was added to 1% TSB. Also as indicated with the PA14 wild type and feoB::MAR2xT7 mutant (from the non-redundant PA14 mutant library [9]), 10 µM PCA or PYO alone, 40 µg/ml iron-free conalbumin alone or together with 10 µM PCA or PYO was amended to 1% TSB. Flow-cell biofilm experiments with the PA14 wild type and phenazine deletion (Δphz) strains were also performed in 1% TSB supplemented with 10 µM PCA, respectively. To confirm that in contrast to PA14 wild type, the ΔpvdAΔpchE strain was unable to produce pyoverdin and pyochelin during planktonic growth, an iron deficient MOPS-based medium [100 mM MOPS at pH 7.2, 20 mM succinate, 93 mM $NH_4Cl$, 43 mM NaCl, 2.2 mM $KH_2PO_4$, 1 mM $MgSO_4$] [modified from ref 10] was used. These planktonic growth experiments were performed in acid-washed iron-free sterile glass culture tubes or polypropylene flasks at 37° C. with vigorous shaking at 250 rpm to generate aerobic conditions. To confirm that the PA14 feoB::MAR2xT7 mutant was disrupted in ferrous iron transport, cells were incubated shaking anaerobically in Amberlite-treated 1% TSB medium containing 100 mM $KNO_3$, 50 mM glutamate, 1% glycerol, and 100 µM iron source (either $(NH_4)_2Fe(II)(SO_4)_2$ or $Fe(III)Cl_3$) at 37° C. for 22 hours. Culture densities were followed at 500 nm ($OD_{500}$) in a Thermo Spectronic 20D+ or Shimadzu UV-2450 spectrophotometer.

*P. aeruginosa* PA14 strains and *Escherichia coli* strains used for mutant construction were cultured in Luria-Bertani (LB, Fisher Scientific) medium at 37° C. *E. coli* BW29427 and β-2155 were supplemented with 0.3 mM diaminopimelic acid. The yeast *Saccharomyces cerevisiae* uracil auxotrophic strain InvSc1 (Invitrogen) for gap repair cloning [11, 12] was grown with yeast extract-peptone-dextrose (YPD medium: 1% Bacto yeast extract, 2% Bacto peptone, and 2% dextrose) at 30° C., and selections were performed with synthetic defined agar (SDA) medium lacking uracil (URA, Qbiogene 4813-065). For selection and maintenance of plasmids pMQ30 and derivatives, as well as pAKN69, gentamicin was used at 15 µg/ml for *E. coli* and 75-100 µg/ml for *P. aeruginosa*, respectively. Selection and maintenance of *E. coli* containing pUX-BF13 was carried out on 100 µg/ml ampicillin.

TABLE 1

| Strain or plasmid | Properties | Reference or source |
|---|---|---|
| Strains | | |
| *P. aeruginosa* | | |
| PA14 | Clinical isolate UCBPP-PA14, wild type strain | [4] |
| PA14 Δphz | PA14 with deletions of operons phzA1-G1 and phzA2-G2 | [13] |
| PA14 ΔpvdAΔpchE PA14 | PA14 with deletions of pvdA and pchE | This study |
| ΔphzΔpvdAΔpchE | PA14 with deletions of pvdA, pchE, and operons phzA1-G1 and phzA2-G2 | This study |
| PA14-YFP | PA14 constitutively expressing YFP from a Tn7 insertion created by introducing plasmid pAKN69 | L.E.P. Dietrich, MIT |
| PA14 Δphz-YFP | PA14 Δphz constitutively expressing YFP, analogous to PA14-YFP | L.E.P. Dietrich, MIT |
| PA14 ΔpvdAΔpchE-YFP | PA14 ΔpvdAΔpchE constitutively expressing YFP plasmid pAKN69 | This study |
| PA14 ΔphzΔpvdAΔpchE-YFP | PA14 ΔphzΔpvdAΔpchE constitutively expressing YFP plasmid pAKN69 | This study |
| PA14feoB::M4R2xT7 | PA14 mutant with an insertion of the M4R2xT7 transposon in the PA14_56680 ORF, which is the homolog of the PAO1 ORF PA4358. | 191 |
| *E. coli* | | |
| UQ950 | DH5α λ pir host for cloning | D.P. Lies, Caltech |
| BW29427 | Donor strain for conjugation | W.M. Metcalf, UIUC |
| β-2155 | Donor strain for conjugation | [14] |
| *S. cerevisiae* InvSC1 | Ura⁻ for gap repair cloning | Invitrogen |
| Plasmids | | |
| pMQ30 | Yeast-based allelic exchange vector, sacB, CEN/ARSH, URA3⁺, $Gm^R$ | [15] |
| pUX-BF13 | R6K replicon-based helper plasmid, providing the Tn7 transposition functions in trans, which can only replicate when the pir gene is supplied in trans, $Amp^R$ | [16] |
| pAKN69 | Transposon delivery plasmid containing the mini-Tn7(Gm)$P_{A1/04/03}$::eyfp fusion | [17] |
| pYW01 | pvdA deletion fragments cloned into pMQ30 | This study |
| pYW02 | pchE deletion fragments cloned into pMQ30 | This study |

In some of the examples, *P. aeruginosa* PA14 and its derivatives were used in this study. Strain DKN330, a ΔphzA1-G1 ΔphzA2-G2 deletion mutant [13] is unable to produce any phenazine and is referred to here as Δphz1/2. Plasmid pAKN69, containing the mini-Tn7(Gm)$P_{A1/04/03}$:: eyfp fusion [18], was used to introduce a chromosomally-encoded constitutive eYFP into PA14 wild type and Δphz1/2, resulting in strains DKN372 and DKN373, respectively.

In some of the examples, *P. aeruginosa* strain PA14 [4] was used, which produces approximately ten times more pyocyanin in LB batch cultures than strain PAO1 [13]. The *P. aeruginosa* PA14 mutant containing the MAR2xT7 transposon inserted in the ldhA gene in a ΔexoU background was obtained from a publicly available mutant library [19] and is mutant ID #5174. Generation of the *P. aeruginosa* PA14 ΔphzA1-1G1 ΔphzA2-2G2 deletion mutant (hereafter referred to as the Δphz mutant) was described previously [13]. *P. aeruginosa* PA14 wild type and mutants were grown aerobically at 37° C. in LB Broth, Miller (Fisher Scientific) or modified MOPS synthetic medium [10]. Our modified MOPS synthetic medium contained 50 mM morpholinepropanesulfonic acid (MOPS, Sigma) at pH 7.2, 93 mM $NH_4Cl$, 43 mM NaCl, 2.2 mM $KH_2PO_4$, 1 mM $MgSO_4 \cdot 7H_2O$, and 3.6 μM $FeSO_4 \cdot 7H_2O$. Unless otherwise noted, 50 mM D-glucose was added to this medium as the sole carbon and energy source. Aerobic conditions were generated either through incubation with vigorous shaking at 250 rpm, or in a BioFlo 110 fermentor (New Brunswick Scientific) set to agitate at 250 rpm and bubble with 100% air at a rate of 2 L/minute. Aerobic culture volumes relative to vessel size are described below for specific experiments. Culture densities were followed at 500 or 600 nm in a Thermo Spectronic 20D+ or Beckman Coulter DU 800 spectrophotometer. Cultures with optical densities greater than 0.8 were diluted 1:10 in fresh medium to allow accurate measurements. The method used to test strains for the ability to survive via pyruvate fermentation is described in supplementary material.

Strain Construction.

*P. aeruginosa* synthesizes two known siderophores, the stronger Fe(III)-binding pyoverdin and the weaker Fe(III)-binding pyochelin [20]. Applicant constructed the siderophore null strain by generating unmarked deletions of pyoverdin and pyochelin biosynthetic genes pvdA [21] and pchE [22] in PA14 wild type, respectively. Analogously, Applicant constructed the phenazine-siderophore null strain in the PA14 phenazine null strain (Δphz). Applicant first deleted pvdA and then pchE. Here Applicant describes the protocol for in-frame deletion of pvdA using yeast gap repair cloning based on previously developed methods [11, 12, 15, 23]. The 5' and the 3' regions (both ~1 kb in lengths) of the sequence flanking pvdA were amplified using primer pairs pvdAKO1 (SEQ ID NO: 1)/pvdAKO2 (SEQ ID NO: 2) and pvdAKO3 (SEQ ID NO: 3)/pvdAKO4 (SEQ ID NO: 4), respectively (Table 2). These 5' and 3' flanking DNA fragments and the gapped plasmid vector pMQ30 were simultaneously introduced into the yeast *S. cerevisiae* uracil auxotrophic strain InvSc1 (Invitrogen) for in vivo recombination [11, 12]. The plasmid pMQ30 is an allelic exchange vector for Gram-negative bacteria unable to support replication of the ColE1 origin and contains CEN6/ARSH4 DNA sequences to support replication in *S. cerevisiae*, a URA3 yeast selectable marker, a multicloning site in a lacZα-allele for blue-white screening, an oriT for conjugation-mediated plasmid transfer, a gentamicin-resistance gene (aacC1); and the counter-selectable marker sacB [15]. Recombinant yeast cells were selected for on medium deficient in uracil. Plasmids were liberated from recombinant yeast and electroporated into *E. coli* UQ950, which was used as a host strain for plasmid replication [24]. Transformants containing recombination products of pMQ30 with the PCR products were isolated by blue/white screening and gentamicin resistance [24], yielding the construct for deleting the PA14 pvdA gene. This plasmid, which is called pYW01 (Table 1) was purified from *E. coli* UQ950, transformed by heat shock into *E. coli* BW29497 (a diaminopimelic acid auxotroph), and then mobilized into PA14 (wild type or the Δphz mutant) via biparental conjugation [25]. PA14 (wild type and the Δphz mutant) single recombinants (merodiploid containing the intact and the deleted pvdA gene) were isolated by selecting for gentamicin resistance. Resolution of the merodiploid was performed by selection on 10% sucrose, followed by PCR-based screening for loss of the wild type gene to isolate the pvdA deletion mutants (referred to as ΔpvdA and ΔphzΔpvdA). The deletion of pchE from strains ΔpvdA and ΔphzΔpvdA were generated the same way, using primer pairs pchEKO1 (SEQ ID NO: 5)/pchEKO2 (SEQ ID NO: 6) and pchEKO3 (SEQ ID NO: 7)/pchEKO4 (SEQ ID NO: 8) (Table 2). Besides using PCR-based diagnosis, the mutants ΔpvdAΔpchE and ΔphzΔpvdAΔpchE were further confirmed by their inability to produce pyoverdin or pyochelin when growing the mutant in iron deficient MOPS-based medium, in contrast to the wild type and the Δphz strains, respectively (see 'Analyses of Phenazines and Siderophores' for pyoverdin and pyochelin detections).

TABLE 2

| Primer | Sequence (5' to 3') |
|---|---|
| pvdAKO1 | CCA GGC AAA TTC TGT TTT ATC AGA CCG CTT CTG CGT TCT GAT AGC GCT GGA ACT CGC CAC (SEQ ID NO: 1) |
| pvdAKO2 | GCT TCA GGT GCT GGT ACA GTG CCT GAG TCA TTT CCA GTT CC (SEQ ID NO: 2) |
| pvdAKO3 | GGA ACT GGA AAT GAC TCA GGC ACT GTA CCA GCA CCT GAA GC (SEQ ID NO: 3) |
| pvdAKO4 | GGA ATT GTG AGC GGA TAA CAA TTT CAC ACA GGA AAC AGC TCT GAA GCC GAT GTT GAC CAC (SEQ ID NO: 4) |
| pvdEKO1 | CCA GGC AAA TTC TGT TTT ATC AGA CCG CTT CTG CGT TCT GAT CTG ATC CTC GTG CAG AGC (SEQ ID NO: 5) |
| pvdEKO2 | GGT CTG CAC CTG CAA GTG CAG GGC GGT ACG GGA ATC (SEQ ID NO: 6) |
| pvdEKO3 | GAT TCC CGT ACC GCC CTG CAC TTG CAG GTG CAG ACC (SEQ ID NO: 7) |
| pvdEKO4 | GGA ATT GTG AGC GGA TAA CAA TTT CAC ACA GGA AAC AGC TCG TCA GGT TGA GAC AGA ACG (SEQ ID NO: 8) |

To follow *P. aeruginosa* biofilm development using confocal microscopy, YFP-labeled PA14 strains were generated by introducing a chromosomally-encoded constitutive EYFP into the wild type, the phenazine null strain (Δphz), the siderophore null strain (ΔpvdAΔpchE), and the phenazine-siderophore null strain (ΔphzΔpvdAΔpchE), respectively. Plasmid pAKN69 containing the mini-Tn7 (Gm)$P_{A1/04/03}$-eyfp fusion was used for this purpose [17]. This plasmid was cloned into *E. coli* BW29427, and then mobilized into each PA14 strain via triparental mating with the helper plasmid pUX-BF13 (carrying the transposase genes) in *E. coli* 13-2155, as described previously [16, 26]. PA14 transformants with YFP constructs were selected with gentamicin and confirmed by YFP fluorescence.

Biofilm Experiments.

A flow cell system was constructed for biofilm experiments. The size of each flow channel was 1.5×4×34 mm; continuous flow of 1% TSB-based biofilm medium (with or without the respective additives detailed in the Results section) at the rate of 3 ml/h was supplied with a Watson-Marlow peristaltic pump; the temperature for biofilm growth was 22° C. An early stationary phase culture grown in 10% TSB was diluted to an $OD_{500}$ of 0.1 in biofilm control medium (1% TSB). Each flow cell was then inoculated with 300 μl of the diluted culture by injection with a 1 ml syringe. In order to allow cells to attach to the glass surface, the flow was arrested for 1.5 hours and then resumed throughout the length of each experiment (up to 6 days).

To image biofilms, confocal laser scanning microscopy (CLSM) with a Leica TCS SPE inverted microscope was used. For PA14 strains constitutively expressing EYFP (wild type, Δphz, ΔpvdADpchE, and ΔphzΔpvdAΔpchE), 3-dimensional fluorescence images were acquired using an excitation wavelength of 488 nm with constant intensity and collecting emission in the range of 510-618 nm. For the PA14 feoB::MAR2xT7 mutant, images were obtained using differential interference contrast (DIC) mode. To assure images used for comparisons of biofilm formation were representative and reproducible, multiple fields of view were acquired over time with a 10× dry objective in each flow cell within a single experimental set, and at least 4 independent experimental sets were performed. Fluorescence and DIC images were processed using Bitplane Imaris and NIH imageJ software. In most cases, fluorescence-based multiple biofilm image stacks (spaced 1-2 μm apart) were analyzed using the autoCOMSTAT software, a modified version of the COMSTAT biofilm evaluation package by Heydorn et al. [27, 28]. For each image a global threshold was calculated using the Robust Automated Threshold Selection algorithm with a critical-size setting of 20 μm, and connected-volume filtering was performed with a connectivity setting of 18 to remove free-floating biomass. Substratum coverage calculations were based on the first 3 μm above the substratum. The area of each analyzed image was $3.03 \times 10^5$ μm$^2$ and results from measurements of 1-6 images for each strain and treatment were averaged and sample standard deviations were calculated. The biofilm parameters reported here are biovolume per image area (referred to as biomass), substratum coverage, maximum height, and average height of the biomass, which excludes any area not covered by cells.

Iron Analysis.

In some examples, the total iron concentrations in TSB-based media and the mineral ferrihydrite [Fe(OH)$_3$(s)] suspensions were analyzed by the phenanthroline assay according to published protocols [29]. In summary, complete reduction of Fe(III) (soluble and/or mineral forms) to soluble Fe(II) was achieved by adding the reductant hydroxylamine hydrochloride to acidified samples. 1,10-phenanthroline and the pH buffer ammonium acetate were then added and allowed enough time to fully develop an orange-red Fe(II)-phenanthroline complex at pH 3.5. The total iron concentrations reflected by the colored Fe(II) complex were calculated based on the absorbance readings at 510 nm in a Shimadzu UV-2450 spectrophotometer. Iron in sterile, aerobic TSB-based media should be present as the oxidation state +3 even though the specific Fe(III) forms are unknown.

In some examples, ferrous iron and total iron were quantified using the Ferrozine® assay [56]. Briefly, 50 μL of sputum filtrate was added to 50 μL, of 1M HCl to quantify Fe(II). For total iron, 50 μL, was treated with 50 μL, of 10% hydroxylamine hydrochloride in 1M HCl to reduce Fe(III) to Fe(II). Samples were added to 100 μL of Ferrozine® (0.1% w/v in 50% ammonium acetate), incubated for 15 min, and absorbance was measured spectrophotometrically at 562 nm. Ferrous ammonium sulfate was used as the iron standard. Ferrozine® was also used to determine the Fe(II) composition of the trypticase soy broth (TSB) growth medium.

In some examples, samples were also analyzed by inductively coupled plasma mass spectrometry (ICP-MS), a highly sensitive mass spectrometry method capable of metal determination below one part per trillion. Briefly, 50 μL of filtrate was digested in 100 μL 8N nitric acid, and brought to a total of 1.5 mL in 5% nitric acid/indium standard. Samples were analyzed on an Agilent 7500 cx equipped with a reaction cell, using He (2 mL/min) and H2 (2.5 mL/min) as reaction gases. Fe concentrations were calculated using $^{56}$Fe and $^{57}$Fe signal intensities.

ICP-MS Versus Ferrozine® Determination of Total Iron.

In some examples, the accuracy and precision of the Ferrozine® assay are compromised as the proportion of Fe(II) increases, leading to overestimations of total iron concentrations [58]. To control for this, total sputum iron was quantified using ICP-MS. As expected, comparison of the two methods revealed a higher estimate of total iron using the colorimetric approach (FIG. 18). On average, Ferrozine® measurements were 30% greater than those obtained using ICP-MS, indicating that Fe(II) levels determined here were higher than those present in sputum. For this reason, a 30% reduction was applied to all reported ferrous iron sputum concentrations in FIG. 17 Panel A. Despite this conservative reduction, sputum Fe(II) levels are frequently greater than those used in our chelation experiments (~10 μM), which were sufficient to impede Fe(III)-chelation treatment.

Analyses of Phenazines and Siderophores.

Filtrates (0.2 μm pore size) were prepared from biofilm effluents or planktonic cultures. For characterizing and quantifying phenazines and the siderophore pyochelin, filtrates were directly loaded onto a Beckman System Gold reverse-phase HPLC with a diode array UV-VIS detector and a Waters Symmetry® C18 Analytical column (5 μm particle size; 4.6×250 mm). Analysis was performed in a gradient of water-0.1% trifluoroacetic acid (TFA, solvent A) to acetonitrile-0.1% TFA (solvent B) at a flow rate of 1.0 ml/min using the following method: for 0 to 1 min chromatography was in a linear gradient from 100% solvent A to 15% solvent B, for 1 to 12 min in a linear gradient to 58% solvent B, for 12 to 13 min in a linear gradient to 70% solvent B, for 13 to 25 min in a linear gradient to 85% solvent B, for 25 to 26 min in a linear gradient to 100% solvent A, for 26 to 29 min in 100% solvent A. Phenazines (e.g., PCA, PYO, phenazine-1-carboxamide, and 1-hydroxyphenazine) and pyochelin that are known to be potentially produced by P. aeruginosa can all be detected based on their characteristic absorption wavelengths and retention times as long as their concentrations are higher than 0.05-0.1 μM [3, 13, 30, 31].

The same HPLC instrument was used for analyzing the siderophore pyoverdin, with gradient profiling and sample preparation described in detail by Bultreys et al. [32]. In summary, filtrates with Fe(III)-chelated pyoverdin(s) at pH 5.0 were prepared for HPLC analysis by adding FeCl$_3$ into samples followed by filtration (0.2 μm pore size) and pH adjustment. Analysis was carried out in a gradient profiling with solvent A as water-17 mM NaOH-acetic acid at pH 5.0, and solvent B as acetonitrile (solvent B) [32]. For samples with pyoverdin being released at concentrations higher than 0.1 μM, a single Fe(III)-pyoverdin peak was detected at 403 nm. In addition, iron-free pyoverdin in filtered (0.2 μm pore size) biofilm effluents was analyzed using a fast fluorescence-based method by a BioTek Synergy 4 fluorescence plate reader with a Xenon Flash light source at the specific excitation/emission wavelength set of 405 nm/455 nm [33]. Control experiments and independent HPLC analysis confirmed that the measured fluorescence signal was predominantly contributed by pyoverdin and hence can be used for its detection and quantification.

Cell-Surface Attachment.

Attachment was analyzed using phase contrast imaging on a Leica confocal microscope. Stationary-phase cultures were diluted 1:50 in 10% LB and 0.5 ml of this suspension were pipetted into a sterile chambered system (Lab-Tek, Rochester N. Y.) with a borosilicate cover glass bottom. After 0.5 h or 4 h incubation at 22° C., unattached cells were discarded by gently replacing the supernatant with fresh medium, and attached cells were counted. Six fields of view for each strain and condition were analyzed and the percent of the surface covered by attached cells was estimated using Adobe Photoshop.

Motility Assays.

Swimming, swarming and twitching motilities were determined as previously described [34].

Flow cell biofilms were grown under constant flow at 22° C. in 1.5×4×34 mm flow cells. Continuous flow of 10% LB was supplied with a peristaltic pump at a constant rate of 3 ml 11$^1$. An early stationary-phase culture was diluted to an optical density at 500 nm of around 0.1 and 300 μl were inoculated into the flow cell. Strains expressing eyfp constitutively were used to visualize the biofilms. Upon inoculation, cells were allowed to attach in the absence of flow for 1.5 h before flow was resumed. Developing biofilms were imaged in 3 dimensions using a Leica confocal microscope. eYFP was excited with a 488 nm laser beam kept at constant intensity throughout the experiment, and emission from 510 to 618 nm was collected. Routinely, the Applicant observed that the distribution of bacterial cells throughout the colonized surface varied depending on the region of the flow cell, probably due to factors such as flow or accumulation of planktonic cells. To assure reproducibility, all images were acquired from an area set in the middle of the flow cell. Three images of duplicate flow cell lines were recorded and at least two independent experiments were performed.

Colony biofilms were grown on agar containing 1% tryptone as previously described [35]. Three colonies from independent spottings were documented for 8 days using an Epson scanner.

Preparation of Pyocyanin for Reduction Assays and NADH/NAD$^+$ Studies.

To maximize pyocyanin yields from P. aeruginosa cultures, a mutant, strain DKN370 was utilized, which contains two copies of the gene phzM. PhzM converts phenazine-1-carboxylic acid to the precursor for pyocyanin, 5-methylphenazinium carboxylate [36]. Purification of pyocyanin by organic extractions was carried out as described previously [13]. HPLC analysis verified the purity of pyocyanin after the extraction step, so the HPLC purification step described in [13] was omitted. Purified pyocyanin was dissolved in MOPS buffer (MOPS synthetic medium without FeSO$_4$, MgSO$_4$, or glucose), and filtered (0.2 μm).

Whole Cell Suspension Assay for Pyocyanin Reduction.

Cell culture samples were concentrated or diluted in filtrates of supernatants from the same culture to normalize optical density at 600 nm to 0.8. In an anaerobic chamber, the samples were transferred to cuvettes, and an anoxic solution of oxidized pyocyanin (in MOPS buffer) was added for a final pyocyanin concentration of about 0.1 mM. The cuvettes were stoppered to minimize oxygen exposure. Pyocyanin reduction was then followed as a decrease in absorbance at 690 nm over time in a DU 800 Beckman Coulter spectrophotometer. The rate of reduction could be calculated by converting the change in absorbance to μmol pyocyanin using the extinction coefficient for pyocyanin at this wavelength ($\varepsilon$=4310 M$^{-1}$ cm$^{-1}$ at pH 7 [37]) and the volume of sample in the cuvette (1 ml).

Quantification of Pyocyanin.

Pyocyanin concentrations in filtrates (0.2 μm pore) from LB and MOPS synthetic medium cultures were quantified as described previously [13]. Briefly, absorbance in LB culture filtrates was measured spectrophotometrically at 690 nm and pyocyanin concentrations were calculated using the extinction coefficient for pyocyanin (above). Pyocyanin concentrations in 200 µl sample filtrates from MOPS synthetic medium cultures were determined by HPLC analysis on a Waters Symmetry C18 reverse-phase column with a gradient method (water vs. acetonitrile containing 0.1% trifluoroacetic acid) and calculated based on absorbance values for purified standards diluted into MOPS buffer.

Extraction and Quantification of Intracellular NADH and $NAD^+$.

Extraction of NADH and $NAD^+$ was carried out according to the method described in San et al. [38]. Two×1 ml of culture were sampled into two separate microcentrifuge tubes and centrifuged at 16,000×g for 1 min. Supernatant was removed and pellets were resuspended in 300 µl of 0.2 M NaOH (for NADH extraction) or 0.2 M HCl (for $NAD^+$ extraction). These extracts were incubated for 10 min at 50° C., then for 10 min on ice. While vortexing, 300 µl of 0.1 M HCl (for NADH) or 0.1 M NaOH (for $NAD^+$) were added drop wise to neutralize the solutions. They were then centrifuged for 5 min at 16,000×g. Supernatants were transferred to fresh tubes and stored at −80° C. until quantification.

Relative or absolute NADH and $NAD^+$ were quantified using a modification [38] of the enzyme cycling assay developed by Bernofsky and Swan [39], adapted for measurement in a microtiter plate. A master reagent mix was prepared with 1× Bicine buffer (2.0 M, pH 8.0), 8× water, 1×80 mM EDTA, 2×100% EtOH, 2×4.2 mM thiazolyl blue (MTT), and 4×16.6 mM phenazine ethosulfate. The reagent mix was warmed to 30° C., then 90 µl aliquots were dispensed into individual wells of a 96-well microtiter plate. Five µl of standard or sample were added to each well, then the cycling reaction was started by the addition of 5 µl of alcohol dehydrogenase (Sigma #A-3263) prepared at 347 units/ml in 0.1 M Bicine (pH 8.0). The microtiter plate was incubated at 30° C., mixed by brief shaking, and read every 30-60 seconds for absorbance at 570 nm, which is the spectral peak of MTT that increases upon reduction. Slopes arising from plots of absorbance at 570 nm over time were generated for NADH and $NAD^+$ standards as well as all samples. Standard curves were used to calculate the absolute concentrations in µl\4, and values were normalized to optical density of the original cell culture sample.

Relative Quantification of Dissolved Oxygen in Batch Cultures.

Oxygen was measured in batch fermentor cultures using a Clark electrode [40]. The electrode was calibrated such that the reading obtained by the computer without the probe attached was equal to zero, while the initial reading for the uninoculated medium (after aeration and agitation for 12 hours) was set to 100 percent.

Analysis of Small Organic Acids in Culture Filtrates.

Two hundred µl were sampled from MOPS-glucose cultures (10 ml in an 18×150 mm test tube) at regular intervals and filtered (0.2 µm pore). In cases where repeated sampling from the same culture would alter the total culture volume by more than 10%, multiple identical cultures were inoculated from the same pre-culture and sampled sequentially. Twenty µl of each filtrate were loaded onto a Bio-Rad Aminex HPX-87H column (300×7.8 mm) and subjected to an isocratic method in 5 mM $H_2SO_4$ at 35° C., using a Waters HPLC system. Compounds were detected by UV absorbance at 210 nm. Absolute concentrations of pyruvate were calculated using a standard curve for pyruvate diluted in MOPS buffer. The identity of the pyruvate peak was verified by co-elution of an internal standard.

Sputum Collection.

In some experiments, sputum was obtained by expectoration and was immediately flash frozen in liquid nitrogen to minimize oxidation.

Sputum Processing.

In some examples, frozen sputum samples were allowed to thaw in an anaerobic chamber. Sputum was disrupted using a syringe and was further homogenized by vortexing in an equal volume of anaerobic 50 mM HEPES buffer. Sputum was centrifuged at 8,000×g for 10 min and supernatants were filtered through 0.22 µM columns for 20 minutes at 10,000×g. Filtrates were analyzed (anaerobically) for iron content. When sufficient material was obtained, 200 µL of filtrate was stored at −80° C. for ICP-MS analysis.

MBEC Assay for Biofilm Prevention and Dissolution.

In some examples, biofilm prevention and dissolution were measured via a high-throughput biofilm assay (MBEC Physiology and Genetics Assay) consisting of a 96-well plate into which a 96-peg plastic lid fits. This lid also fits over a standard 96-well plate, which was subsequently used to test the efficacy of iron chelators. Inoculum was prepared by diluting (30-fold) a 1.0 McFarland suspension of *P. aeruginosa* PA14 in TSB. 150 µl, was dispensed into each of the 60 inner wells, while 200 µl, of sterile trypticase soy broth (TSB) was placed in each perimeter well. For dissolution experiments, plates were incubated at 37° C. for 24 h, and were transferred to an anaerobic chamber for 24 h at 37° C. in anaerobic TSB containing 50 mM $KNO_3$. Biofilms were then exposed to conalbumin and/or Ferrozine® for 24 h. Each treatment was complemented with the addition of 80 µM ferrous ammonium sulfate. After treatment, lids were rinsed once in 50 mM HEPES, air dried for 10 min and quantified by crystal violet staining [57]. For biofilm prevention, anaerobic inoculum was amended with conalbumin and/or Ferrozine®. Media was replaced every 24 h by transferring the MBEC lid to a sterile plate containing growth media+/− treatments, and biofilms were allowed to develop for 168 h. Biomass was quantified as described above. Biological triplicates and six technical replicates (n=18) were used for each treatment.

Statistical Analysis.

Figure 17:
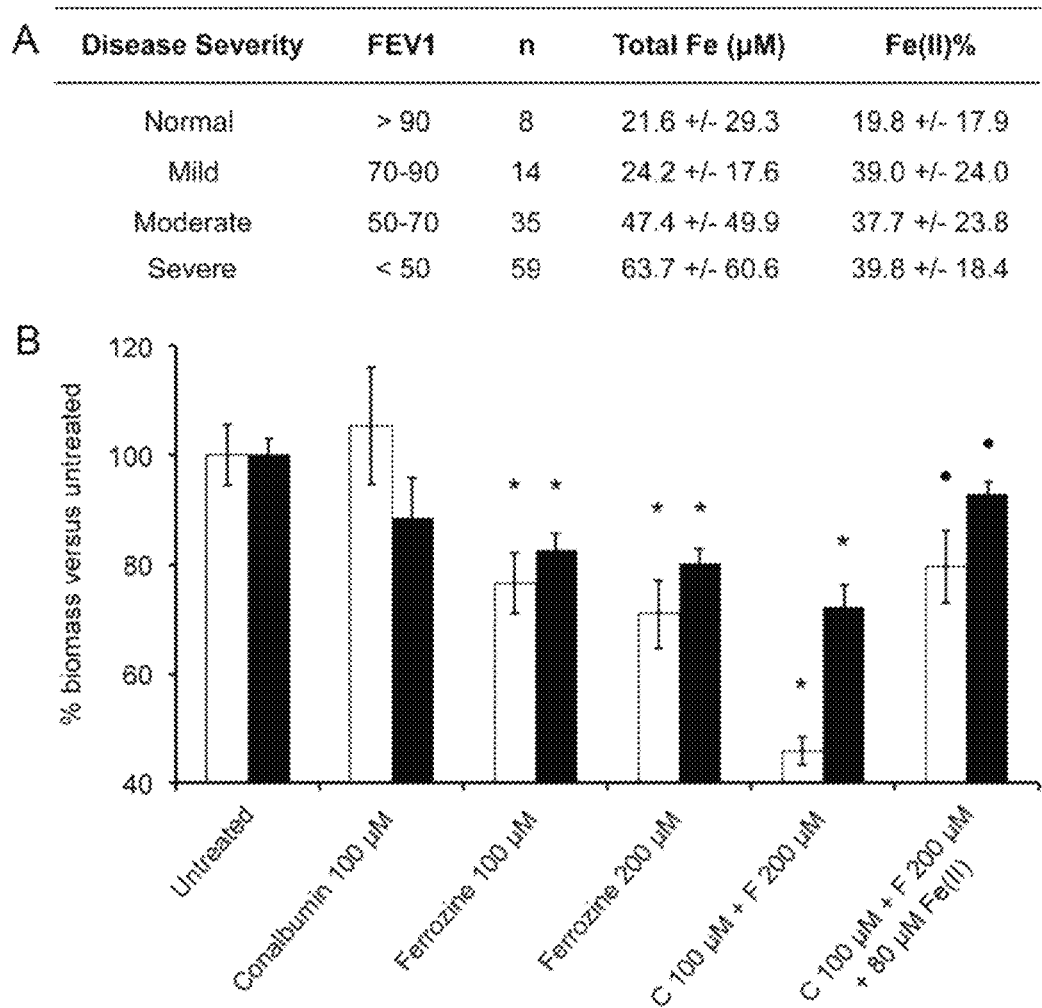
FIG. 17 Sputum iron chemistry versus disease severity. Reported values are mean concentrations+/– one standard deviation, and are conservative estimates based on 3-(2-Pyridyl)-5,6-diphenyl-1,2,4-triazine-p,p'-disulfonic acid monosodium salt hydrate, which is also known under the trademark Ferrozine® and ICP-MS measurements. (B) Biofilm growth prevention (white) and dissolution (black) by conalbumin (an Fe(III)-chelator) and Ferrozine® (an Fe(II)-chelator). Effects are mitigated by addition of 80 μM Fe(II). Symbols represent significance versus (*) untreated controls and (•) combination chelator treatment. Error bars represent the standard error of the mean (n=18).
Figure 18:
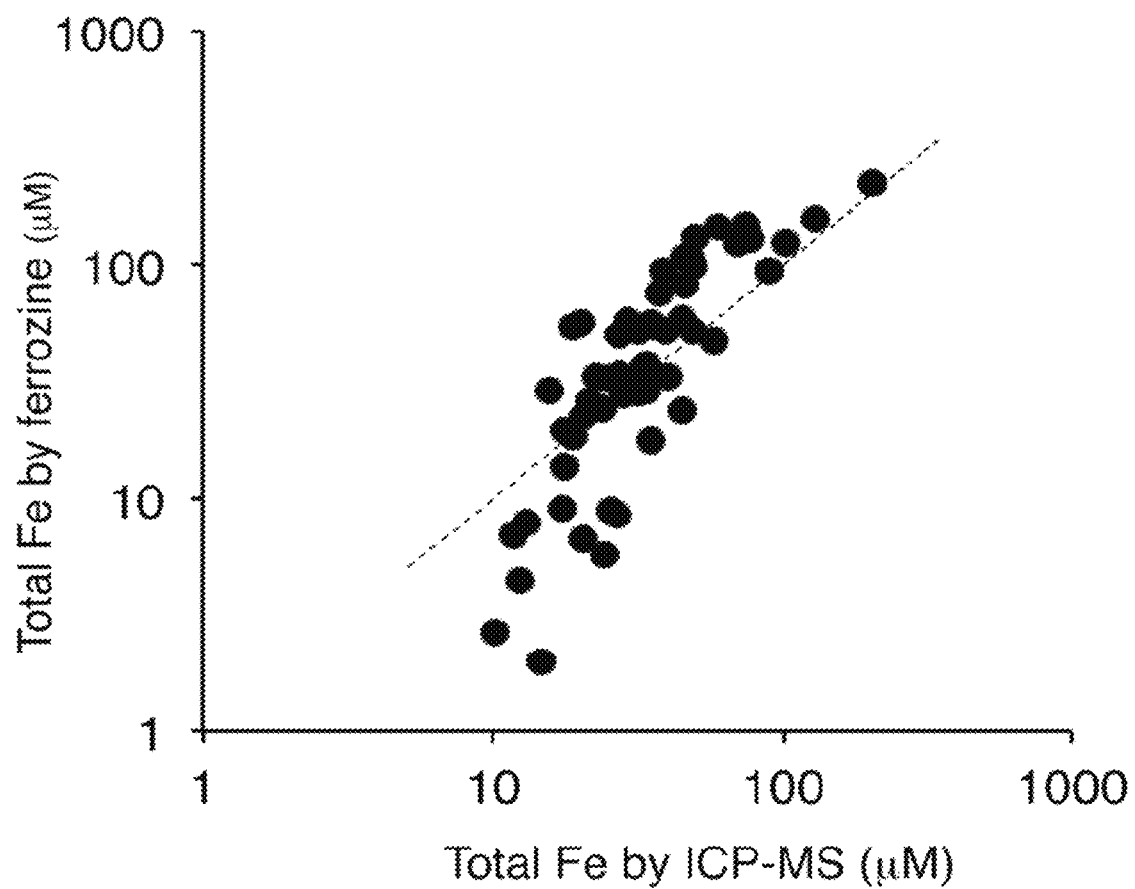
FIG. 18 Determination of total sputum iron using ICP-MS versus Ferrozine®. The latter approach generally estimates ~30% more total iron than the more sensitive mass spectrometry method. Dashed line represents the 1:1 trendline.

In some examples, two-tailed student t-tests were used for pairwise comparisons between patients groups (FIG. 17 Panel A) and chelator treatments relative to untreated controls (FIG. 17 Panel A). Pairwise comparisons were also performed between chelator treatments and those complemented with 80 µM Fe(II). In all cases, P<0.05 was considered statistically significant.

Example 1: Phenazine-1-Carboxylic Acid (PCA) can Work Together with the Siderophore Pyoverdin in Promoting Biofilm Development Biofilm development in *P. aeruginosa* PA14 wild type, a phenazine null strain (Δphz), a siderophore null strain (ΔpvdAΔpchE), and a phenazine-siderophore null strain (ΔphzΔpvdAΔpchE) under a flow of 1% TSB medium was monitored over 4 days. As illustrated in FIG. 1, wild type biofilm formation proceeded in the typical stages such that bacteria initially attached to the abiotic glass surface, clustered into microcolonies by day 1, which enlarged over time and eventually matured by day 4; the Δphz mutant, despite initially attaching equally well, formed fewer and smaller microcolonies over time in comparison to the wild type; the ΔpvdAΔpchE and ΔphzΔpvdAΔpchE mutants showed equally severe biofilm defects, and failed to develop microcolonies even 4 days after initial attachment (FIG. 1A). More quantitatively, the wild type biomass was only marginally higher than those of three other strains at day 1, but by day 4 was about 3-4 times greater than that of Δphz and 40-60 times those of ΔpvdAΔpchE and ΔphzΔpvdAΔpchE (FIG. 1B, Table 3). By day 4, the difference in total biomass between the wild type and Δphz mutant biofilms reflects variation mainly in thickness. On the other hand, the biofilm thickness observed for ΔpvdAΔpchE and ΔphzΔpvdAΔpchE was about the same as that of Δphz; their extremely low total biomass results primarily from a lack of surface coverage (Table 3).

operons being quorum-sensing regulated and that phenazines are typically only released at a high cell density.

The lack of phenazine production by ΔpvdAΔpchE matches our observation that ΔpvdAΔpchE and ΔphzΔpvdAΔpchE show equally severe biofilm defects. Collectively, these data indicate that both siderophores and phenazines (particularly PCA under these conditions) promote biofilm formation.

In view of the above it is expected that inactivation of genes involved in the production of phenazines result in inactivation of phenazine mediated biofilm formation in *P. aeruginosa* or other bacteria.

TABLE 3

| Time | PA14 strain | n | Total biomass ($\mu m^3/\mu m^2$) | Substratum coverage (%) | Avg. thickness of biomass ($\mu m$)[1] | Max. biofilm thickness ($\mu m$) |
|---|---|---|---|---|---|---|
| Day 1 | WT | 6 | 0.83 ± 0.11 | 7.1 ± 0.8 | 13.2 ± 0.4 | 40 |
|  | Δphz | 6 | 0.18 ± 0.03 | 1.9 ± 0.3 | 11.3 ± 0.8 | 35 |
|  | ΔpvdAΔpchE | 6 | 0.38 ± 0.08 | 4.5 ± 0.9 | 10.8 ± 0.4 | 28 |
|  | ΔphzΔpvdAΔpchE | 6 | 0.59 ± 0.08 | 5.7 ± 0.9 | 13.0 ± 0.6 | 37 |
| Day 2 | WT | 5 | 2.54 ± 0.41 | 14.0 ± 1.0 | 19.9 ± 3.4 | 89 |
|  | Δphz | 6 | 1.04 ± 0.15 | 10.0 ± 0.9 | 13.0 ± 1.9 | 60 |
|  | ΔpvdAΔpchE | 6 | 0.50 ± 0.08 | 4.5 ± 0.7 | 12.2 ± 0.2 | 33 |
|  | ΔphzΔpvdAΔpchE | 6 | 0.79 ± 0.13 | 6.3 ± 0.8 | 13.4 ± 0.5 | 31 |
| Day 4 | WT | 3 | 8.10 ± 0.75 | 28.1 ± 0.6 | 28.9 ± 3.0 | 95 |
|  | Δphz | 4 | 2.37 ± 0.26 | 23.1 ± 3.3 | 13.8 ± 0.7 | 44 |
|  | ΔpvdAΔpchE | 2 | 0.20 ± 0.09 | 1.5 ± 0.1 | 13.8 ± 4.3 | 47 |
|  | ΔphzΔpvdAΔpchE | 4 | 0.13 ± 0.05 | 1.0 ± 0.3 | 14.0 ± 0.9 | 36 |

All values are means of results of n images ± standard error of the mean. Each image covers an area of 3.03 × $10^5$ $\mu m^2$.
[1]Calculated for the area covered by biomass.

To further correlate phenazine and/or siderophore production with biofilm development, simultaneous analysis of the compounds being released into the biofilm effluents for the wild type, Δphz and ΔpvdAΔpchE strains was performed (FIG. 1C). The wild type started to release measurable levels of PCA (the precursor phenazine produced by all phenazine-making pseudomonads) and the siderophore pyoverdin beginning on day 2. Concomitant with biofilm development, both PCA and pyoverdin concentrations increased with time, with a dramatic rise in the PCA concentration by day 4.

Surprisingly, no other phenazines, including the blue colored pyocyanin (PYO), ever reached concentration levels above their respective HPLC detection limits (0.05-0.1 μM) under our biofilm growth conditions. Given that PYO is a highly diffusible zwitterion at circumneutral pH, Applicant interpreted the absence of PYO in the biofilm effluents to reflect little or no production rather than its retention in the biofilm matrix. The Δphz mutant started to release a measurable level of pyoverdin on day 2 and the pyoverdin concentration increased along with biofilm development. By day 4, despite the fact that the Δphz mutant released more pyoverdin than the wild type, it generated 3-4 times less biofilm biomass. Adding 10 μM PCA (comparable to the levels detected in wild type day 4 biofilm effluents) to the medium flow of the Δphz mutant throughout the experimental timescale increased the biofilm biomass four times by day 6, resulting in a biomass similar to the wild type. The ΔpvdAΔpchE mutant that failed to form biofilms did not release phenazines until day 4, and even then only at trace levels, consistent with one of the two phenazine biosynthetic Example 2: PCA can Promote Biofilm Formation by Generating Fe(II) in the Absence of Siderophores It is well established that pyoverdin promotes *P. aeruginosa* biofilm formation by facilitating iron acquisition. Effective iron acquisition is essential for biofilm development because more iron is required than for planktonic growth because it acts as a signal to trigger the transition from a motile to a sessile state. From the phenanthroline assay, the total iron concentration is calculated to be 0.2 μM in 1% TSB.

Because the medium was prepared aerobically at pH 7, the oxidation state of iron originally present in the medium should be +3, even though the specific Fe(III) forms are unknown. It is commonly believed that bioavailable iron in the micromolar concentration range is required for optimal bacterial growth, and hence the iron content in 1% TSB verges on the lower threshold. If the observed PCA-promoted biofilm formation (FIG. 1) were due to a stimulation in iron acquisition as a result of phenazine-facilitated Fe(III) reduction to Fe(II), one would expect that PCA would be able to circumvent the pyoverdin pathway if enough Fe(III) were provided.

Figure 2:
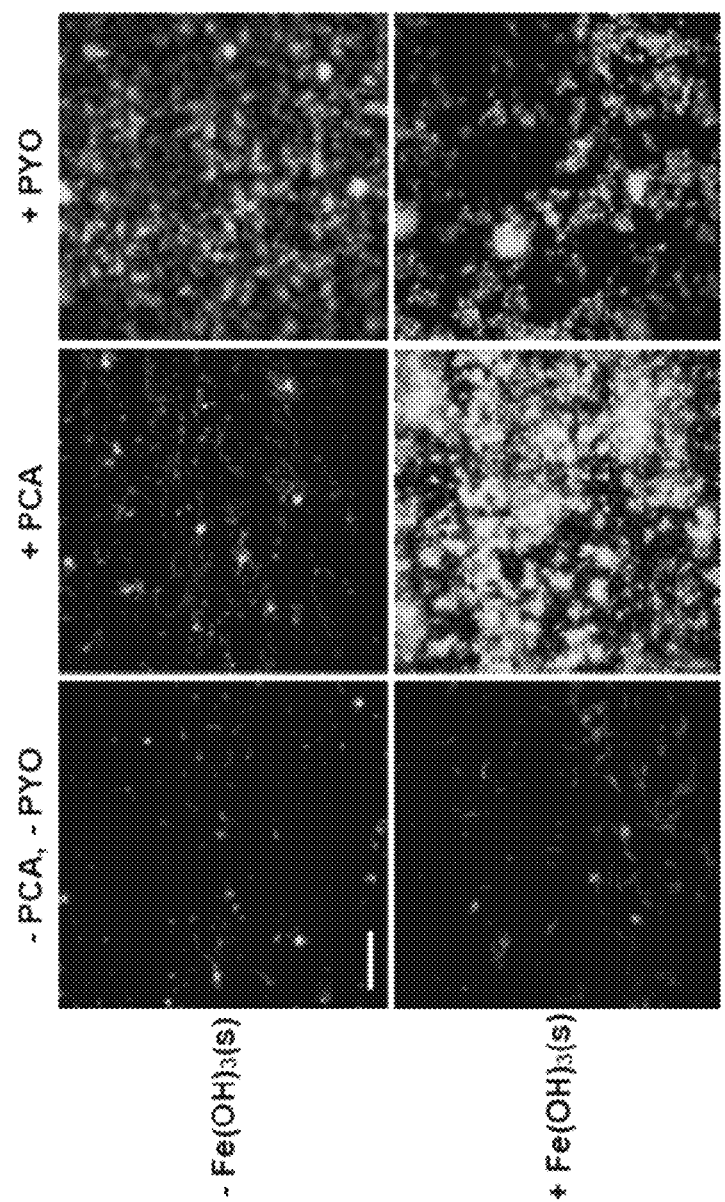
FIG. 2. PCA and PYO can circumvent the siderophore pathway for promoting *P. aeruginosa* biofilm development via Fe(II) uptake dependent and independent mechanisms, respectively. The effectively insoluble Fe(III) mineral ferrihyrite [Fe(OH)$_3$(s)] was the Fe(III) source. Confocal microscopic images of YFP-labeled *P. aeruginosa* PA14 siderophore null strain (ΔpvdAΔpchE) incubated in biofilm flow cells at 22° C. for 6 days with no addition, or with addition of 1.0 μM Fe(OH)$_3$(s), 10 μM phenazine (PCA or PYO), or 1.0 μM Fe(OH)$_3$(s) together with 10 μM phenazine (PCA or PYO), to 1% TSB medium. Images are top-down views (x-y plane); scale bar: 100 μm. Results are representative of 4 experiments. Related quantitative data can be found in Table 4.

To test whether PCA could rescue the biofilm defect in the PA14 ΔpvdAΔpchE mutant in the presence of sparingly soluble Fe(III), the effect of adding 1.0 μM ferrihydrite mineral suspension [Fe(OH)$_3$(s); K$_{sp}$=10-38.8 M [41]], 10 μM PCA, or 1.0 μM Fe(OH)$_3$(s) together with 10 μM PCA to the base medium (1% TSB) was examined. Adding exogenous PCA was necessary because, unlike the wild type, ΔpvdAΔpchE produced very little PCA on its own (FIG. 1C). Adding Fe(OH)$_3$(s) or PCA alone could not rescue biofilm formation by the ΔpvdAΔpchE mutant strain with statistical significance (FIG. 2, Table 4). In contrast, when Fe(OH)$_3$(s) and PCA were added together, dramatic rescue was observed (FIG. 2, Table 4).

This is consistent with prior abiotic experiments showing that some phenazines, including reduced PCA, can promote Fe(OH)$_3$(s) reduction over a broad pH range and liberate bioavailable Fe(II). The fact that adding PCA to 1% TSB can promote biofilm formation by the Δphz mutant (which makes pyoverdin but not phenazines) but not the ΔpvdAΔpchE mutant (which cannot make pyoverdin, and is severely delayed in making phenazines; FIG. 1C) further supports the conclusion that PCA and pyoverdin both contribute to biofilm formation. However, even in the absence of pyoverdin, PCA-promoted rescue can be achieved by adding just 1 μM Fe(III) to the base medium originally with 0.2 μM total Fe (FIG. 2, Table 4).

plasmic membrane protein FeoB. The identity of this mutant by sequencing and performing a diagnositic phenotypic test, was confirmed as follows.

Figure 3:
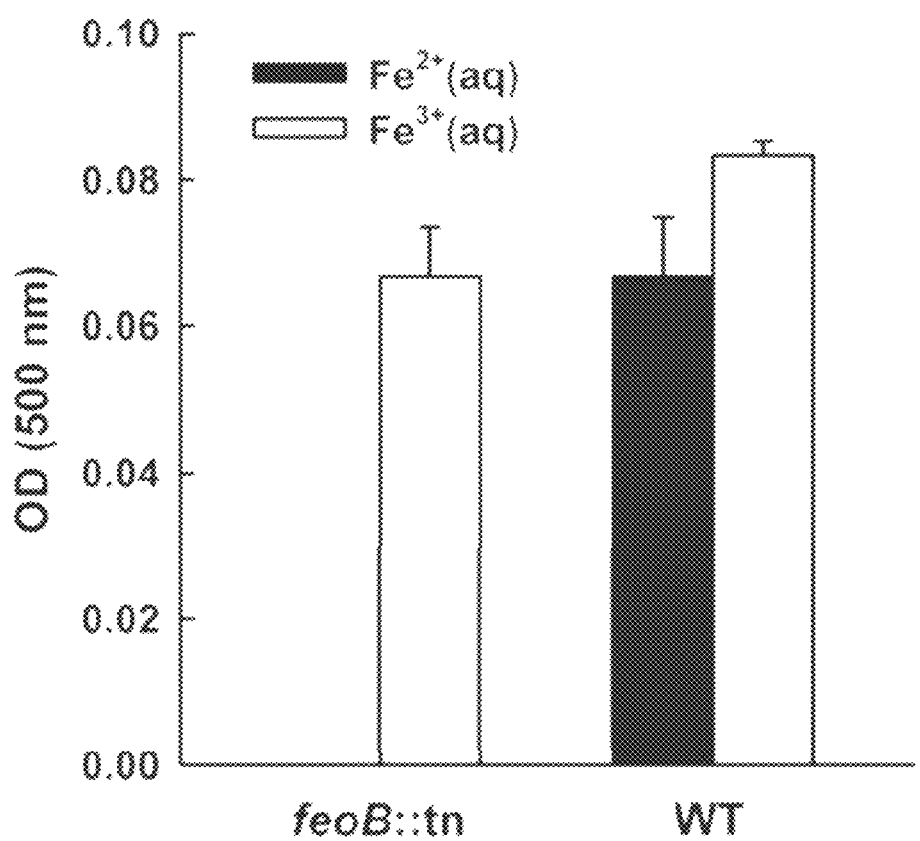
FIG. 3. The *P. aeruginosa* PA14 feoB::MAR2xT7 mutant (feoB::tn) cannot grow when given Fe(II) as its sole iron source, yet can grow in the presence of Fe(III); the wild type (WT) can grow regardless of whether iron was in the ferric or ferrous form. Cells were incubated shaking anaerobically in Amberlite-treated 1% TSB medium containing 100 mM KNO$_3$, 50 mM glutamate, 1% glycerol, and 100 μM iron source (either (NH$_4$)$_2$Fe(II)(SO$_4$)$_2$ or Fe(III)Cl$_3$) at 37° C. for 22 hours. Data reported are the mean of triplicate experiments±SD.

Because FeoB was recently shown to be the transporter required for energy-dependent Fe(II) uptake across the cytoplasmic membrane of *P. aeruginosa*, distinct from the more extensively studied TonB1-dependent ABC transport system for siderophore-mediated Fe(III) uptake, it is predicted that the feoB::MAR2xT7 mutant would not grow on Fe(II). To test this, experiments were performed in iron-free medium to which either Fe(II) or Fe(III) were added back. As expected, the feoB::MAR2xT7 mutant could not grow anaerobically in planktonic batch cultures when given Fe(II) as its sole iron source, yet could grow in the presence of Fe(III); under these same conditions, the wild type grew regardless of whether iron was in the ferric or ferrous form (FIG. 3). In 1% TSB

TABLE 4

| Time | Additive(s) to biofilm control medium (1% TSB) | n | Total biomass ($\mu m^2/\mu m^2$) | Substratum coverage (%) | Avg. thickness of biomass ($\mu m$)[1] | Max. biofilm thickness ($\mu m$) |
|---|---|---|---|---|---|---|
| Day 2 | none | | ND | | | |
| | 1.0 μM Fe(OH)$_3$(s) | 4 | 0.03 ± 0.00 | 0.4 ± 0.1 | 10.7 ± 2.0 | 30 |
| | 10 μM PCA | 4 | 0.05 ± 0.01 | 0.6 ± 0.2 | 12.6 ± 1.4 | 32 |
| | 1.0 μM Fe(OH)$_3$(s), 10 μM PCA | 4 | 0.45 ± 0.21 | 6.3 ± 3.3 | 11.1 ± 1.2 | 30 |
| | 10 μM PYO | 3 | 0.09 ± 0.03 | 0.8 ± 0.3 | 13.5 ± 0.4 | 34 |
| | 1.0 μM Fe(OH)$_3$(s), 10 μM PYO | 4 | 0.57 ± 0.29 | 7.3 ± 3.7 | 10.3 ± 0.5 | 34 |
| Day 4 | none | | ND | | | |
| | 1.0 μM Fe(OH)$_3$(s) | 3 | 0.05 ± 0.01 | 0.5 ± 0.2 | 12.1 ± 2.3 | 30 |
| | 10 μM PCA | 4 | 0.19 ± 0.00 | 2.9 ± 1.4 | 10.8 ± 0.9 | 34 |
| | 1.0 μM Fe(OH)$_3$(s), 10 μM PCA | 4 | 1.90 ± 1.08 | 12.5 ± 6.4 | 15.8 ± 1.8 | 44 |
| | 10 μM PYO | 4 | 0.83 ± 0.22 | 9.9 ± 2.4 | 10.1 ± 0.4 | 42 |
| | 1.0 μM Fe(OH)$_3$(s), 10 μM PYO | 4 | 3.16 ± 1.76 | 19.2 ± 9.2 | 10.8 ± 2.4 | 48 |
| Day 6 | none | 4 | 0.63 ± 0.16 | 6.0 ± 1.0 | 10.4 ± 0.8 | 40 |
| | 1.0 μM Fe(OH)$_3$(s) | 4 | 0.75 ± 0.33 | 3.3 ± 1.3 | 24.3 ± 1.6 | 82 |
| | 10 μM PCA | 3 | 0.21 ± 0.09 | 3.3 ± 2.1 | 15.1 ± 4.4 | 66 |
| | 1.0 μM Fe(OH)$_3$(s), 10 μM PCA | 4 | 4.87 ± 1.32 | 29.3 ± 8.5 | 18.9 ± 1.8 | 80 |
| | 10 μM PYO | 3 | 9.54 ± 0.18 | 44.3 ± 5.1 | 21.4 ± 2.1 | 94 |
| | 1.0 μM Fe(OH)$_3$(s), 10 μM PYO | 3 | 4.20 ± 0.17 | 31.8 ± 3.5 | 19.9 ± 2.6 | 56 |

ND = not determined.
All values are means of results of n images ± standard error of the mean. Each image covers an area of $3.03 \times 10^5$ $\mu m^2$.
[1]Calculated for the area covered by biomass.

This rescue occurred even with the total iron concentration (1.2 μM) being more than 10 times lower than that reported in CF sputum (generally greater than 10 μM, ranging from 17 to 200 μM). PCA therefore can stimulate *P. aeruginosa* biofilm formation in the presence of otherwise biologically unavailable Fe(III), even in the absence of pyoverdin if sufficient iron levels can be attained.

Example 3: PCA can Promote Biofilm Formation in the Presence of Conalbumin by Facilitating Fe(II) Uptake The previous experiments used the effectively insoluble mineral ferrihydrite to limit cells for Fe(III). While this may be relevant to understanding Fe(III) acquisition by *P. aeruginosa* in soil environments, in a clinical context, Fe(III) limitation results from binding by host-produced proteins of the transferrin family (including lactoferrin, serotransferrin, and conalbumin: $K_d \sim 10^{20-23}$ $M^{-1}$).

Figure 4:
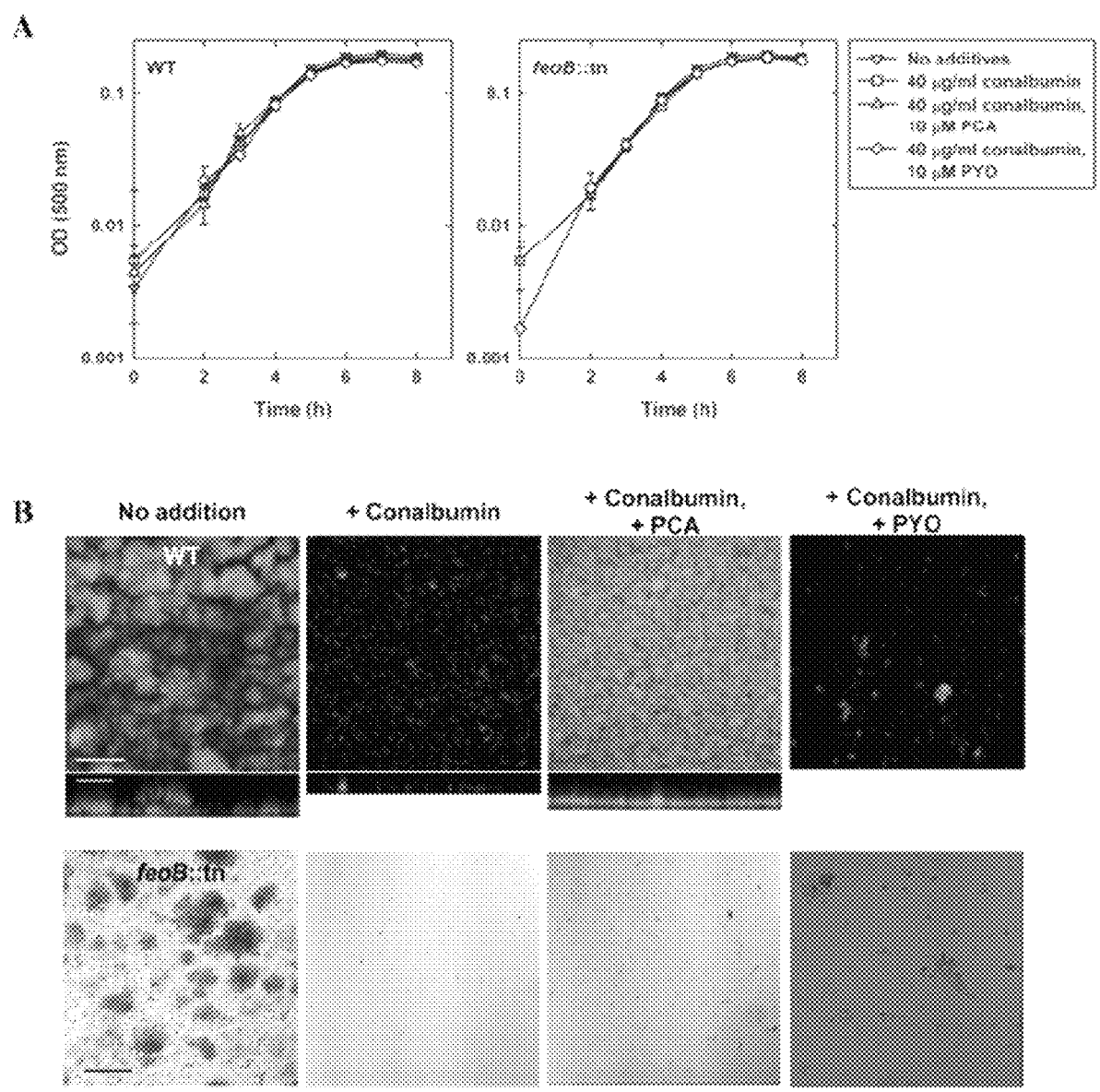
FIG. 4. A. The presence of sub-inhibitory levels of conalbumin alone or together with phenazine (PCA or PYO) does not inhibit planktonic growth of *P. aeruginosa* PA14 strains. Experiments were performed in batch cultures in 1% TSB-based biofilm medium at 37° C. Data reported are the mean of triplicate experiments±SD. B. PCA but not PYO can rescue the conalbumin-induced *P. aeruginosa* biofilm defect by reducing protein-sequestered Fe(III) with concomitant release of Fe(II). Confocal microscopic images of YFP-labeled *P. aeruginosa* PA14 wild type (WT), and DIC microscopic images of the *P. aeruginosa* PA14 feoB:: MAR2xT7 mutant (feoB::tn) disrupted in Fe$^{2+}$ transport into the cytoplasm, incubated in biofilm flow cells at 22° C. for 6 days with no addition, with addition of 40 μg/ml iron-free conalbumin alone, or together with 10 μM phenazine (PCA or PYO), to 1% TSB media flow. Confocal images consist of top-down views (x-y plane, top images) and side views (x-z plane, bottom images; enlarged and truncated to emphasize differences in the z dimension). DIC images are top-down views (x-y plane). Scale bars: 100 μm for top-down view images, 50 μm for side-view images. Results are representative of 4 experiments. Related quantitative data can be found in Table 5.
Figure 5:
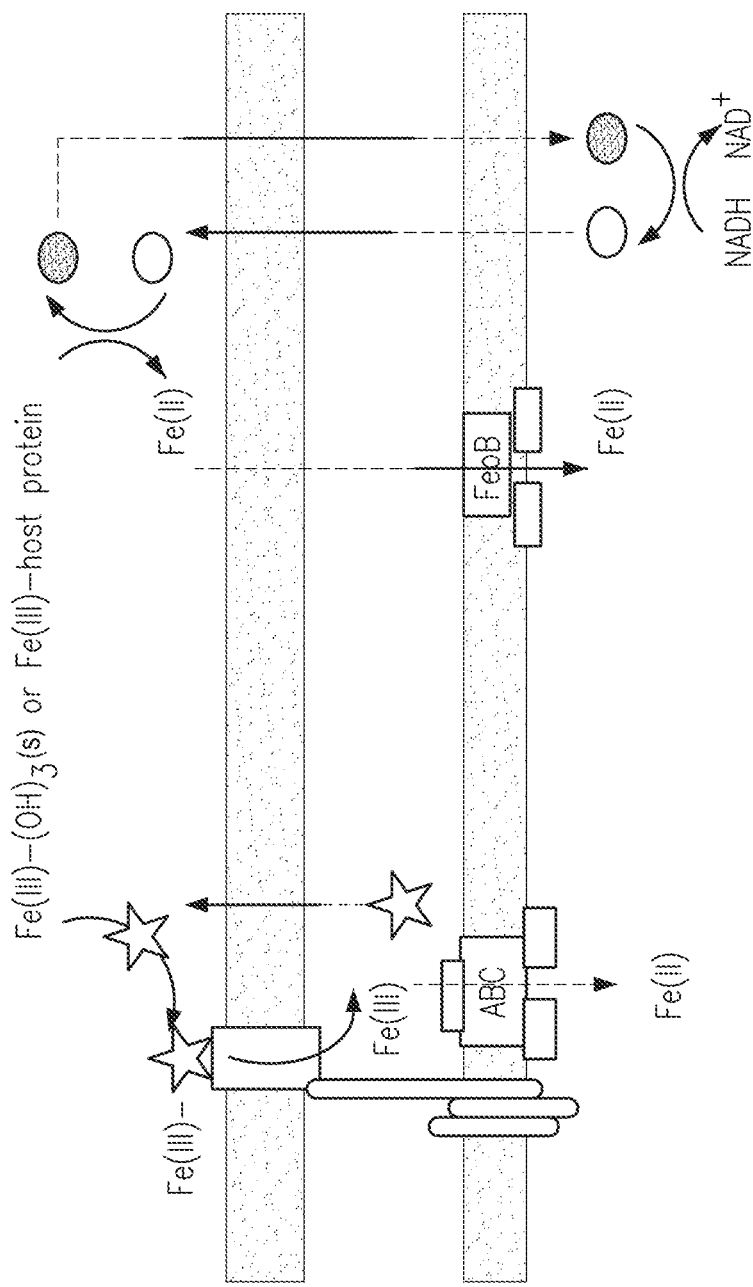
FIG. 5. Summary showing phenazine-facilitated Fe(II) uptake (on the right) in contrast to Fe(III) uptake (on the left). Fe(III) uptake is drawn in a highly simplified manner where the star depicts a siderophore, e.g. pyoverdin. The siderophore binds extracellular Fe(III) and crosses the outer membrane (OM) via a TonB-dependent transporter. In the periplasm, Fe(III) is released from the siderophore, which can then be recycled; Fe(III) is reduced by an unknown mechanism to Fe(II) in the periplasm (P) and transported across the cytoplasmic membrane (CM) presumably by an ABC transport system. In contrast, phenazines can reduce extracellular Fe(III) to Fe(II). After entering the periplasm, presumably via an OM porin, Fe(II) is transported across the CM via FeoB. Phenazines themselves are recycled, and enter and leave the cell through various transporters (not drawn for simplicity). Intracellularly, phenazine reduction is coupled to NADH oxidation to NAD$^+$, although whether this reduction is enzyme-mediated is unknown. Reduced phenazine is indicated by the open oval; oxidized phenazine by the filled oval.

To test whether PCA could stimulate biofilm development by facilitating Fe(II) uptake through reductive liberation of Fe(II) from host Fe(III)-binding proteins, a pathway that is independent of siderophore-mediated Fe(III) uptake, biofilm development under a flow of 1% TSB was compared between the wild type and the feoB::MAR2xT7 mutant, a strain disrupted in gene PA14_56680, encoding the cytomedium, both strains developed into mature biofilms over time, as expected (FIG. 4B). However, when the amount of available iron was reduced by adding the iron chelator, conalbumin (in its iron-free form), neither strain formed biofilms.

Previous researchers have also used conalbumin as a lactoferrin surrogate in these type of experiments, because they have a similar structure, Fe(III)-binding capacity, and effect on biofilm formation. To confirm the amounts of conalbumin and PCA used in the biofilm experiments specifically affected the amount of iron required to signal biofilm formation, and not the amount of iron required for planktonic growth, planktonic growth by the wild type and feoB::MAR2xT7 mutant was measured; the additive(s) had no effect on the growth of either strain (FIG. 4A). When both conalbumin and PCA were added, making the acquisition of sufficient iron to signal biofilm formation dependent upon PCA-mediated reduction of conalbumin-bound Fe(III) to Fe(II), the wild type could form biofilms but the feoB:: MAR2xT7 mutant could not.

For both the wild type and feoB::MAR2xT7 mutant, in contrast to the mature biofilms formed in medium without additives, in medium with added conalbumin, attached bacteria mostly remained as separated individual cells and failed to form clusters even after 6 days (FIG. 4B). This is similarly observed for *P. aeruginosa* strain PAO1 in the presence of lactoferrin. In accord with the conalbumin-induced severe biofilm defect, little PCA was released into the biofilm effluents by either strain (~0.05-0.1 μM), as expected for density-dependent phenazine production. For the wild type, the addition of PCA to conalbumin-treated medium rescued the defect by promoting biofilm growth into a uniformly distributed lawn type structure within 6 days, distinct from the mushroom-like structures observed in control medium (FIG. 4B). With PCA-induced rescue, by day 6, biofilm biomass increased by a factor of 13 compared to biofilms treated with conalbumin alone; the total biofilm biomass was comparable to that in medium without additives (Table 5).

with PYO being a thermodynamically less favorable reductant than PCA. However, this result was somewhat unexpected, given an earlier study by Cox reported that *P. aeruginosa* could reduce transferrin-bound Fe(III).

A possible explanation herein provided for guidance purpose and which is not intended to be limited is that PYO did not stimulate conalbumin-bound Fe(III) reduction for us, but did stimulate transferrin-bound Fe(II) reduction for Cox, is because one or more of the following caveats apply: (i) even though proteins within the transferrin family (such as conalbumin and transferrin) have similarly strong Fe(III) binding capacities, the $k_d$ values can still be different by 2-3 orders of magnitude [42]; (ii) a given phenazine's Fe(III)

TABLE 4

| Time | PA14 strain | Additive(s) to biofilm control medium (1% TSB) | n | Total biomass ($\mu m^3/\mu m^2$) | Substratum coverage (%) | Avg. thickness of biomass ($\mu m$)[1] | Max. biofilm thickness ($\mu m$) |
|---|---|---|---|---|---|---|---|
| Day 6 | WT | none | 1 | 7.20 | 46.7 | 16.4 | 62 |
| | | 40 μg/ml conalbumin | 6 | 0.80 ± 0.08 | 11.8 ± 1.3 | 9.0 ± 0.7 | 32 |
| | | 40 μg/ml conalbumin, 10 μM PCA | 4 | 10.70 ± 0.49 | 80.0 ± 4.3 | 13.2 ± 0.8 | 36 |
| | | 40 μg/ml conalbumin, 10 μM PYO | 1 | 0.34 | 4.2 | 8.7 | 32 |

ND = not determined.
All values are means of results of n images ± standard error of the mean. Each image covers an area of 3.03 × $10^5$ $\mu m^2$.
[1]Calculated for the area covered by biomass.

The wild type biofilm developed similarly with respect to structure and biomass regardless of whether PCA was added to the control medium, indicating that PCA-induced rescue was specific to the biofilm defect caused by the conalbumin treatment. On the contrary, for the feoB::MAR2xT7 mutant with a disrupted Fe(II) transporter, PCA addition failed to rescue the conalbumin-induced biofilm defect (FIG. 4B). Together, these results indicate that PCA's ability to rescue biofilm formation in the presence of the Fe(III)-binding protein conalbumin is because it makes Fe(II) bioavailable by reducing protein-sequestered Fe(III) through extracellular electron transfer.

Example 4: The Phenazine Pyocyanin (PYO) can Affect Biofilm Formation Independent of Facilitating Fe(II) Uptake PYO, a well-studied phenazine produced by *P. aeruginosa* and also detected in CF sputum, has been previously shown to affect biofilm formation in LB-based medium. Even though PYO was not released under the 1% TSB-based biofilm medium conditions, analogous experiments were performed to examine whether PYO might promote biofilm development in the same manner as PCA. Firstly tested was whether PYO could rescue the biofilm defect in the PA14 ΔpvdAΔpchE mutant, by comparing the effect of adding 10 μM PYO alone to the effect of adding 1.0 μM Fe(OH)$_3$(s) and 10 μM PYO together to the base medium (1% TSB). In contrast to PCA's rescue occurring only together with 1.0 μM Fe(OH)$_3$(s) addition, PYO rescued the biofilm defect regardless of whether Fe(OH)$_3$(s) was present; the rescue without Fe(OH)$_3$(s) was 2 times higher than with Fe-(OH)$_3$(s) addition (FIG. 2, Table 4).

Whether the addition of PYO to conalbumin-treated 1% TSB medium could rescue the PA14 wild type biofilm defect was tested. Unlike PCA, adding PYO did not rescue the conalbumin-induced biofilm defect (FIG. 4B, Table 5). This implies that PYO cannot efficiently reduce conalbumin-bound Fe(III) under these conditions, which is consistent reduction activity depends on factors such as concentration ratios between reactants (e.g. phenazine vs. chelated Fe(III)), and/or the presence of other oxidants that could react more readily with reduced phenazines.

For example, reduced PYO has been shown to be much more reactive towards oxygen than reduced PCA, making PYO more subject to oxygen competing with Fe(III) as an electron acceptor [3]. Consistent with this, in the whole bacterial cell suspension system studied by Cox, PYO was demonstrated to be only efficient at reducing transferring-bound Fe(III) under a strict anaerobic condition [43]. Considering our flow cell biofilm system is very different from the one studied by Cox both with respect to oxygen content and other factors, it makes sense that phenazine reactivity would be different. Interestingly, PYO did not stimulate iron-independent rescue under these conditions either, in contrast to what was observed for the ΔpvdAΔpchE mutant under different iron-limited conditions (FIG. 2).

Figure 6:
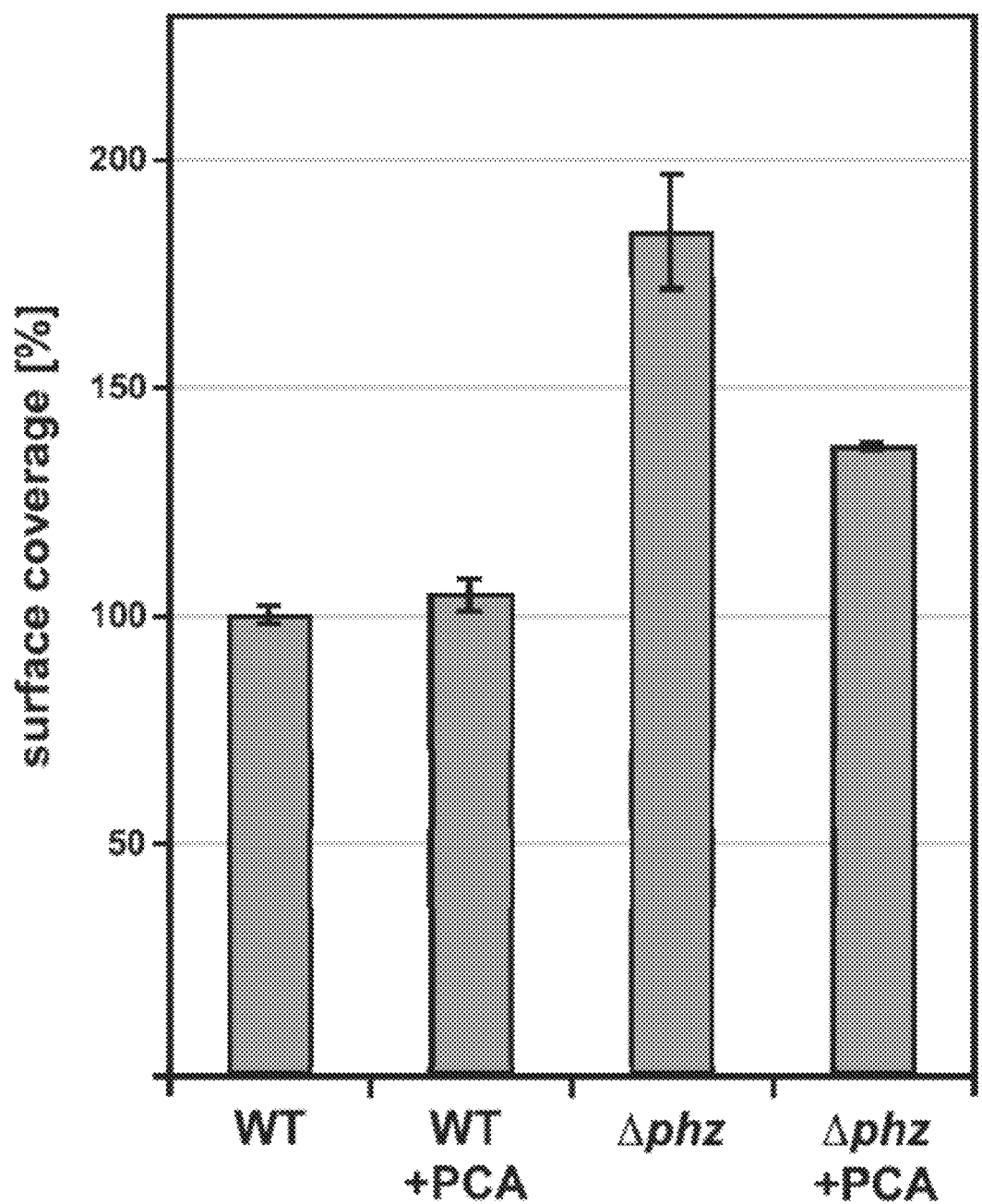
FIG. 6. Δphz1/2 has increased swarming motility. Quantification of swarming motility. Images of three swarming plates for each strain or condition were captured, exported to Adobe Photoshop and the agar surface covered by the swarms was quantified using the Analysis Tools.

Example 5: The Effect of Phenazines as a Signaling Compound Facilitating Bacterial Biofilm Development The effect of phenazines on bacterial motility. Previous studies have shown that *P. aeruginosa* attachment to surfaces is mediated by flagella, whereas movement along colonized surfaces is driven by pili, giving rise to cell aggregates that grow to form mature biofilms. *P. aeruginosa* PA14 is capable of three types of motility: 1) swimming in fluid media, accomplished via reversible rotation of flagella, 2) twitching, a surface-associated movement mediated by type IV pili, and 3) swarming, which also occurs on solid surfaces and is dependent on flagella. It was found that swimming and twitching motilities of the Δphz1/2 mutant were indistinguishable from the wild-type strain. However, swarming motility was significantly higher in Δphz1/2 (FIG. 6). After 40 h incubation, the Δphz1/2 mutant covered on average 84% more surface than the wild type. Addition of 100 μM PCA to the swarming agar had no effect on the wild type, but it significantly decreased the motility of the Δphz1/2 mutant. Addition of 100 μM pyocyanin had no inhibitory effect on swarming of either the wild type or Δphz1/2. Altered swarming motility often correlates with differences in rhamnolipid or other surfactant production. Using a drop-collapse assay significant difference in surfactant production between the wild-type and Δphz1/2 strains was observed.

Figure 7:
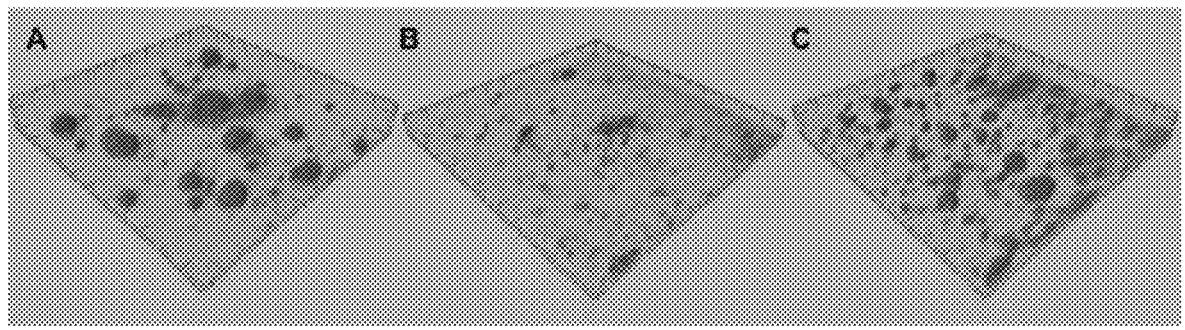
FIG. 7. Phenazines support development of structured biofilms in a continuous flow cell-system. Representative images of 4-day old biofilms of the wild-type (A) and phz1/2 mutant without (B) and with addition of 25 μM pyocyanin (C) to the nutrient flow. Images of similar positions in the flow cell were taken in triplicate. Three independent experiments were performed with similar results.

To measure the impact of phenazines on biofilm formation directly, a flow cell system was first used to grow wild-type and Δphz1/2 biofilms. In this system, the wild type formed heterogeneous biofilms that after 4 days developed large and abundant microcolonies (FIG. 7A). Biofilms of Δphz1/2 were flatter and consisted of fewer and smaller aggregates scattered throughout the field of view (FIG. 7B). The morphology of 4-day-old biofilms was analyzed using COMSTAT. A fixed threshold value and connected volume filtration were used for all image stacks. Table 6 summarizes the values calculated for mean biofilm thickness, substratum coverage, number of microcolonies at the substratum, surface-to-volume ratio and maximum biofilm thickness for three independent experiments. While the wild type showed a higher maximum biofilm thickness than Δphz1/2, the phenazine-deficient mutant showed a higher surface-to-volume ratio. When Δphz1/2 biofilms were grown in the presence of 25 μM pyocyanin (FIG. 7C), larger microcolonies and thicker biofilms resulted. PCA was not tested under these conditions. The mean thickness, the number of microcolonies and the total biomass volume all increased, reaching numbers similar or even higher than those observed for the wild type (Table 6). These results indicate that pyocyanin actively shapes the architecture of P. aeruginosa flow cell biofilms.

TABLE 6

Quantitative analysis of
4 day-old biofilms formed by the wild-type and a
phenazine defective mutant.

|  | Wild-type | ☐Δphz1/2 | Δphz1/2 PYO [a] |
|---|---|---|---|
| Total Biomass (μm³/μm²) | 2.2 ± 0.49 | 0.41 ± 0.04 | 4.3 ± 1 |
| % Coverage at substratum | 8 ± 1 | 2.7 ± 0.6 | 15.2 ± 2.46 |
| Maximum thickness | 54.7 ± 6.4 | 40 ± 2 | 57.5 ± 1.9 |
| Average thickness | 2.4 ± 0.59 | 0.47 ± 0.03 | 5.6 ± 1.6 |
| Number of microcolonies [b] | 9.3 ± 3 | 2 | 8 ± 1.5 |
| Average size of colonies at substratum (μm²) | 46.4 ± 13 | 12.1 | 102.6 ± 31 |
| Average colony volume (μm³) | 1551 ± 498 | 251.9 | 8170 |
| Roughness coefficient | 1.75 | 1.9 | 1.3 |
| Surface to volume ratio (μm²/μm³) | 3.5 ± 0.23 | 10.5 ± 3.6 | 6.6 ± 0.6 |

Analysis was conducted using COMSTAT.
Images from similar positions in the flow cell were acquired for all conditions in triplicate.
[a] 25 μM pyocyanin (PYO) was added to the medium from the beginning of the experiment.
[b] Minimum microcolony size at the substratum was set at 10 μm².

Example 6: The Effect of Phenazines on Colonial Morphology and Structure

Figure 8:
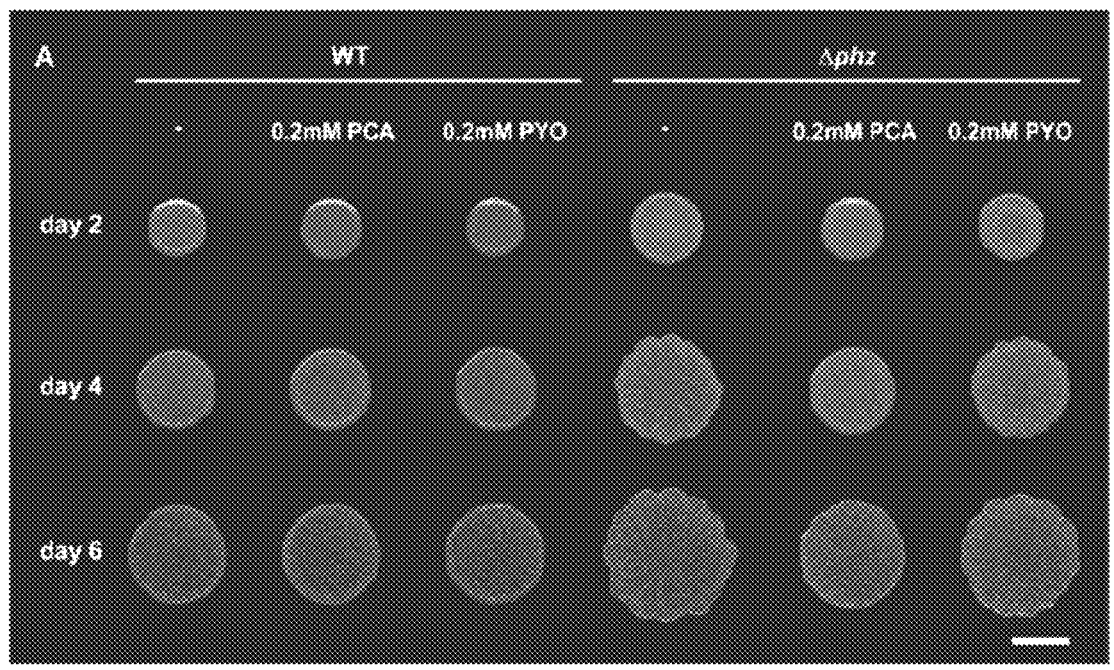
FIG. 8. Phenazines modulate colony-biofilm morphology. (A, B) *P. aeruginosa* PA14 wild-type and Δphz1/2 cultures were spotted onto 1% agar plates (containing 1% tryptone, 40 μg/ml Congo Red and 20 μg/ml Coomassie Blue) and incubated at 20° C. for 7 days in the presence of 0.1 mM PCA, 0.1 mM or in the absence of supplements. Each day colonies from three independent experiments were scanned and their surface coverage was determined. Representative images of colonies at day 2, 4 and 6 are shown (A; scale bar is 1 cm). The data in (B) show the average surface coverage and standard deviation for the three independent experiments. (C) Phenazine titrations. Colonies were grown as above, supplemented with 0, 0.1, 0.2, 0.3 or 0.4 mM PCA or pyocyanin. Surface coverage of colonies from three independent experiments was determined after incubation at 20° C. for 7 days. Bars indicate the standard deviation.
Figure 8:
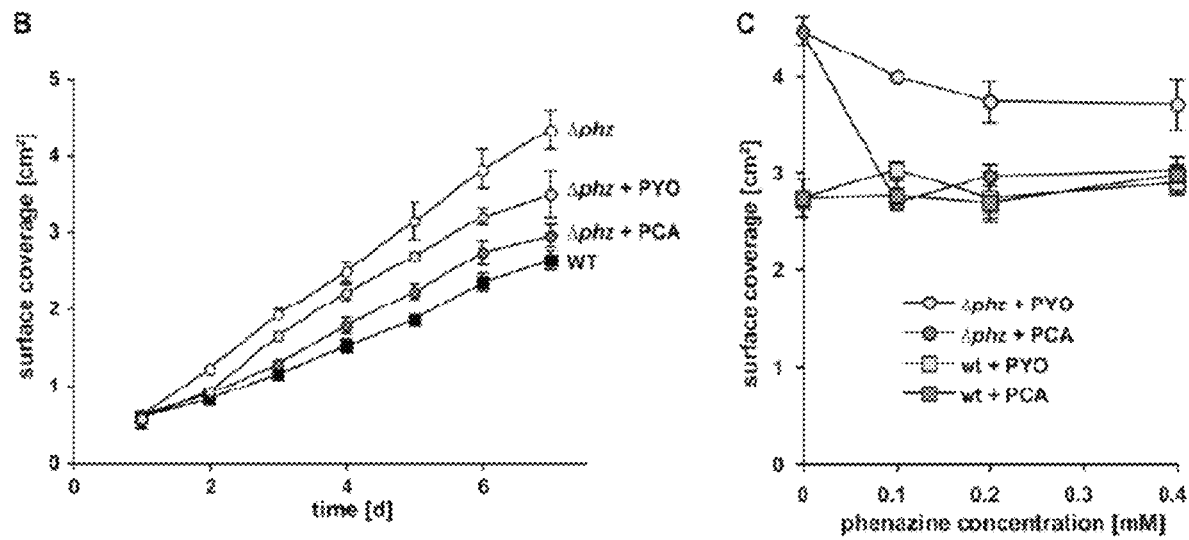

To determine whether the morphological trends that were observed in flow cells might translate to a larger scale, colony biofilms of the wild type and Δphz1/2 were grown. As reported previously, wild type PA14 formed smooth colonies that developed concentric ridges only after prolonged incubation (4 days; FIG. 8A) while Δphz1/2 formed wrinkled colonies that grew vertically within 2 days. Surface coverage by Δphz1/2 colonies was increased by up to 75% compared to wild-type colonies after 7 days (FIG. 8B). These features are consistent with an increased surface-to-volume ratio in the absence of phenazines, mirroring our findings for flow cell biofilms. PCA and pyocyanin were tested for their specific effects on surface coverage and rugosity by adding 0.2 M of either compound to the agar.

Both phenazines significantly decreased rugosity and surface coverage of Δphz1/2 colonies, while they did not noticeably affect the structure of wild-type colonies (FIG. 8A, B). Interestingly, PCA prevented colony spreading and the formation of wrinkles in Δphz1/2 colonies more efficiently than pyocyanin. A titration of phenazines showed that 0.1M PCA was sufficient to decrease surface coverage of Δphz1/2 colonies to wild-type levels (FIG. 8C), and higher concentrations of PCA (up to 0.4M) had no additional effects. In contrast, Δphz1/2 colonies still showed 50% increased surface coverage compared to wild-type colonies in the presence of 0.1 M pyocyanin. At pyocyanin concentrations of 0.2M or higher, Δphz1/2 covered 35% more of the agar surface than wild-type colonies. Therefore, the nature of the phenazine, in addition to the total amount of phenazine, is an important parameter influencing colony structure.

Figure 9:
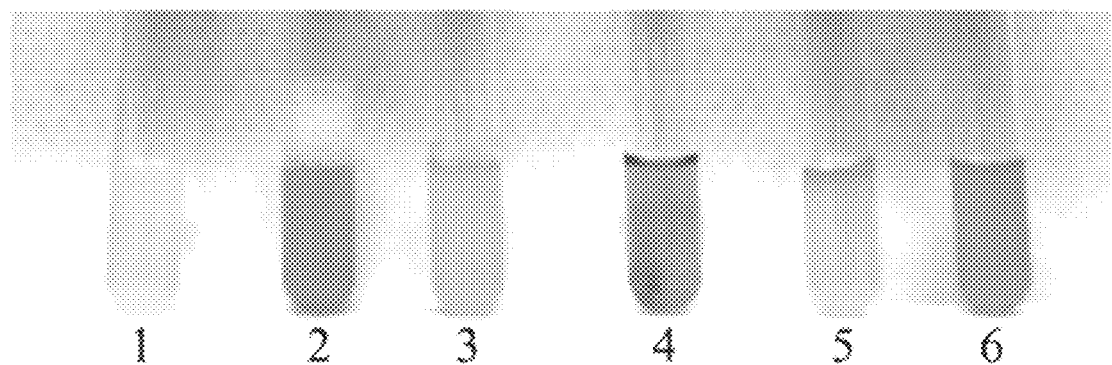
FIG. 9. Stationary-phase *P. aeruginosa* PA14 cultures produce pyocyanin and directly catalyze its reduction. (A) Tube 1, exponential-phase LB culture; tube 2, stationary-phase LB culture, immediately after removal from a shaking incubator; tube 3, stationary-phase LB culture, left standing at room temperature for ~5 minutes; tube 4, 100 μM pyocyanin in MOPS buffer, left standing at room temperature for ~5 minutes; tube 5 same culture as in tubes 2 & 3, resuspended in buffer shown in tube 4 and left standing at room temperature for ~5 minutes; tube 6, same suspension as in tube 5, after vortexing. (B) Absorbance spectra of buffer and supernatants from (A), tubes 4-6. The suspension from tube 5 was centrifuged and placed in a stoppered cuvette under anaerobic conditions. The pyocyanin/buffer spectrum overlaps almost completely with that of the supernatant from the aerated culture. PYO, pyocyanin.
Figure 9:
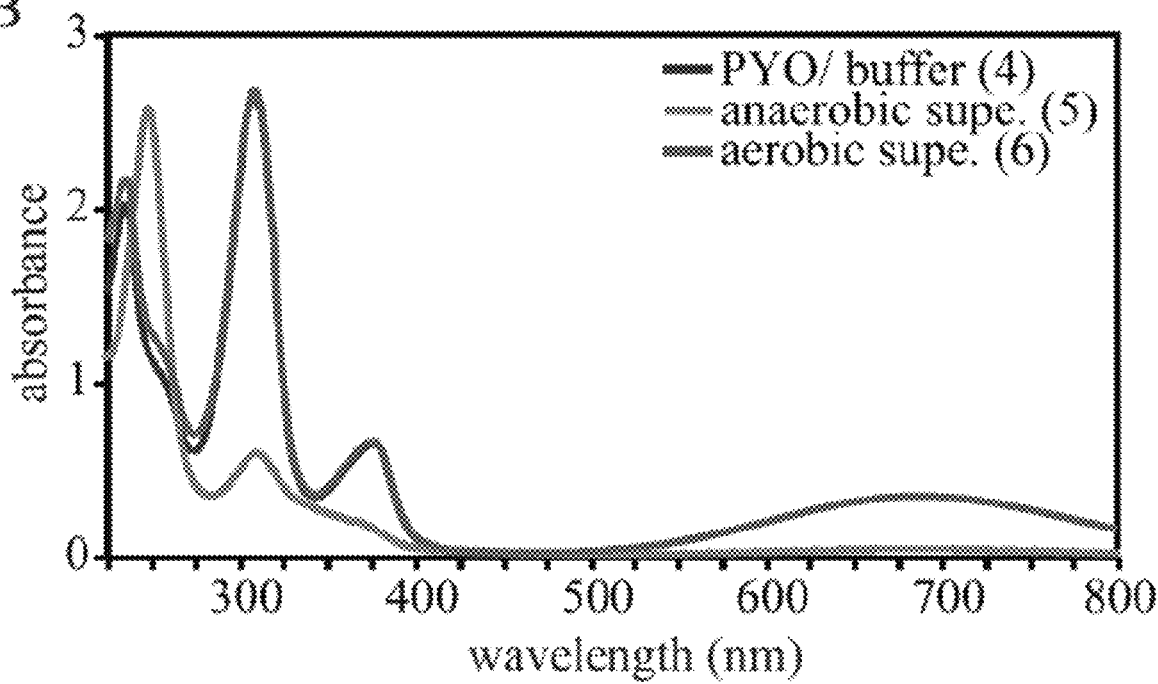

Example 7: The Effect of Phenazine in Promoting Survival of Bacterial Via Facilitating Intracellular Redox Balancing and Homeostasis Through Central Metabolic Pathways P. aeruginosa PA14 catalyzes pyocyanin reduction. Stationary-phase LB cultures of P. aeruginosa PA14 turn bright blue-green due to the production of the blue pigment pyocyanin specifically during this growth phase. P. aeruginosa PA14 also catalyzes the reduction of pyocyanin, a process that is readily observed when a stationary-phase culture is left standing without mixing or aeration by bubbling. Pyocyanin is converted from its blue (oxidized) form to a colorless (reduced) form. At the air-liquid interface, pyocyanin remains oxidized or becomes re-oxidized by an abiotic reaction with oxygen, but respiration by the bacteria creates a steep oxygen gradient just below this interface such that pyocyanin below a few millimeters remains colorless. A demonstration of this process is depicted in FIG. 9A (tube 3). A stationary-phase culture was centrifuged and the cell pellet was resuspended in a 100 μM solution of pyocyanin in MOPS buffer, the culture was allowed to sit without shaking for 5 minutes at room temperature. A gradient formed that resembled those observed for cultures in growth media. After vortexing, the entire suspension regained its original blue color (FIG. 9A, tubes 5 and 6). A filtrate from this suspension had the absorbance spectrum characteristic of pyocyanin in the oxidation state most stable under atmospheric conditions. When the culture was moved into an anaerobic chamber and a stoppered anaerobic cuvette was used to measure the absorbance spectrum of anaerobic culture filtrate, the sample showed decreased absorbance, indicating that pyocyanin had been reduced (FIG. 9B).

Example 8: Pyocyanin Reduction Rates Increase in Stationary Phase

Figure 10:
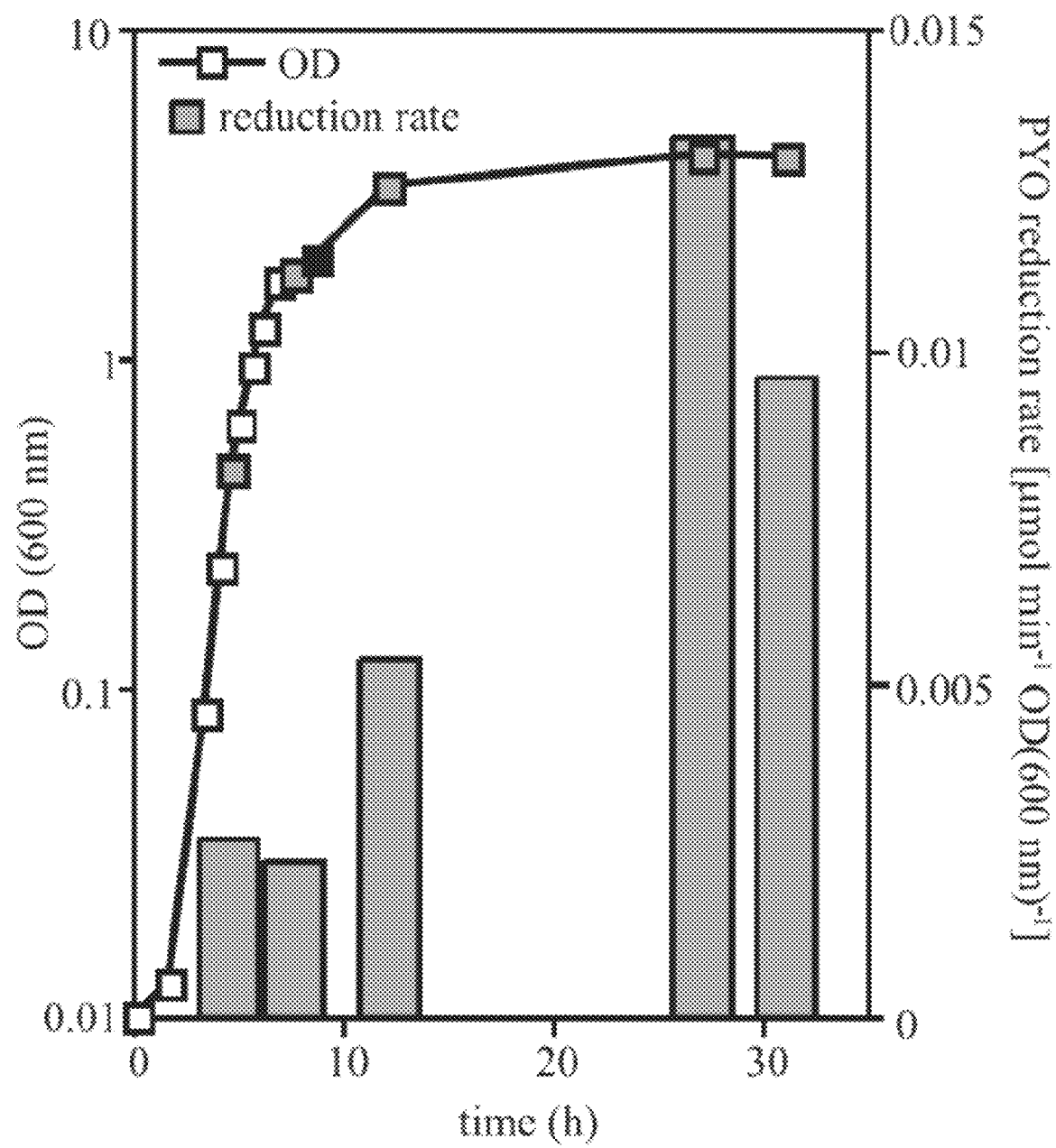
FIG. 10. The rate of pyocyanin reduction increases in stationary phase in P. aeruginosa PA14. A 100-ml P. aeruginosa LB culture was grown in a 500-ml Erlenmeyer flask and sampled at various points in the growth curve. Cells were concentrated or diluted in culture supernatant to normalize their OD (600 nm) to 0.8, amended with pyocyanin, then transferred to anaerobic cuvettes and stoppered. Absorbance at 690 nm was measured over time and was converted to the concentration of oxidized pyocyanin remaining in the cuvette. Gray squares indicate time points at which samples were taken for cell suspension assays. The black square indicates the first appearance of pyocyanin in the culture. Data shown is representative of three separate experiments. OD, optical density.

To quantify the rate of pyocyanin reduction by whole cells and test whether this process, like the biosynthesis of phenazines, was growth phase-dependent, LB culture at different stages of growth was sampled. Samples were diluted into their own supernatant, amended with pyocyanin, and transferred to an anaerobic cuvette. The decrease in oxidized pyocyanin absorbance was monitored over time for each sample, and a marked increase in the rate of pyocyanin reduction after the appearance of pyocyanin in stationary phase was observed. This result indicates that the rate of pyocyanin reduction by whole cells is growth-phase dependent (FIG. 10).

Example 9: Pyocyanin Exposure Balances the Intracellular Redox State

Strains of *P. aeruginosa* have been shown to vary in the timing and extent of phenazine production relative to the growth phase. The appearance of pyocyanin in wild type *P. aeruginosa* PA14 LB cultures correlates with entry into stationary phase and pyocyanin production plateaus in late stationary phase, reaching concentrations ranging from ~100 to 300 µM depending on the growth conditions (FIGS. 11A and 12C).

Given that NADH reacts with pyocyanin in vitro, one potential consequence of pyocyanin production and/or exposure would be a decrease in intracellular NADH levels. This is tested by growing cultures of *P. aeruginosa* wild type and a Δphz mutant (with in-frame deletions of both phenazine biosynthetic loci) and measuring intracellular NAD(H) approximately four hours after the onset of stationary phase. The intracellular NADH/NAD$^+$ ratio in the wild type was less than half that observed for the Δphz mutant. The growth curves for these cultures were virtually identical under the incubation conditions for this experiment. Addition of 90 µM oxidized pyocyanin (the approximate concentration of pyocyanin produced by wild type cultures under these conditions) to Δphz mutant cultures reduced the NADH/NAD$^+$ ratio to the wild type level (FIG. 11B). As a negative control, supernatant from the Δphz mutant was treated similarly and tested for an effect on intracellular NAD(H) concentrations; no difference was observed between cultures treated with "pyocyanin" preparations from the Δphz mutant and those treated with water. In titration experiments, an inverse relationship was found to exist between the concentration of pyocyanin added to a Δphz mutant culture and the NADH/NAD$^+$ ratio (FIG. 11C).

Figure 11:
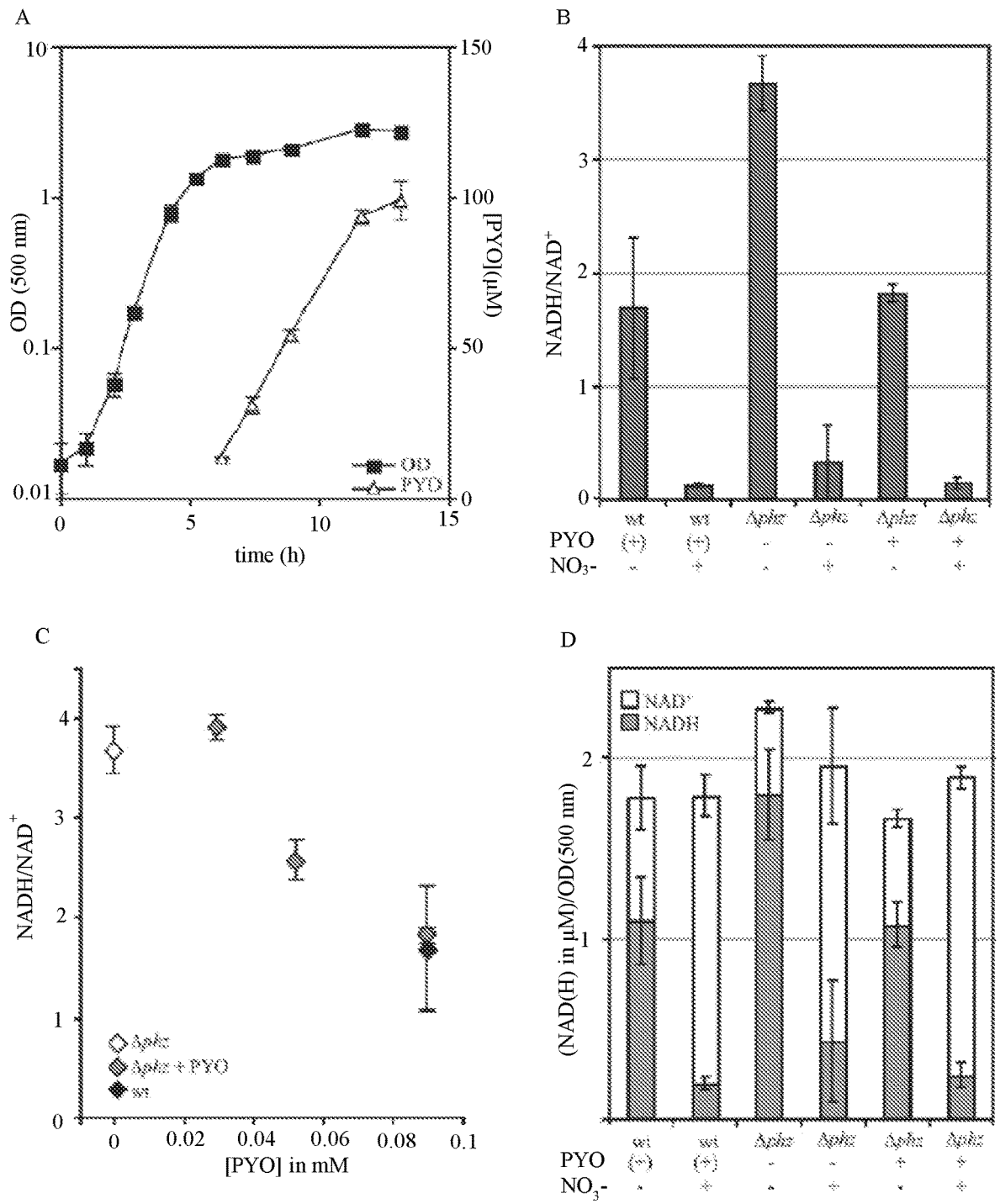
FIG. 11. Pyocyanin exposure effects redox balancing in stationary phase in a manner analogous to that of a known physiological electron acceptor. (A) Growth and pyocyanin production for wild type P. aeruginosa PA14 grown aerobically in 10 ml LB in 18×150 mM tubes. (B) NADH/NAD$^+$ ratios for cultures grown under the same conditions as those described in part (A). At 7 hours, pyocyanin production in the wild type cultures was visible by eye. 45 μM (half the expected final concentration) was added to the Δphz cultures to be tested for complementation, and 15 mM $KNO_3$ was added to cultures to be tested for the effect of an additional electron acceptor. At 9 hours, pyocyanin in the wild type cultures had increased to near-maximum concentrations, so a second dose of pyocyanin or $KNO_3$ was added to the appropriate cultures, for final concentrations of 90 μM and 30 mM, respectively. Water was added to negative controls. Eleven hours after inoculation, and 2 hours after the addition of the final dose of pyocyanin, NAD(H) was extracted and assayed for each culture. (C), NADH/NAD$^+$ ratios for cultures treated as in part (B), but with varying concentrations of pyocyanin added. (D) NADH and NAD$^+$ concentrations for cultures described in (B), normalized to OD (500 nm). Error bars represent the standard deviations of triplicate samples. OD, optical density. wt, wild type.
Figure 12:
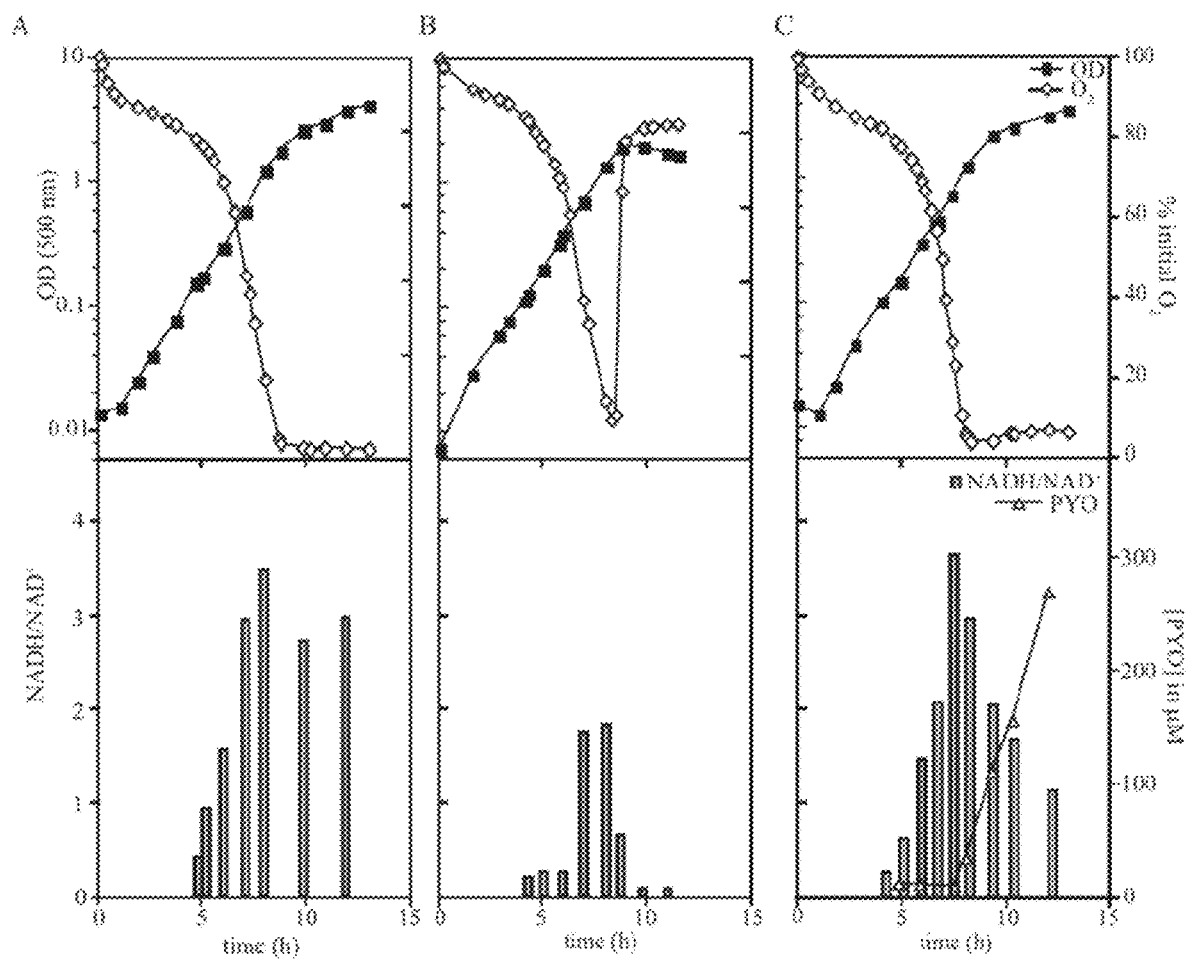
FIG. 12. NADH accumulates in stationary phase in cultures limited for oxygen and defective in pyocyanin production. P. aeruginosa wild type and Δphz cultures were grown in 1 L MOPS synthetic medium supplemented with either 50 or 10 mM glucose in a 3-L fermentor with constant aeration and agitation. Cultures were sampled at various points in the growth curve to allow measurement of the optical density (OD) at 500 nm and extraction of NAD(H). Relative dissolved oxygen concentrations were measured throughout growth using a polarographic oxygen electrode. OD (500 nm), $dO_2$, and NADH/NAD$^+$ are shown for (A), the Δphz mutant grown in medium containing 50 mM glucose, and (B) the Δphz mutant grown in medium containing 10 mM glucose. For (C), wild type P. aeruginosa PA14 grown in medium containing 50 mM glucose, these parameters plus the concentration of pyocyanin produced by the culture are shown.

To test whether the effect of pyocyanin is similar to that of a physiologically relevant terminal electron acceptor, 30 mM nitrate (a concentration sufficient to support growth of *P. aeruginosa* via anaerobic nitrate respiration) was added to a wild type culture, and nitrate with or without pyocyanin to Δphz mutant cultures in stationary phase (FIG. 11B). Nitrate and pyocyanin both effected decreases in intracellular NADH/NAD$^+$ ratios, apparently by catalyzing NADH oxidation, since decreases in absolute NADH concentrations correlated with increases in absolute NAD+ concentrations (FIG. 11D). Whereas pyocyanin effected a decrease when added in the micromolar range, nitrate did only when added at millimolar concentrations. Together, these results suggested that NADH can act as a source of electrons for pyocyanin reduction.

Example 10: The Intracellular NADH/NAD$^+$ Ratio is Influenced by the Relative Availability of Electron Donor and Acceptor The observation that other electron acceptors, i.e., pyocyanin and nitrate, decreased the NADH/NAD$^+$ ratio suggested that oxygen was limiting during stationary phase in the cultures. This could explain the accumulation of NADH four hours after the onset of stationary phase in the Δphz mutant (FIG. 11B). To confirm this, a batch culture of the Δphz mutant was grown in a fermentor, which allowed temperature and aeration controlling while simultaneously measuring dissolved oxygen in the culture. The culture was sampled at regular intervals to measure optical density and extract NAD(H). As predicted, oxygen levels decreased slowly until the culture reached mid- to late exponential phase, at which time it plummeted to zero. This drop in oxygen correlated with an increase in the intracellular NADH/NAD$^+$ ratio (FIG. 12A).

To test whether the drop in oxygen depended on the availability of electron donors for oxygen reduction, the experiment was repeated with added 20% of the glucose concentration in the medium compared to the medium in the initial experiment (10 mM versus 50 mM). When less electron donor was available, the oxygen concentration decreased in mid-exponential phase, but never reached zero and rapidly increased again upon entry into stationary phase (FIG. 12B). This culture never reached the same growth yield achieved by the culture containing 50 mM glucose, implying that the carbon source was the limiting factor that led it to enter stationary phase. The culture experienced oxygen limitation only transiently, if at all, due to the lower ratio of electron donor to electron acceptor in the experiment depicted in FIG. 12B compared to FIG. 12A. As a result, the NADH/NAD$^+$ ratio never reached the high level observed for the culture containing excess glucose.

Finally, the wild type strain in the presence of 50 mM glucose was tested, and sampled for pyocyanin concentrations in addition to NAD(H) and cell density. The wild type strain also exhibited increased NADH/NAD$^+$ ratios upon entry into stationary phase, and these ratios correlated with oxygen limitation. However, unlike the Δphz mutant, the wild type showed a decrease in intracellular NADH/NAD$^+$ that correlated with the appearance of pyocyanin in the culture. These results further support the hypothesis that pyocyanin can act as an alternate oxidant under conditions where the terminal electron acceptor for respiration has become limiting. This interpretation derives from the large difference in NADH levels observed between the wild type strain and Δphz after about 12 hours of incubation, and the correlation between decreasing NADH levels and increasing pyocyanin concentrations in culture filtrates observed upon entry into stationary phase (FIG. 12C).

Example 11: *P. aeruginosa* PA14 Excretes, and then Consumes, Pyruvate in Late Stationary Phase For fermentative organisms such as *E. coli* and *Propionibacterium freudenreichii*, the addition of the synthetic redox-cycling compound ferricyanide has been shown to alter carbon flux through central metabolic pathways. Particularly when the re-oxidation of this compound is coupled to electron transfer to an electrode, ferricyanide shifted the fermentation balance away from ethanol and propionate, products that require NADH for their formation, toward acetate, a more oxidized product. This implies that the ferricyanide acts as an electron shuttle from major pools of reductant inside the cell, such as NADH, to the electrode, thereby lessening the need for formation of more reduced fermentation products to dissipate cellular reductant.

To determine whether pyocyanin could play a similar role in *P. aeruginosa*, filtered culture supernatants was analyzed for small organic acids that are known fermentation products of *P. aeruginosa* metabolism. *P. aeruginosa* has been shown to ferment pyruvate under energy-starved conditions, converting it to lactate, acetate, and/or succinate. The production of lactate or succinate from pyruvate requires NADH as a substrate, while the conversion of pyruvate to acetate requires NAD$^+$. Therefore, the NADH/NAD$^+$ ratio in the wild type would be more favorable for acetate production, whereas the NADH/NAD$^+$ ratio in the Δphz mutant would favor production of lactate and succinate.

Figure 13:
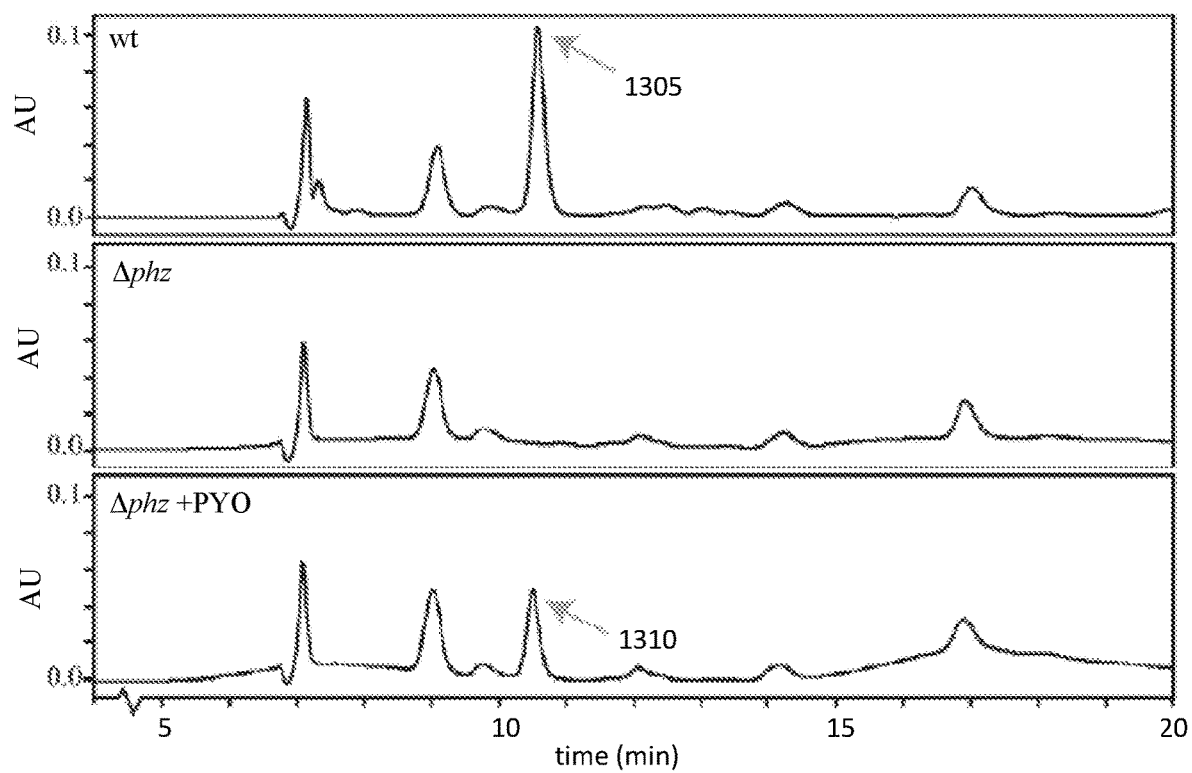
FIG. 13. Wild type P. aeruginosa PA14 excretes pyruvate in stationary phase, and addition of pyocyanin to Δphz mutant cultures restores the pyruvate excretion phenotype. Cultures were inoculated into MOPS synthetic medium amended with 50 mM glucose (initial OD (500 nm)=0.03). To complement pyruvate excretion, 50 μM pyocyanin was added to the Δphz culture at the time when pyocyanin reached its maximum concentration in the wild type cultures (approximately 12 hours after inoculation). 20 μl of culture filtrates at the 24-hour time point were loaded onto an anion exchange column and subjected to an isocratic gradient in 5 mM $H_2SO_4$. Pyruvate peaks (1305, 1310) are indicated by arrows. The elution time of pyruvate drifts slightly but averages around 10.5 minutes. Results shown are representative of three separate experiments. Other peak identities are described in the text.

Surprisingly, a marked difference was observed between the wild type and the Δphz mutant with respect to the production of pyruvate itself. In late stationary-phase (about 30 hours after inoculation) after growth in a defined medium with 50 mM glucose, pyruvate concentrations were observed as high as 6 mM in wild type culture filtrates (as indicated by a peak eluting at about 10.5 minutes), but any pyruvate in filtrates from Δphz mutant cultures was unable to detect. Adding pyocyanin to the Δphz mutant upon entry into stationary phase complemented the pyruvate excretion phenotype (FIG. 13), although incompletely because only about half the final concentration of pyocyanin produced by the wild type under these conditions was added (50 vs. 100 µM). Citrate, lactate and acetate in both wild type and Δphz mutant culture filtrates were also detected at similar concentrations, eluting at −9.1, 14.3 and 17.0 minutes, respectively. The peak eluting at 7.1 minutes was the MOPS buffer from the medium. The compounds represented by the peaks eluting at approximately 7.3 minutes (wild type filtrate only), and 9.9 and 12.2 minutes (both wild type and Δphz mutant filtrates) were not identified. Standards containing 2-oxoglutarate and malate were run with the same method, but did not co-elute with any of these peaks.

Figure 14:
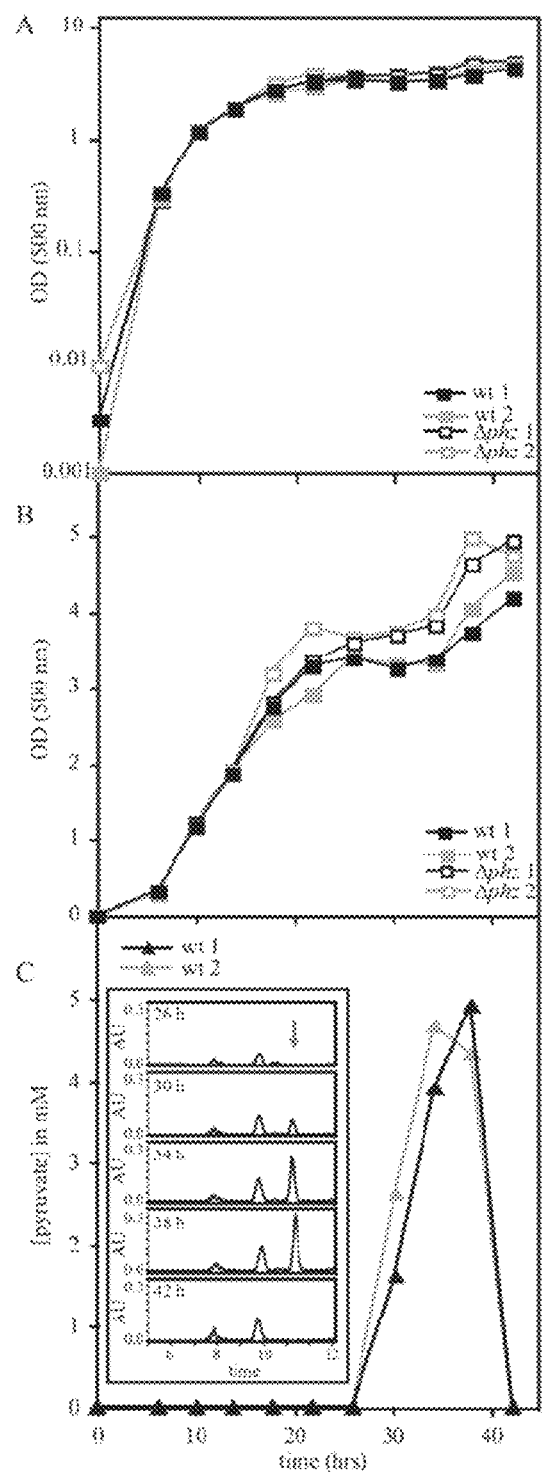
FIG. 14. P. aeruginosa PA14 cultures consume excreted pyruvate in very late stationary phase. Duplicate cultures were inoculated at OD (500 nm)~0.001 in MOPS synthetic medium amended with 50 mM glucose. Approximately every 4 hours, 100-200 μl culture were sampled and filtered for HPLC analysis as described for FIG. 4. (A), OD 500 for wild type and Δphz cultures plotted on a logarithmic scale. (B), same data as in (A) plotted on a linear scale to show the lower growth yields consistently observed for wild type PA14 under this condition. (C) Quantification of pyruvate production for the "wt 1" and "wt 2" cultures, and inset, chromatograms demonstrating the disappearance of pyruvate at 42 hours for the "wt 1" culture. The arrow indicates the elution time of the pyruvate peak. wt, wild type.

To better constrain the timing of metabolite excretion in the wild type and Δphz mutant, duplicate cultures were sampled every 4 hours over the course of approximately 30 hours in stationary phase (FIG. 14). Pyruvate appeared at detectable levels in wild type cultures between 22 and 26 hours after inoculation, and had increased to ~5 mM after 38 hours. However, by the 42-hour time point, the pyruvate in both replicates had decreased to levels below the detection limit (~0.05 mM) (FIG. 14C). Abiotic degradation of pyruvate generates a peak eluting at approximately 8 minutes, which does not co-elute with any of the peaks observed in traces from our culture filtrates (data not shown). Therefore, the disappearance of the pyruvate peak at the 42-hour time point implied that it had been metabolized by the bacteria.

Another phenotype that became apparent under these growth conditions was the reproducible difference in cell yields between wild type and Δphz mutant cultures. The optical densities of wild type cultures were typically lower than those of the Δphz mutant cultures in stationary phase, a phenotype that becomes more apparent when the optical density is plotted on a linear scale (FIGS. 14A and 14B).

Example 12: Pyruvate Fermentation Facilitates Survival in Energy-Starved *P. aeruginosa* PA14 Cultures Recently, Schobert and colleagues have characterized genes implicated in a pyruvate fermentation pathway in *P. aeruginosa* strain PAO1. In this pathway, pyruvate is converted by multiple enzymes to succinate, acetate, and/or lactate. These reactions were probably responsible for the consumption of pyruvate in late stationary phase in the cultures, because these compounds are detectable by the analytical HPLC method, and their concentrations increase was not observed as pyruvate. Therefore, it is hypothesize that pyruvate was completely oxidized through the utilization of the small amount of oxygen available to the cells. However, in environments with steep gradients of electron acceptor availability, such as those encountered in surface-attached or aggregated bacterial communities, excreted pyruvate may be utilized for substrate-level phosphorylation when respiratory electron acceptors become limiting. To verify that *P. aeruginosa* strain PA14 can utilize pyruvate for survival under strict anaerobic conditions, the wild type and an ldhA mutant, defective in the ability to reduce pyruvate to lactate, were incubated in stoppered serum bottles containing buffered LB amended with 20 mM pyruvate. Wild type culture with no pyruvate was set up as a control. Colony-forming units in samples from these cultures were monitored over more than three weeks, and showed that, a mutant with a disruption in the gene ldhA was defective in survival on pyruvate. The decline of this mutant was similar to that of the wild type culture containing no added pyruvate. *P. aeruginosa* PA14 is therefore also able to survive under conditions of energy starvation through utilization of a lactate dehydrogenase-dependent pathway for pyruvate fermentation.

Figure 15:
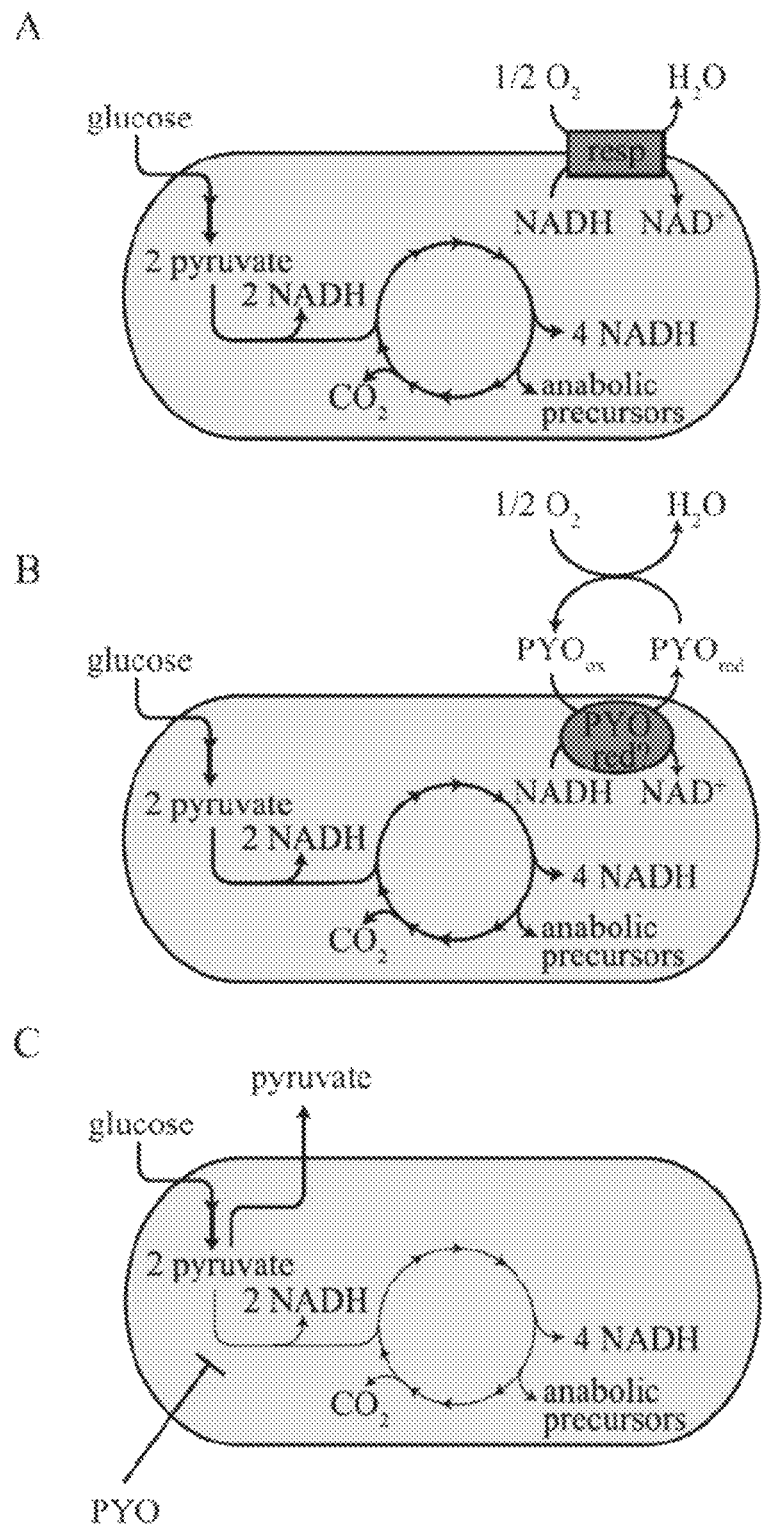
FIG. 15. Model: pyocyanin reduction allows P. aeruginosa PA14 to maintain redox homeostasis under oxygen-limited conditions. When sufficient oxygen is available for growth (A), the aerobic respiratory chain ("resp") can catalyze the reoxidation of NADH. Under conditions in which terminal electron acceptors for respiration are limiting (B), P. aeruginosa can couple the re-oxidation of NADH to the reduction of pyocyanin, either directly or through an enzyme-mediated reaction as represented by "pyocyanin red," a putative phenazine reductase. The electrons could be transferred from pyocyanin to oxygen through an abiotic extracellular reaction. (C) Also under conditions of oxygen limitation, the NADH/NAD$^+$ ratio could be balanced through inactivation of the pyruvate dehydrogenase complex by pyocyanin. NAD+ reduction (and therefore NADH production) would be avoided because pyruvate would be excreted without further oxidation.

Example 13 A Model for Pyocyanin Reduction Allows *P. aeruginosa* PA14 to Maintain Redox Homeostasis Under Oxygen-Limited Conditions When sufficient oxygen is available for growth (FIG. 15A), the aerobic respiratory chain ("resp") can catalyze the reoxidation of NADH. Under conditions in which terminal electron acceptors for respiration are limiting (FIG. 15B), *P. aeruginosa* can couple the reoxidation of NADH to the reduction of pyocyanin, either directly or through an enzyme-mediated reaction as represented by "pyocyanin red," a putative phenazine reductase. The electrons could be transferred from pyocyanin to oxygen through an abiotic extracellular reaction. (FIG. 15C) Also under conditions of oxygen limitation, the NADH/NAD$^+$ ratio could be balanced through inactivation of the pyruvate dehydrogenase complex by pyocyanin. NAD$^+$ reduction (and therefore NADH production) would be avoided because pyruvate would be excreted without further oxidation.

Example 14: The Effect of Phenazine in Promoting Anaerobic Survival of Bacteria Under Conditions of Oxidant Limitation Antibiotics are increasingly recognized as having other, important physiological functions for the cells that produce them. An example of this is the effect phenazines have on signaling and community development for *Pseudomonas aeruginosa*. Phenazine-facilitated electron transfer to poised-potential electrodes promotes anaerobic survival but not growth of *Pseudomonas aeruginosa* PA14 under conditions of oxidant limitation. Other electron shuttles that are reduced but not made by PA14 do not facilitate survival, suggesting the survival effect is specific to endogenous phenazines. Examples are shown in the enclosed paper: Wang et al., 2010, Endogenous phenazine antibiotics promote anaerobic survival of *Pseudomonas aeruginosa* via extracellular electron transfer (J. Bacteriology, vol. 192, No. 1, page 365-369).

Examples 15: Identification of Phenazine-Degrading Bacterial Strains that Produce Phenazine Degrading Enzymes Bacteria that degrade phenazines has been isolated and identified. For example, a new phenazine-degrading strain was isolated that preliminary 16S rDNA sequencing results suggest is closely related to *Mycobacteria* and *Streptomyces* species. This bacterium was isolated on minimal medium using PCA as the sole carbon source. The relationship between bacterium growth and PCA degradation suggested that the bacterial strain could use phenazines as the sole source of carbon and nitrogen and was able to completely degrade PCA in a short time.

Isolation of additional novel phenazine degraders is expected to be performable by using a similar method: construct an "enrichment culture" by defining a minimal growth medium where a phenazine (PCA, PYO, etc. . . . ) is provided as either (or both) the sole source of carbon or nitrogen. If growth is observed after many rounds of serial dilutions, phenazine-degraders can be isolated by plating the enrichment culture on an agar plate with the same medium composition. Single colonies are picked, and streaked on fresh plates, and visually checked for purity. Once pure, the 16S rDNA is sequenced and the organism can be phenotypically characterized.

Another example of phenazine degrading bacterial strains is provided in the paper: Yang, Z-J et al., 2007, "Isolation, identification, and degradation characteristics of phenazine-1-carboxylic acid-degrading strain *Sphingomonas* sp. DP58". Current Microbiology. 55:284-287, herein also incorporated by reference in its entirety.

Example 16: Correlation Between Elevated Phenazine Concentrations and the Decline of Pulmonary Function To determine the relationship of FEV1% to phenazine concentrations, forty-seven participants were recruited during scheduled visits to Children's Hospital of Boston (CHB). Inclusion criteria were a diagnosis of CF based on genotyping and sweat chloride testing and chronic *P. aeruginosa* infection (positive culture >1 year). Sputum samples were obtained from each patient by expectoration. Samples were stored on ice and processed within 4 hours of expectoration. Sputum was sheared through a syringe and homogenized in an equal volume of 1 mM Sputolysin for 30 minutes.

Homogenized sputum was centrifuged and supernatants were filtered through filter centrifuge columns and phenazine content was quantified by HPLC as described in Dietrich et al (Molecular Microbiology, 2006. 61(5): p. 1308-1321).

FEV1% values were determined by spirometry as described in Knudson et al., Am Rev Respir Dis 1976; 113:587-600. In particular, a cross sectional analysis of sputum pyocyanin concentrations reveals a positive correlation with pulmonary function decline (FEV1%) as illustrated in FIG. 16A.

One method to detect whether Fe(II)/Fe(III) chelation and/or inhibition of phenazine-mediated iron acquisition is successful, is to use a direct imaging approach. For example, the hybridization chain reaction (Choi et al., "Programmable in situ amplification for multiplexed imaging of mRNA expression" Nature Biotechnol., 2010) can be used to detect gene expression at high resolution at the single cell level.

As an example, using genes such as bqsS and bqsR (Kreamer et al., J. Bacteriol, 2011, 194, 1195-1204), which encode a two-component signal transduction system that is upregulatedspecifically in response to ferrous iron [Fe(II)], detecting the expression of these genes (or lack thereof) within lung samples, including expectorated sputum, could be used as a direct indicator of the inhibition of phenazine-mediated pathways, including iron acquisition.

Figure 16:
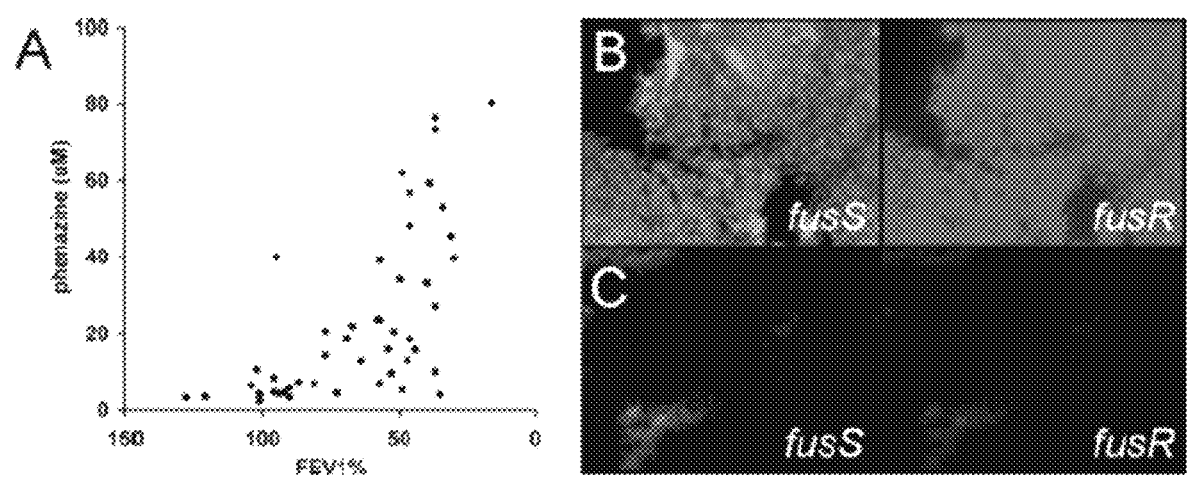
FIG. 16. A) Cross-sectional analysis of sputum pyocyanin concentrations reveals a positive correlation with pulmonary function decline (FEV1%). Hybridization chain reaction imaging of (B) wild type P. aeruginosa and (C) a mutant containing a deletion of bqsR, reveals differential gene expression patterns of the genes bqsS (green) and bqsR (red) in response to 50 μM Fe(II) (left) and no treatment (right).

Reference is made to hybridization chain reaction imaging of wild type *P. aeruginosa* and a mutant containing a deletion of bqsR, illustrated in FIG. 16B and FIG. 16C. The result reveal differential gene expression patterns of the genes bqsS (green) and bqsR (red) in response to 50 μM Fe(II) (left) and no treatment (right) (FIG. 16B and FIG. 16C)

Example 17: The Phenazine Pyocyanin is a Terminal Signaling Factor in the Quorum Sensing Network of *Pseudomonas aeruginosa*

Using *Pseudomonas aeruginosa* DNA microarrays and quantitative RT-PCR, it is demonstrated that the phenazine pyocyanin elicits the upregulation of genes/operons that function in transport [such as the resistance-nodulation-cell division (RND) efflux pump MexGHI-OpmD] and possibly in redox control (such as PA2274, a putative flavin-dependant monooxygenase), and downregulates genes involved in ferric iron acquisition. Strikingly, mexGHI-opmD and PA2274 were previously shown to be regulated by the PA14 quorum sensing network that controls the production of virulence factors (including phenazines). Through mutational analysis, it is shown that pyocyanin is the physiological signal for the upregulation of these quorum sensing controlled genes during stationary phase and that the response is mediated by the transcription factor SoxR. Our results implicate phenazines as signaling molecules in both *P. aeruginosa* PA14 and PAO1. Examples are shown in the paper: Dietrich et al. 2006, The phenazine pyocyanin is a terminal signaling factor in the quorum sensing network of *Pseudomonas aeruginosa*, Molecular Microbiology Vol. 61, No. 5, page 1308-1321, incorporated herein by reference in its entirety.

Example 18: PCA Degradation Using Isolate DKN1213

Soil samples were inoculated into a minimal salts liquid medium with ~5 mM PCA provided as the sole carbon source. After 1 week of incubation at 30 C, a 10% inoculum was introduced into a fresh batch of the same medium with PCA again serving as the carbon source. After an additional round of enrichment, 100 uL of the enrichment culture were spread upon an agar petri dish made of the same medium+5 mM PCA. After a week's time, single colonies were picked and re-streaked to the same agar medium for purification, as well as to an LB plate. After several more rounds of streaking to verify purify, a single colony was picked and grown up in minimal medium+PCA. This sample was cryopreserved, and became the standard reference culture for later experiments (named DKN1213).

16s rRNA sequencing was performed on DKN1213, revealing it to be closely related to strains of fast growing *Mycobacteria*, as well as to *Streptomyces*. When DKN1213 was grown in LB broth+4 mM PCA, degradation of over 1 mM PCA was measured in less than a week, indicating that it contains an enzyme capable of degrading PCA, as well as a system for transporting PCA into the cell. Similar enrichment and isolation methods are expected to be suitable to enrich other novel forms of PCA degraders. Instead of providing PCA as the carbon source, PCA can be provided as the nitrogen source, or as both the carbon and nitrogen source. Analogously, other phenazines are expected to be used to enrich for phenazine-degrading bacteria in the same way as described for PCA.

Further work to identify the enzyme responsible for degrading PCA can be performed with DKN1213. A biochemical approach is expected to require that an activity assay be developed for PCA degradation. This is expected to be based on following either the absorption or fluorescence of PCA over time, and purifying cell fractions that promote its disappearance. A genetic approach is expected to employ transposon mutagenesis to make a collection of random mutants and screen them for the inability to grow on a minimal medium+PCA. Once an enzyme is identified, its specificity can be altered using directed evolution, so as to change the spectrum of phenazines it could recognize or improve its efficiency.

Example 19: Fe(II)/Fe(III) Combination Therapy for Cystic Fibrosis Patients

The abundance of Fe(II) in the lungs of cystic fibrosis patients has important implications for the design of novel antimicrobial therapies.

Competition between pathogens and their hosts for ferric iron [Fe(III)] has been extensively studied due to iron's critical importance in pathogenesis [44]. While microbial ferrous iron [Fe(II)] uptake pathways are known [45], therapeutic strategies designed to limit iron availability have only targeted Fe(III) because it is commonly assumed to be the dominant physiologically relevant form.

For example, Fe(III) chelation has been shown to dramatically improve antibiotic effectiveness against the opportunistic pathogen *Pseudomonas aeruginosa* in aerobic environments, and is being explored as a means to combat biofilm infections of cystic fibrosis (CF) patients [46-49]. Based on the results obtained by this approach in vitro, it is expected that if it is to be similarly effective in vivo, iron would need to remain in its oxidized state [Fe(III)] as infections progress.

However, in late stages of CF infections, localized hypoxic microenvironments exist [50] which could stabilize Fe(II). Furthermore, *P. aeruginosa* produces redox-active phenazines in CF sputum [51] that can reduce Fe(III) to Fe(II) and circumvent Fe(III)-chelation in vitro [52].

Ferric iron [Fe(III)] chelation has been shown to combat pathogenic microbial biofilms in vitro, and has been proposed as a novel treatment for cystic fibrosis (CF) patients. However, the success of this approach assumes an abundance of Fe(III) in the infected environment. Here we show that appreciable levels of ferrous iron [Fe(II)] exist in the majority of CF lungs, that Fe(II) compromises Fe(III) chelation therapy under anaerobic conditions, and that Fe(III) and Fe(II) chelators can act synergistically to prevent or disrupt biofilm growth.

In particular, Examples 20-22 (below) show that Fe(II) can be abundant at infection sites, and its concentration was measured in CF sputum from patients at different stages of lung function decline. While total iron has been quantified previously [53], this is the first report of its oxidation state in vivo.

Example 20: Demonstration of the Presence of Fe(II) in Sputum of Cystic Fibrosis Patients Twenty-five participants with cystic fibrosis (CF), aged 7 to 20, were recruited during scheduled visits to Children's Hospital Los Angeles (CHLA). Study inclusion criteria were a positive diagnosis of CF, ability to expectorate sputum and informed consent/assent. Disease severity was determined by FEV1% scores using published guidelines [55]. CHLA and the California Institute of Technology approved the study protocols (CCI-10-00232).

A total of 116 sputum samples from 25 patients were immediately flash frozen upon expectoration and moved to an anaerobic chamber for analysis. Samples were homogenized and ratios of Fe(II)/Fe(III) concentrations were determined using the Ferrozine® assay. Total iron levels were confirmed using ICP-MS and increased significantly as lung function worsened (FIG. 17 Panel A). In most patients, a notable proportion of total iron was Fe(II) (>19%), though it was appreciably higher (>37%) in subjects with mild to severe pulmonary obstruction. That such high concentrations of Fe(II) are observed at all stages of infection is striking, and reinforces the need to better understand the mechanisms of iron homeostasis in the lung environment [54].

Example 21: Demonstration of Synergistic Effect of Fe(II) and Fe(III) Chelators on Bacterial Biofilms Because the abundance of Fe(II) in infected environments of lungs of CF patients may compromise the success of Fe(III)-specific chelation therapies, the question of whether a combination of Fe(III) and Fe(II) chelators would be more effective than Fe(III) chelators alone was investigated. An anaerobic, high-throughput biofilm assay was used to determine whether Ferrozine®, an Fe(II)-specific chelator, could act synergistically with conalbumin, an Fe(III) chelator, to prevent *P. aeruginosa* biofilm formation (FIG. 17 Panel B). Neither compound affected planktonic growth rates. Contrary to aerobic observations [46,47], 100 μM conalbumin was also ineffective in preventing biofilm growth under anaerobic conditions where ~10 μM Fe(II) and 10 μM Fe(III) were present. In contrast, 100 μM Ferrozine® reduced biofilm accumulation by 24% and 200 μM Ferrozine® reduced it slightly further. Strikingly, the combination of 100 μM conalbumin and 200 μM Ferrozine® reduced biofilm accumulation by 54%. To determine whether this effect was due to iron sequestration rather than non-specific interactions, Fe(II) in excess of the chelation capacity was added. Under these conditions, biofilm growth was restored. Iron not only signals biofilm formation, but is involved in biofilm maintenance [49].

Example 22: Demonstration of Synergistic Effect of Fe(II) and Fe(III) Chelators on Mature Bacterial Biofilms Because iron not only signals biofilm formation, but is involved in biofilm maintenance [49], similar mixed Fe(II)/Fe(III) chelation experiments targeting mature biofilms (FIG. 17 Panel B) were performed. Conalbumin did not significantly reduce established biomass, but ~20% dissolution was observed in the presence of 100 or 200 μM Ferrozine®. Together with conalbumin, Ferrozine® promoted even more dissolution, yet biomass was maintained at high levels in the presence of excess Fe(II). Collectively, the results of Examples 20-22 indicate that as lung function declines and Fe(II) concentrations rise, targeting both oxidation states will be more effective than targeting Fe(III) alone.

These results highlight that the chemistry of infected environments can be used gain a clear picture of what pathogens are experiencing. This can be particularly important because pathways that may be crucial for survival in vivo may not be the same as those required for survival under standard laboratory conditions. Because the environment of infections is dynamically responsive to changes in both the microbial community and the host, and is likely heterogeneous on the microscale, a more thorough understanding of its composition in time and space can inform the design of therapeutics. These results demonstrate the potential for environmentally-informed rational drug design.

In summary, in several embodiments provided herein are methods and systems for interfering with viability of bacteria and related compounds and compositions. In particular, in view of above, interfering with viability of bacteria can be performed in vivo or in vitro by inactivating a phenazine and/or one or more phenazine related pathways in the bacteria to reduce survivability and/or antibiotic resistance of the bacteria according to several approaches. as will be understood by a skilled person.

According to a first approach, inactivating a phenazine and/or one or more phenazine related pathway can be performed by inhibiting synthesis of the phenazine in the bacteria. In particular according to the first approach the inhibiting can be performed by interfering with quorum sensing of the bacteria, by reducing the amount of phenazine in the bacteria and/or by inhibiting transcription and/or translation of the phenazine biosynthetic genes. According to the first approach the inhibiting and/or the reducing can be performed by inactivating one or more proteins involved in phenazine biosynthesis which can in particular comprise acyl homoserine lactones and the *pseudomonas* quinolone signal (PQS). According to the first approach, the reducing can be performed by enhancing phenazine degradation endogenously and/or exogenously and/or by modifying the phenazines, for example chemically, to inhibit and in particular prevent phenazine uptake by the bacteria. According to the first approach enhancing phenazine degradation can be performed by expressing and/or delivering a protein that degrades phenazines.

According to a second approach which can be performed in addition or in alternative with the first approach, inactivating a phenazine and/or one or more phenazine related pathway can be performed by inhibiting transportation of phenazines in and/or out of the bacterial cell. According to the second approach, the inhibiting can be performed by inhibiting and in particular, blocking one or more phenazine exporters of the bacteria, such as RND efflux pumps of the mexGHIopmD variety and when the bacterium is *Pseudomonas aeruginosa*, one or more phenazine exporters are encoded by PA4205, PA 4206, PA 4207 and/or PA4208. According to the second approach, the inhibiting can also be additionally or alternatively performed by inhibiting an in particular blocking a protein involved in modifying phenazines in a phenazine modified form to be recognized by a phenazine exporter of the bacteria. According to the second approach, the inhibiting can also be additionally or alternatively performed by inhibiting is performed by inhibiting and in particular blocking one or more MFS transporters involved in phenazine import/export of the bacteria, such as when the bacterium is *Pseudomonas aeruginosa*, one or more MFS transporters are encoded for example by PA3718 and/or PA4233.

According to a third approach which can be performed in addition or in alternative with the first approach and/or second approach, inactivating a phenazine and/or one or more phenazine related pathway can be performed by providing the bacteria with one or more phenazine degrading enzymes, such as phenazine degrading enzymes produced by phenazine-degrading bacteria strains and additional enzymes and compounds identifiable by a skilled person.

According to a fourth approach which can be performed in addition or in alternative with the first approach, second approach and/or third approach, inactivating a phenazine and/or one or more phenazine related pathway can be performed by converting at least a portion of the phenazine of the bacteria in an inactive form. According to the fourth approach converting at least a portion of the phenazine of the bacteria in an inactive form can be performed by inhibiting intracellular reduction and/or extracellular oxidation of phenazines of the bacteria, and/or by modifying phenazines chemically to interfere with phenazine uptake and/or intracellular processing of bacteria.

In any one of the first, second, third and fourth approaches the one or more phenazine related pathways can comprise phenazine-mediated bacterial biofilm development in the bacteria and/or phenazine-mediated iron acquisition of bacteria. In particular, in any one of the first, second, third and fourth approaches inactivating phenazine-mediated iron acquisition of bacteria can be performed by inhibiting phenazine-mediated Fe (III) reduction to Fe (II), and/or by inhibiting Fe (II) acquisition of bacteria. In any one of the first, second, third and fourth approaches, inhibiting Fe (II) acquisition of bacteria can be performed by inhibiting a cytoplasmic membrane Fe (II) transporter of bacteria, such as the Fe (II) transporter is the cytoplasmic membrane protein FeoB or a homologues protein thereof. In any one of the first, second, third and fourth approaches inactivating phenazine-mediated iron acquisition of bacteria can be performed by activating a Fe (II) chelator in the bacteria, and in particular a Fe (II) chelator in the form of a protein and/or a chemical compound. In any one of the first, second, third and fourth approaches the Fe (II) chelator can be Ferrozine®, and the activating can be performed for example by delivering Ferrozine® into the mucus environment of bacteria using an aerosol. In any one of the first, second, third and fourth approaches the Fe (II) chelator is a host protein activating a Fe (II) chelator comprises regulating of one or more host genes encoding a host Fe (II) chelator.

In any one of the first, second, third and fourth approaches the one or more phenazine related pathways can comprise a phenazine-mediated signaling pathway of the bacteria, such as a signaling pathway triggers a transition from the motile to the sessile state in bacteria having a motile and a sessile state. In any one of the first, second, third and fourth approaches, inactivating a phenazine-mediated signaling pathway can be performed by inactivating one or more signaling molecules (e.g. one or more proteins) in the phenazine mediated signaling pathway, and in particular by inactivating direct or indirect effectors of phenazines in the pathway, acyl homoserine lactones and/or the *pseudomonas* quinalone signal (PQS). In any one of the first, second, third and fourth approaches inactivating the one or more signaling molecules is performed by inhibiting expression of one or more genes in the bacteria coding for signaling molecules in the pathway.

In any one of the first, second, third and fourth approaches the one or more phenazine related pathways comprise phenazines related pathways forming central metabolic pathways of the bacteria.

In any one of the first, second, third and fourth approaches the one or more phenazine related pathways comprise intracellular phenazine mediated redox hemostasis of the bacteria, e.g. by inhibiting phenazine-mediated electron shuttling of the bacteria.

In any one of the first, second, third and fourth approaches the one or more phenazine related pathways comprise transportation of phenazines in and/or out of the bacterial cell.

In any one of the first, second, third and fourth approaches the bacterium is *Pseudomonas aeruginosa*.

In any one of the first, second, third, and fourth approaches, the approach further comprises degrading phenazines in vivo and/or in vitro.

In any one of the first, second, third and fourth approaches a system for interfering with viability of bacteria according to the approach can comprise one or more agents able to inactivate a phenazine and/or a phenazine related pathway in the bacteria for simultaneous combined or sequential use in any one of the methods and approaches herein described, optionally together with an antibiotic and/or other antimicrobial.

According to a fifth approach, inactivating a phenazine and/or one or more phenazine related pathway can be performed in a method for treating and/or preventing a bacterial infection in an individual, the method comprising administering an effective amount of one or more agents able to specifically inactivate phenazine and/or a phenazine related pathway in the bacteria optionally together with administering an antibiotic and/or an additional antimicrobial to the individual. According the fifth approach inactivation of phenazine can be performed according to any one of the first, second, third and fourth approached wherein inactivation is selective to the phenazine and/or the one or more phenazine related pathways of the bacteria. According to the fifth approach a system for treating and/or preventing a bacterial infection in an individual, can comprise one or more agents able to selectively inactivate a phenazine and/or a phenazine related pathway in the bacteria and optionally an antibiotic and/or other antimicrobial, for simultaneous combined or sequential use in any one of the methods according to the fifth approach.

According to a sixth approach, inactivating a phenazine and/or one or more phenazine related pathway can be performed in a method for identifying an antimicrobial, comprising contacting a microbe with a candidate agent and detecting the ability of the candidate agent of inactivating a phenazine and/or a phenazine related pathway in the bacteria. According to the sixth approach, the method can further comprise contacting the microbe with an antibiotic and/or an additional antimicrobial to the individual. According to the sixth approach, inactivation of phenazine is performed according to any one of the first, second, third, fourth or fifth approaches wherein inactivation is selective to the phenazine and/or the one or more phenazine related pathways of the bacteria. According to the sixth approach, a system for identifying an antimicrobial, can comprise one or more microbe and one or more agents capable of detecting phenazine and/or phenazine related pathways for simultaneous combined or sequential use in methods and systems according to any one of the first, second, third, fourth and fifth approach.

According to a seventh approach, inactivating a phenazine and/or one or more phenazine related pathway can be performed by an antimicrobial comprising one or more agents able to inactivate a phenazine and/or a phenazine related pathway in the bacteria to reduce antibiotic resistance and/or survivability of bacteria and optionally a compatible vehicle for effective administrating and/or delivering of the one or more agents to an individual. In particular, according to the seventh approach, the one or more agents are agents capable of interfering with viability of bacteria in the method and systems according to any one of the first, second, third, fourth and fifth approach. According to the seventh approach, the antimicrobial can further comprise an antibiotic and/or an additional antimicrobial.

According to the seventh approach, the vehicle can be a pharmaceutically acceptable vehicle and the composition is a pharmaceutical composition.

According to an eighth approach, inactivating a phenazine and/or one or more phenazine related pathway can be performed in a method to inactivate a bacterium in vitro or in vivo, the method comprising contacting the bacterium with one or more agents capable of inactivating a phenazine and/or a phenazine related pathway in the bacterium in combination with one or more antibiotic and/or other antimicrobial. According to the eighth approach, the one or more agents are agents capable of interfering with viability of bacteria in the method and systems according to any one of the first, second, third, fourth and fifth approach. According to the eighth approach, the one or more agents can be able to selectively inactivate the phenazine and/or phenazine related pathway in the bacterium. According to the eighth approach, a system for inactivating a bacterium in vitro or in vivo, can comprise one or more agents able to selectively inactivate a phenazine and/or a phenazine related pathway in the bacteria and optionally an antibiotic and/or other antimicrobial, for simultaneous combined or sequential use in the method and systems according to any one of the first, second, third, fourth and fifth approach.

According to a ninth approach, inactivating a phenazine and/or one or more phenazine related pathway can be performed in a method for interfering with viability of bacteria in a mucous environment, the method comprising: activating an Fe (II) chelator in the bacteria, the activating being performed by delivering the Fe(II) chelator into a mucus environment. According to the ninth approach, the delivering of the Fe(II) chelator into a mucus environment can be performed using an aerosol comprising the Fe(II) chelator with the Fe(II) chelator possibly being an Fe(II)-chelating protein or Fe(II)-chelating compound. According to the ninth approach the Fe(II) chelator can be a conalbumin.

According to a tenth approach, inactivating a phenazine and/or one or more phenazine related pathway can be performed in a method for interfering with viability of bacteria, the method comprising: activating an Fe(III) chelator in the bacteria, and activating an Fe(II) chelator in the bacteria. According to the tenth approach, the Fe(III) chelator and the Fe(II) chelator are administered for a time and under condition to substantially prevents and/or disrupts biofilm growth. According to the tenth approach, the Fe(III) and Fe(II) chelators can be administered for a time and under condition to act synergistically to substantially prevent and/or disrupt biofilm growth. According to the tenth approach, the Fe(III) and Fe(II) chelators can be administered for a time and under condition to disrupt mature biofilms.

According to an eleventh approach, inactivating a phenazine and/or one or more phenazine related pathway can be performed in a method for treating cystic fibrosis comprising: administering a therapeutically effective amount of a composition comprising an Fe(II) chelator alone or in combination with and an Fe(III) chelator to a individual. According to the eleventh approach, the administering can be performed by way of an aerosol comprising the Fe(III) chelator and/or the Fe(II) chelator. According to the eleventh approach, the Fe(II) chelator can be Ferrozine®, and an amount Ferrozine® and the therapeutically effective amount of the composition can range from 10-1000 µM. According to the eleventh approach, the Fe(II) chelator can be conalbumin, and the therapeutically effective amount of the composition can range from 10-1000 µM.

According to a twelfth approach, inactivating a phenazine and/or one or more phenazine related pathway can be performed by a composition comprising one or more agents suitable to inactivate a phenazine and/or one or more phenazine related pathways in a bacteria. According to the twelfth approach, the one or more agents can comprise an Fe(II) chelator and/or an Fe(III) chelator and in particular Ferrozine®, possibly comprised in the composition in an amount ranging between 10-1000 µM, and/or conalbumin, possibly comprised in the composition in an amount ranging between 10-1000 µM. According to the twelfth approach, the composition can be formulated to reduce biofilm accumulation by greater than approximately 50%. According to the twelfth approach, the composition can be a pharmaceutical composition in for treatment of cystic fibrosis and possibly further comprise a suitable vehicle for administering and/or delivering the one or more agents to an individual. According to the twelfth approach, the composition can be formulated for topical administration and in particular being in the form of aerosol.

In several embodiments provided herein, methods and systems for interfering with viability of bacteria and related compounds and compositions can also be performed by subtracting Fe(II) from the medium possibly in combination with subtracting Fe(III). Fe(II) subtraction can be performed in combination with inactivating a phenazine and/or one or more phenazine related pathway according with any one of the first to twelfth approaches herein described.

The examples set forth above are provided to give those of ordinary skill in the art a complete disclosure and description of how to make and use the embodiments of the compounds, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P756-USCD-Sequence-Listing-ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art upon the reading of the present disclosure, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all sub-ranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which are not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Thomashow, L. S. and D. M. Weller, Role of a phenazine antibiotic from *Pseudomonas fluorescens* in biological control of *Gaeumannomyces graminis* var. *tritici*. Journal of Bacteriology, 1988. 170(8): p. 3499-3508.
2. King, E. O., M. K. Ward, and D. E. Raney, Two simple media for the demonstration of pyocyanin and fluorescin. Journal of Laboratory and Clinical Medicine, 1954. 44(2): p. 301-307.
3. Wang, Y. and D. K. Newman, Redox reactions of phenazine antibiotics with ferric (hydr)oxides and molecular oxygen. Environmental Science & Technology, 2008. 42(7): p. 2380-2386.
4. Rahme, L. G., et al., Common virulence factors for bacterial pathogenicity in plants and animals. Science, 1995. 268(5219): p. 1899-1902.
5. Albrechtgary, A. M., et al., Bacterial iron transport—coordination properties of pyoverdin PaA, a peptidic siderophore of *Pseudomonas aeruginosa*. Inorganic Chemistry, 1994. 33(26): p. 6391-6402.

6. Zamri, A. and M. A. Abdallah, An improved stereocontrolled synthesis of pyochelin, siderophore of *Pseudomonas aeruginosa* and *Burkholderia cepacia*. Tetrahedron, 2000. 56(2): p. 249-256.
7. Youard, Z. A., et al., *Pseudomonas fluorescens* CHA0 produces enantio-pyochelin, the optical antipode of the *Pseudomonas aeruginosa* siderophore pyochelin. Journal of Biological Chemistry, 2007. 282(49): p. 35546-35553.
8. Schwertmann, U. and R. M. Cornell, Iron Oxides in the Laboratory: Preparation and Characterization. 2000, Weinheim, Germany: Wiley-VCH.
9. Liberati, N. T., et al., An ordered, nonredundant library of *Pseudomonas aeruginosa* strain PA14 transposon insertion mutants. Proceedings of the National Academy of Sciences of the United States of America, 2006. 103(8): p. 2833-2838.
10. Palmer, K. L., et al., Cystic fibrosis sputum supports growth and cues key aspects of *Pseudomonas aeruginosa* physiology. Journal of Bacteriology, 2005. 187(15): p. 5267-5277.
11. Elble, R., A simple and efficient procedure for transformation of yeasts. Biotechniques, 1992. 13(1): p. 18-20.
12. Burke, D., D. Dawson, and T. Stearns, Methods in Yeast Genetics: A Cold Spring Harbor Laboratory Course Manual. 2000, Plainview, N.Y.: Cold Spring Harbor Laboratory Press.
13. Dietrich, L. E. P., et al., The phenazine pyocyanin is a terminal signalling factor in the quorum sensing network of *Pseudomonas aeruginosa*. Molecular Microbiology, 2006. 61(5): p. 1308-1321.
14. Dehio, C. and M. Meyer, Maintenance of broad-host-range incompatibility group P and group Q plasmids and transposition of Tn5 in *Bartonella henselae* following conjugal plasmid transfer from *Escherichia coli*. Journal of Bacteriology, 1997. 179(2): p. 538-540.
15. Shanks, R. M. Q., et al., *Saccharomyces cerevisiae*-based molecular tool kit for manipulation of genes from gram-negative bacteria. Applied and Environmental Microbiology, 2006. 72(7): p. 5027-5036.
16. Bao, Y, et al., An improved Tn7-based system for the single-copy insertion of cloned genes into chromosomes of gram-negative bacteria. Gene, 1991. 109(1): p. 167-168.
17. Lambertsen, L., C. Sternberg, and S. Molin, Mini-Tn7 transposons for site-specific tagging of bacteria with fluorescent proteins. Environmental Microbiology, 2004. 6(7): p. 726-732.
18. Lambertsen, L., C. Sternberg, and S. Molin, Mini-Tn7 transposons for site-specific tagging of bacteria with fluorescent proteins. Environ Microbiol, 2004. 6(7): p. 726-32.
19. Liberati, N. T., et al., An ordered, nonredundant library of *Pseudomonas aeruginosa* strain PA14 transposon insertion mutants. Proceedings of the National Academy of Sciences of the United States of America, 2006. 103(8): p. 2833-2838.
20. Poole, K. and G. A. McKay, Iron acquisition and its control in *Pseudomonas aeruginosa: many roads lead to Rome*. Frontiers in Bioscience, 2003. 8: p. D661-D686.
21. Visca, P., A. Ciervo, and N. Orsi, Cloning and nucleotide-sequence of the pvdA gene encoding the pyoverdin biosynthetic enzyme L-ornithine $N^5$-oxygenase in *Pseudomonas aeruginosa*. Journal of Bacteriology, 1994. 176(4): p. 1128-1140.
22. Reimmann, C., et al., Dihydroaeruginoic acid synthetase and pyochelin synthetase, products of the pchEF genes, are induced by extracellular pyochelin in *Pseudomonas aeruginosa*. Microbiology, 1998. 144: p. 3135-3148.
23. Orrweaver, T. L. and J. W. Szostak, Yeast recombination—the association between double-strand gap repair and crossing-over. Proceedings of the National Academy of Sciences of the United States of America, 1983. 80(14): p. 4417-4421.
24. Ausubel, F. M., et al., eds. Current Protocols in Molecular Biology. 1992, John Wiley & Sons: New York, N.Y.
25. Whiteley, M., K. M. Lee, and E. P. Greenberg, Identification of genes controlled by quorum sensing in *Pseudomonas aeruginosa*. Proceedings of the National Academy of Sciences of the United States of America, 1999. 96(24): p. 13904-13909.
26. Koch, B., L. E. Jensen, and O. Nybroe, A panel of Tn7-based vectors for insertion of the gfp marker gene or for delivery of cloned DNA into Gram-negative bacteria at a neutral chromosomal site. Journal of Microbiological Methods, 2001. 45(3): p. 187-195.
27. Heydorn, A., et al., Quantification of biofilm structures by the novel computer program COMSTAT. Microbiology, 2000. 146: p. 2395-2407.
28. Merritt, P. A., T. Danhorn, and C. Fuqua, Motility and chemotaxis in *Agrobacterium tumefaciens* surface attachment and Biofilm formation. Journal of Bacteriology, 2007. 189(22): p. 8005-8014.
29. Komadel, P. and J. W. Stucki, QUANTITATIVE ASSAY OF MINERALS FOR FE-2+ AND FE-3+ USING 1,10-PHENANTHROLINE 0.3. A RAPID PHOTOCHEMICAL METHOD. Clays and Clay Minerals, 1988. 36(4): p. 379-381.
30. Mavrodi, D. V., W. Blankenfeldt, and L. S. Thomashow, Phenazine compounds in fluorescent *Pseudomonas* spp. biosynthesis and regulation. Annual Review of Phytopathology, 2006. 44: p. 417-445.
31. Schneider, T. L. and C. T. Walsh, Portability of oxidase domains in nonribosomal peptide synthetase modules. Biochemistry, 2004. 43(50): p. 15946-15955.
32. Bultreys, A., et al., High-performance liquid chromatography analyses of pyoverdin siderophores differentiate among phytopathogenic fluorescent *Pseudomonas* species. Applied and Environmental Microbiology, 2003. 69(2): p. 1143-1153.
33. Folschweiller, N., et al., The interaction between pyoverdin and its outer membrane receptor in *Pseudomonas aeruginosa* leads to different conformers: a time-resolved fluorescence study. Biochemistry, 2002. 41(49): p. 14591-14601.
34. Rashid, M. H. and A. Kornberg, Inorganic polyphosphate is needed for swimming, swarming, and twitching motilities of *Pseudomonas aeruginosa*. Proc Natl Acad Sci USA, 2000. 97(9): p. 4885-90.
35. Dietrich, L. E. P., et al., Redox-active antibiotics control gene expression and community behavior in divergent bacteria. Science, 2008. 321(5893): p. 1203-1206.
36. Mavrodi, D. V., et al., Functional analysis of genes for biosynthesis of pyocyanin and phenazine-1-carboxamide from *Pseudomonas aeruginosa* PAO1. Journal of Bacteriology, 2001. 183(21): p. 6454-6465.
37. O'Malley, Y. Q., et al., *Pseudomonas aeruginosa* pyocyanin directly oxidizes glutathione and decreases its levels in airway epithelial cells. American Journal of Physiology: Lung Cellular and Molecular Physiology, 2004. 287(1): p. L94-L103.

38. San, K. Y., et al., Metabolic engineering through cofactor manipulation and its effects on metabolic flux redistribution in *Escherichia coli*. Metabolic Engineering, 2002. 4(2): p. 182-192.
39. Bernofsky, C. and M. Swan, Improved cycling assay for nicotinamide adenine dinucleotide. Analytical Biochemistry, 1973. 53(2): p. 452-458.
40. Clark Jr., L. C., et al., Continuous recording of blood oxygen tensions by polarography. Journal of Applied Physiology, 1953. 6(3): p. 189-93.
41. Morel, F. M. M. and J. G. Hering, Principles and Applications of Aquatic Chemistry 1993, New York, N.Y.: John Wiley & Sons.
42. Aisen, P., Transferrin, the transferrin receptor, and the uptake of iron by cells, in Metal Ions in Biological Systems, Vol 35. 1998. p. 585-631.
43. Cox, C. D., Role of Pyocyanin in the Acquisition of Iron from Transferrin. Infection and Immunity, 1986. 52(1): p. 263-270.
44. M. A. Fischbach, H. Lin, D. R. Liu, C. T. Walsh, How pathogenic bacteria evade mammalian sabotage in the battle for iron. Nat. Chem. Biol. 2, 132-138 (2006).
45. M. L. Cartron, S. Maddocks, P. Gillingham, C. J. Craven, S. C. Andrews, Feo-transport of ferrous iron into bacteria. *Biometals* 19, 143-157 (2006).
46. E. Banin, M. L. Vasil, E. P. Greenberg, Iron and *Pseudomonas aeruginosa* biofilm formation. *Proc. Nat. Acad. Sci. U.S.A.* 102, 11076-11081 (2005).
47. S. Moreau-Marquis, G. A. O'Toole, B. A. Stanton, Tobramycin and FDA-approved iron chelators eliminate *Pseudomonas aeruginosa* biofilms on cystic fibrosis cells. *Am. J. Respir. Cell. Mol. Biol.* 41, 305-313 (2004).
48. P. K. Singh, M. R. Parsek, E. P. Greenberg, M. J. Walsh, A component of innate immunity prevents bacterial biofilm development. *Nature* 417, 552-555 (2002).
49. E. Banin, K. M. Brady, E. P. Greenberg, Chelator-induced dispersal and killing of *Pseudomonas aeruginosa* cells in a biofilm. *Appl. Environ. Microbiol.* 72, 2064-2069 (2006).
50. D. Worlitzsch et al, Effects of reduced mucus oxygen concentration in airway *Pseudomonas* infections of cystic fibrosis patients. *J. Clin. Invest.* 109, 317-325 (2002).
51. R. Wilson et al, Measurement of *Pseudomonas aeruginosa* phenazine pigments in sputum and assessment of their contribution to sputum sol toxicity for respiratory epithelium. *Infect. Immun.* 56, 2515-2517 (1988).
52. Y. Wang et al, Phenazine-1-carboxylic acid promotes bacterial biofilm development via ferrous iron acquisition. *J. Bacteriol.* 193, 3606-3617 (2011).
53. D. W. Reid et al, Increased airway iron as a potential factor in the persistence of *Pseudomonas aeruginosa* infection in cystic fibrosis. *Eur. Resp. J.* 30, 286-292 (2007).
54. D. W. Reid, G. J. Anderson, I. L. Lamont, Role of lung iron in determining the bacterial and host struggle in cystic fibrosis. *Am J. Physiol. Lung Cell. Mol. Physiol.* 297, L795-L802.
55. M. R. Miller et al, General consideration for lung function testing. *Eur. Resp. J.* 26, 153-10 159 (2005).
56. D. R. Lovley and E. J. P. Phillips, Rapid assay for microbially reducible ferric iron in aquatic sediments. *Appl. Environ. Microbiol.* 53, 1536-1540 (1987).
57. K. L. Tomlin et al, Quorum-sensing mutations affect attachment and stability of *Burkholderia cenocepacia* biofilms. *Appl. Environ. Microbiol.* 71, 5208-5218 (2005).
58. J. W. Ball, D. K. Nordstrom, R. B. McCleskey, T. B. To, A new method for the direct determination of dissolved Fe(III) concentration in acid mine waters. *USGS Pub.* 1, 1-10 (1999).
59. Aisen, P. 1998. Metal Ions in Biological Systems, vol. 35. p. 585-631.
60. Banin, E., A. Lozinski, K. M. Brady, et al. 2008. Proc. Nat. Acad. Sci. U.S.A. 105:16761-16766.
61. Banin, E., M. L. Vasil, E. P. Greenberg. 2005. Proc. Nat. Acad. Sci. U.S.A. 102:11076-11081.
62. Choi, H. M. T., J. Y. Chang, L. A. Trinh, et al. 2010. Nat. Biotechnol. 28:1208-1214.
63. Costerton, J. W., P. S. Stewart, E. P. Greenberg. 1999. Science 284:1318-1322.
64. Cox, C. D. 1986. Infect. Immun. 52:263-270.
65. Harrison, F. 2007. Microbiol. 153:917-923.
66. Hernandez, M. E., A. Kappler, D. K. Newman. 2004. Appl. Environ. Microbiol. 70:921-928.
67. Kaneko, Y., M. Thoendel, O. Olakanmi, et al. 2007. J. Clin. Invest. 117:877-888.
68. Klepac-Ceraj, V. K. P. Lemon, T. R. Martin, et al. 2010. Environ. Microbiol. 12:1293-1303.
69. Moreau-Marquis, S., J. Bomberger, G. G. Anderson, et al. 2008. Am. J. Physiol. 295:L25-L37.
70. Moreau-Marquis, S., G. A. O'Toole, B. A. Stanton. 2009. Am. J. Respir. 41:305-313.
71. Ochsner, U. A., Z. Johnson, M. L. Vasil. 2000. Microbiol. 146:185-198.
72. Poole, K., and G. A. McKay. 2003. Frontiers Biosci. 8:D661-D686.
73. Price-Whelan, A., L. E. P. Dietrich, D. K. Newman. 2007. J. Bacteriol. 189:6372-6381.
74. Price-Whelan, A., L. E. P. Dietrich, D. K. Newman. 2006. Nat. Chem. Biol. 2:71-78.
75. Ramos, I., L. E. P. Dietrich, A. Price-Whelan et al. 2010. Res. Microbiol. 161:187-191
76. Ratledge, C., L. G. Dover. 2000. Annu. Rev. Microbiol. 54:881-941.
77. Schalk, I. J. 2008. J. Inorganic Biochem. 102:1159-1169.
78. Singh, P. K., M. R. Parsek, E. P. Greenberg, M. J. Welsh. 2002. Nature 417:552-555.
79. Stookey, L. L. 1970. Anal. Chem. 42:779-781.
80. Wang, Y., D. K. Newman. 2008. Environ. Sci. Technol. 42:2380-2386.
81. Worlitzsch, D., R. Tarran, M. Ulrich, et al. 2002. J. Clin. Invest. 109:317-325.
82. Aisen, P. 1998. Transferrin, the transferrin receptor, and the uptake of iron by cells, p. 585-631, Metal Ions in Biological Systems, Vol 35, vol. 35.
83. Albrechtgary, A. M., S. Blanc, N. Rochel, A. Z. Ocaktan, and M. A. Abdallah. 1994. Bacterial iron transport—coordination properties of pyoverdin PaA, a peptidic siderophore of *Pseudomonas aeruginosa*. Inorganic Chemistry 33:6391-6402.
84. Ausubel, F. M., R. Brent, R. E. Kingston, D. D. Moore, J. G. Seidman, J. A. Smith, and K. Struhl (ed.). 1992. Current Protocols in Molecular Biology. John Wiley & Sons, New York, N.Y.
85. Banin, E., A. Lozinski, K. M. Brady, E. Berenshtein, P. W. Butterfield, M. Moshe, M. Chevion, and E. P. Greenberg. 2008. The potential of desferrioxamine-gallium as an anti-*Pseudomonas* therapeutic agent. Proceedings of the National Academy of Sciences of the United States of America 105:16761-16766.
86. Banin, E., M. L. Vasil, and E. P. Greenberg. 2005. Iron and *Pseudomonas aeruginosa* biofilm formation. Pro- 87. Bao, Y., D. P. Lies, H. Fu, and G. P. Roberts. 1991. An improved Tn7-based system for the single-copy insertion of cloned genes into chromosomes of gram-negative bacteria. Gene 109:167-168.
88. Berlutti, F., C. Morea, A. Battistoni, S. Sarli, P. Cipriani, F. Superb, M. G. Ammendolia, and P. Valenti. 2005. Iron availability influences aggregation, biofilm, adhesion and invasion of *Pseudomonas aeruginosa* and *Burkholderia cenocepacia*. International Journal of Immunopathology and Pharmacology 18:661-670.
89. Bouchara, J. P., H. Y. Hsieh, S. Croquefer, R. Barton, V. Marchais, M. Pihet, and T. C. Chang. 2009. Development of an oligonucleotide array for direct detection of fungi in sputum samples from patients with cystic fibrosis. J Clin Microbiol 47:142-152.
90. Bultreys, A., I. Gheysen, B. Wathelet, H. Maraite, and E. de Hoffmann. 2003. High-performance liquid chromatography analyses of pyoverdin siderophores differentiate among phytopathogenic fluorescent *Pseudomonas* species. Applied and Environmental Microbiology 69:1143-1153.
91. Burke, D., D. Dawson, and T. Stearns. 2000. Methods in Yeast Genetics: A Cold Spring Harbor Laboratory Course Manual. Cold Spring Harbor Laboratory Press, Plainview, N.Y.
92. Cartron, M. L., S. Maddocks, P. Gillingham, C. J. Craven, and S. C. Andrews. 2006. Feo-transport of ferrous iron into bacteria. Biometals 19:143-157.
93. Chatfield, C. H., and N. P. Cianciotto. 2007. The secreted pyomelanin pigment of *Legionella pneumophila* confers ferric reductase activity. Infection and Immunity 75:4062-70.
94. Costerton, J. W., P. S. Stewart, and E. P. Greenberg. 1999. Bacterial biofilms: a common cause of persistent infections. Science 284:1318-1322.
95. Cox, C. D. 1986. Role of pyocyanin in the acquisition of iron from transferrin. Infection and Immunity 52:263-270.
96. De Vos, D., M. De Chial, C. Cochez, S. Jansen, B. Tummler, J. M. Meyer, and P. Cornelis. 2001. Study of pyoverdin type and production by *Pseudomonas aeruginosa* isolated from cystic fibrosis patients: prevalence of type II pyoverdin isolates and accumulation of pyoverdin-negative mutations. Archives of Microbiology 175:384-388.
97. Dehio, C., and M. Meyer. 1997. Maintenance of broad-host-range incompatibility group P and group Q plasmids and transposition of Tn5 in *Bartonella henselae* following conjugal plasmid transfer from *Escherichia coli*. Journal of Bacteriology 179:538-540.
98. Dietrich, L. E. P., A. Price-Whelan, A. Petersen, M. Whiteley, and D. K. Newman. 2006. The phenazine pyocyanin is a terminal signalling factor in the quorum sensing network of *Pseudomonas aeruginosa*. Molecular Microbiology 61:1308-1321.
99. Dietrich, L. E. P., T. K. Teal, A. Price-Whelan, and D. K. Newman. 2008. Redox-active antibiotics control gene expression and community behavior in divergent bacteria. Science 321:1203-1206.
100. Elble, R. 1992. A simple and efficient procedure for transformation of yeasts. Biotechniques 13:18-20.
101. Folschweiller, N., J. Gallay, M. Vincent, M. A. Abdallah, F. Pattus, and I. J. Schalk. 2002. The interaction between pyoverdin and its outer membrane receptor in *Pseudomonas aeruginosa* leads to different conformers: a time-resolved fluorescence study. Biochemistry 41:14591-14601.
102. Fothergill, J. L., S. Panagea, C. A. Hart, M. J. Walshaw, T. L. Pitt, and C. Winstanley. 2007. Widespread pyocyanin over-production among isolates of a cystic fibrosis epidemic strain. BMC Microbiology 7:45.
103. Ghosh, S., R. Mukherjee, P. J. Sadler, and S. Verma. 2008. Periodic iron nanomineralization in human serum transferrin fibrils. Angewandte Chemie-International Edition 47:2217-2221.
104. Griffin, A. S., S. A. West, and A. Buckling. 2004. Cooperation and competition in pathogenic bacteria. Nature 430:1024-7.
105. Haas, D., and G. Defago. 2005. Biological control of soil-borne pathogens by fluorescent pseudomonads. Nature Reviews Microbiology 3:307-319.
106. Harrison, F. 2007. Microbial ecology of the cystic fibrosis lung. Microbiology 153:917-923.
107. Hassan, H. M., and I. Fridovich. 1980. Mechanism of the antibiotic action pyocyanin. J Bacteriol 141:156-63.
108. Hernandez, M. E., A. Kappler, and D. K. Newman. 2004. Phenazines and other redox-active antibiotics promote microbial mineral reduction. Applied and Environmental Microbiology 70:921-928.
109. Hernandez, M. E., and D. K. Newman. 2001. Extracellular electron transfer. Cellular and Molecular Life Sciences 58:1562-1571.
110. Heydorn, A., A. T. Nielsen, M. Hentzer, C. Sternberg, M. Givskov, B. K. Ersboll, and S. Molin. 2000. Quantification of biofilm structures by the novel computer program COMSTAT. Microbiology 146:2395-2407.
111. Kaneko, Y., M. Thoendel, O. Olakanmi, B. E. Britigan, and P. K. Singh. 2007. The transition metal gallium disrupts *Pseudomonas aeruginosa* iron metabolism and has antimicrobial and antibiofilm activity. Journal of Clinical Investigation 117:877-888.
112. King, E. O., M. K. Ward, and D. E. Raney. 1954. Two simple media for the demonstration of pyocyanin and fluorescin. Journal of Laboratory and Clinical Medicine 44:301-307.
113. Koch, B., L. E. Jensen, and O. Nybroe. 2001. A panel of Tn7-based vectors for insertion of the gfp marker gene or for delivery of cloned DNA into Gram-negative bacteria at a neutral chromosomal site. Journal of Microbiological Methods 45:187-195.
114. Komadel, P., and J. W. Stucki. 1988. Quantitative assay of minerals for Fe2+ and Fe3+ using 1,10-phenanthroline. A rapid photochemical method. Clays and Clay Minerals 36:379-381.
115. Lambertsen, L., C. Sternberg, and S. Molin. 2004. Mini-Tn7 transposons for site-specific tagging of bacteria with fluorescent proteins. Environmental Microbiology 6:726-732.
116. Lau, G. W., D. J. Hassett, H. Ran, and F. Kong. 2004. The role of pyocyanin in *Pseudomonas aeruginosa* infection. Trends in Molecular Medicine 10:599-606.
117. Lau, G. W., H. Ran, F. Kong, D. J. Hassett, and D. Mavrodi. 2004. *Pseudomonas aeruginosa* pyocyanin is critical for lung infection in mice. Infection and Immunity 72:4275-8.
118. Liberati, N. T., J. M. Urbach, S. Miyata, D. G. Lee, E. Drenkard, G. Wu, J. Villanueva, T. Wei, and F. M. Ausubel. 2006. An ordered, nonredundant library of *Pseudomonas aeruginosa* strain PA14 transposon insertion mutants. Proceedings of the National Academy of Sciences of the United States of America 103:2833-2838.

119. Mahajan-Miklos, S., M. W. Tan, L. G. Rahme, and F. M. Ausubel. 1999. Molecular mechanisms of bacterial virulence elucidated using a *Pseudomonas aeruginosa-Caenorhabditis elegans* pathogenesis model. Cell 96:47-56.

120. Marshall, B., A. Stintzi, C. Gilmour, J. M. Meyer, and K. Poole. 2009. Citrate-mediated iron uptake in *Pseudomonas aeruginosa*: involvement of the citrate-inducible FecA receptor and the FeoB ferrous iron transporter. Microbiology 155:305-315.

121. Marsili, E., D. B. Baron, I. D. Shikhare, D. Coursolle, J. A. Gralnick, and D. R. Bond. 2008. *Shewanella* secretes flavins that mediate extracellular electron transfer. Proceedings of the National Academy of Sciences of the United States of America 105:3968-3973.

122. Mashburn, L. M., A. M. Jett, D. R. Akins, and M. Whiteley. 2005. *Staphylococcus aureus* serves as an iron source for *Pseudomonas aeruginosa* during in vivo coculture. Journal of Bacteriology 187:554-566.

123. Mavrodi, D. V., W. Blankenfeldt, and L. S. Thomashow. 2006. Phenazine compounds in fluorescent *Pseudomonas* spp. biosynthesis and regulation. Annual Review of Phytopathology 44:417-445.

124. Merritt, P. A., T. Danhorn, and C. Fuqua. 2007. Motility and chemotaxis in *Agrobacterium tumefaciens* surface attachment and Biofilm formation. Journal of Bacteriology 189:8005-8014.

125. Moreau-Marquis, S., J. M. Bomberger, G. G. Anderson, A. Swiatecka-Urban, S. Y. Ye, G. A. O'Toole, and B. A. Stanton. 2008. The Delta F508-CFTR mutation results in increased biofilm formation by *Pseudomonas aeruginosa* by increasing iron availability. American Journal of Physiology-Lung Cellular and Molecular Physiology 295: L25-L37.

126. Moreau-Marquis, S., J. M. Bomberger, G. G. Anderson, A. Swiatecka-Urban, S. Y. Ye, G. A. O'Toole, and B. A. Stanton. 2008. The ΔF508-CFTR mutation results in increased biofilm formation by *Pseudomonas aeruginosa* by increasing iron availability. American Journal of Physiology—Lung Cellular and Molecular Physiology 295:L25-L37.

127. Moreau-Marquis, S., G. A. O'Toole, and B. A. Stanton. 2009. Tobramycin and FDA-approved iron chelators eliminate *Pseudomonas aeruginosa* biofilms on cystic fibrosis cells. American Journal of Respiratory Cell and Molecular Biology 41:305-313.

128. Morel, F. M. M., and J. G. Hering. 1993. Principles and Applications of Aquatic Chemistry John Wiley & Sons, New York, N.Y.

129. Ochsner, U. A., Z. Johnson, and M. L. Vasil. 2000. Genetics and regulation of two distinct haem-uptake systems, phu and has, in *Pseudomonas aeruginosa*. Microbiology 146:185-198.

130. Orrweaver, T. L., and J. W. Szostak. 1983. Yeast recombination—the association between double-strand gap repair and crossing-over. Proceedings of the National Academy of Sciences of the United States of America 80:4417-4421.

131. Palmer, K. L., L. M. Mashburn, P. K. Singh, and M. Whiteley. 2005. Cystic fibrosis sputum supports growth and cues key aspects of *Pseudomonas aeruginosa* physiology. Journal of Bacteriology 187:5267-5277.

132. Patriquin, G. M., E. Banin, C. Gilmour, R. Tuchman, E. P. Greenberg, and K. Poole. 2008. Influence of quorum sensing and iron on twitching motility and biofilm formation in *Pseudomonas aeruginosa*. Journal of Bacteriology 190:662-671.

133. Pierre, J. L., M. Fontecave, and R. R. Crichton. 2002. Chemistry for an essential biological process: the reduction of ferric iron. Biometals 15:341-346.

134. Poole, K., and G. A. McKay. 2003. Iron acquisition and its control in *Pseudomonas aeruginosa*: many roads lead to Rome. Frontiers in Bioscience 8:D661-D686.

135. Price-Whelan, A., L. E. P. Dietrich, and D. K. Newman. 2007. Pyocyanin alters redox homeostasis and carbon flux through central metabolic pathways in *Pseudomonas aeruginosa* PA14. Journal of Bacteriology 189:6372-6381.

136. Price-Whelan, A., L. E. P. Dietrich, and D. K. Newman. 2006. Rethinking 'secondary' metabolism: physiological roles for phenazine antibiotics. Nature Chemical Biology 2:71-78.

137. Rahme, L. G., E. J. Stevens, S. F. Wolfort, J. Shao, R. G. Tompkins, and F. M. Ausubel. 1995. Common virulence factors for bacterial pathogenicity in plants and animals. Science 268:1899-1902.

138. Ramos, I., L. E. P. Dietrich, A. Price-Whelan, and D. K. Newman. 2010. Phenazines affect biofilm formation by *Pseudomonas aeruginosa* in similar ways at various scales. Research in Microbiology 161:187-191.

139. Ratledge, C., and L. G. Dover. 2000. Iron metabolism in pathogenic bacteria. Annual Review of Microbiology 54:881-941.

140. Reid, D. W., G. J. Anderson, and I. L. Lamont. 2009. Role of lung iron in determining the bacterial and host struggle in cystic fibrosis. American Journal of Physiology—Lung Cellular and Molecular Physiology 297: L795-L802.

141. Reid, D. W., V. Carroll, C. O'May, A. Champion, and S. M. Kirov. 2007. Increased airway iron as a potential factor in the persistence of *Pseudomonas aeruginosa* infection in cystic fibrosis. European Respiratory Journal 30:286-292.

142. Reimmann, C., L. Serino, M. Beyeler, and D. Haas. 1998. Dihydroaeruginoic acid synthetase and pyochelin synthetase, products of the pchEF genes, are induced by extracellular pyochelin in *Pseudomonas aeruginosa*. Microbiology 144:3135-3148.

143. Rogan, M. P., C. C. Taggart, C. M. Greene, P. G. Murphy, S. J. O'Neill, and N. G. McElvaney. 2004. Loss of microbicidal activity and increased formation of biofilm due to decreased lactoferrin activity in patients with cystic fibrosis. Journal of Infectious Diseases 190:1245-1253.

144. Rogers, G. B., M. P. Carroll, and K. D. Bruce. 2009. Studying bacterial infections through culture-independent approaches. Journal of Medical Microbiology 58:1401-1418.

145. Schalk, I. J. 2008. Metal trafficking via siderophores in Gram-negative bacteria: specificities and characteristics of the pyoverdin pathway. Journal of Inorganic Biochemistry 102:1159-1169.

146. Schneider, T. L., and C. T. Walsh. 2004. Portability of oxidase domains in nonribosomal peptide synthetase modules. Biochemistry 43:15946-15955.

147. Schwertmann, U., and R. M. Cornell. 2000. Iron Oxides in the Laboratory: Preparation and Characterization. Wiley-VCH, Weinheim, Germany.

148. Shanks, R. M. Q., N. C. Caiazza, S. M. Hinsa, C. M. Toutain, and G. A. O'Toole. 2006. *Saccharomyces cerevisiae*-based molecular tool kit for manipulation of genes from gram-negative bacteria. Applied and Environmental Microbiology 72:5027-5036.

149. Singh, P. K., M. R. Parsek, E. P. Greenberg, and M. J. Welsh. 2002. A component of innate immunity prevents bacterial biofilm development. Nature 417:552-555.

150. Smith, E. E., D. G. Buckley, Z. N. Wu, C. Saenphimmachak, L. R. Hoffman, D. A. D'Argenio, S. I. Miller, B. W. Ramsey, D. P. Speert, S. M. Moskowitz, J. L. Burns, R. Kaul, and M. V. Olson. 2006. Genetic adaptation by *Pseudomonas aeruginosa* to the airways of cystic fibrosis patients. Proceedings of the National Academy of Sciences of the United States of America 103:8487-8492.

151. Thomashow, L. S., and D. M. Weller. 1988. Role of a phenazine antibiotic from *Pseudomonas fluorescens* in biological control of *Gaeumannomyces graminis* var. *tritici*. Journal of Bacteriology 170:3499-3508.

152. Visca, P., A. Ciervo, and N. Orsi. 1994. Cloning and nucleotide-sequence of the pvdA gene encoding the pyoverdin biosynthetic enzyme L-ornithine N5-oxygenase in *Pseudomonas aeruginosa*. Journal of Bacteriology 176:1128-1140.

153. Wang, Y., S. E. Kern, and D. K. Newman. 2010. Endogenous phenazine antibiotics promote anaerobic survival of *Pseudomonas aeruginosa* via extracellular electron transfer. Journal of Bacteriology 192:365-369.

154. Wang, Y., and D. K. Newman. 2008. Redox reactions of phenazine antibiotics with ferric (hydr)oxides and molecular oxygen. Environmental Science & Technology 42:2380-2386.

155. Weaver, V. B., and R. Kolter. 2004. *Burkholderia* spp. alter *Pseudomonas aeruginosa* physiology through iron sequestration. Journal of Bacteriology 186:2376-2384.

156. Whiteley, M., K. M. Lee, and E. P. Greenberg. 1999. Identification of genes controlled by quorum sensing in *Pseudomonas aeruginosa*. Proceedings of the National Academy of Sciences of the United States of America 96:13904-13909.

157. Wilson, R., D. A. Sykes, D. Watson, A. Rutman, G. W. Taylor, and P. J. Cole. 1988. Measurement of *Pseudomonas aeruginosa* phenazine pigmenets in sputum and assessment of their contribution to sputum sol toxicity for respiratory epithelium. Infection and Immunity 56:2515-2517.

158. Wilson, R., D. A. Sykes, D. Watson, A. Rutman, G. W. Taylor, and P. J. Cole. 1988. Measurement of *Pseudomonas aeruginosa* phenazine pigments in sputum and assessment of their contribution to sputum sol toxicity for respiratory epithelium. Infection and Immunity 56:2515-2517.

159. Worlitzsch, D., R. Tarran, M. Ulrich, U. Schwab, A. Cekici, K. C. Meyer, P. Birrer, G. Bellon, J. Berger, T. Weiss, K. Botzenhart, J. R. Yankaskas, S. Rondell, R. C. Boucher, and G. Doring. 2002. Effects of reduced mucus oxygen concentration in airway *Pseudomonas* infections of cystic fibrosis patients. Journal of Clinical Investigation 109:317-325.

160. Worst, D. J., M. M. Gerrits, C. M. Vandenbroucke-Grauls, and J. G. Kusters. 1998. *Helicobacter pylori* ribBA-mediated riboflavin production is involved in iron acquisition. Journal of Bacteriology 180:1473-1479.

161. Youard, Z. A., G. L. Mislin, P. A. Majcherczyk, I. J. Schalk, and C. Reimmann. 2007. *Pseudomonas fluorescens* CHA0 produces enantio-pyochelin, the optical antipode of the *Pseudomonas aeruginosa* siderophore pyochelin. Journal of Biological Chemistry 282:35546-35553.

162. Zamri, A., and M. A. Abdallah. 2000. An improved stereocontrolled synthesis of pyochelin, siderophore of *Pseudomonas aeruginosa* and *Burkholderia cepacia*. Tetrahedron 56:249-256.

163. Zhao, Q. X., and K. Poole. 2002. Differential effects of mutations in tonB1 on intrinsic multidrug resistance and iron acquisition in *Pseudomonas aeruginosa*. Journal of Bacteriology 184:2045-2049.

164. Deziel, E., Lepine, F., Milot, S. and Villemur, R., 2003. rhlA is required for the production of a novel biosurfactant promoting swarming motility in *Pseudomonas aeruginosa*: 3-(3-hydroxyalkanoyloxy)alkanoic acids (HAAs), the precursors of rhamnolipids. Microbiology (Reading, England) 149, 2005-2013

165. Dietrich, L. E. P., Price-Whelan, A., Petersen, A., Whiteley, M. and Newman, D. K., 2006. The phenazine pyocyanin is a terminal signalling factor in the quorum sensing network of *Pseudomonas aeruginosa*. Molecular Microbiology 61, 1308-1321

166. Dietrich, L. E. P., Teal, T. K., Price-Whelan, A. and Newman, D. K., 2008. Redox-active antibiotics control gene expression and community behavior in divergent bacteria. Science 321, 1203-1206

167. Govan, J. R. and Deretic, V., 1996. Microbial pathogenesis in cystic fibrosis: mucoid *Pseudomonas aeruginosa* and *Burkholderia cepacia*. Microbiological reviews 60, 539-574

168. Heydorn, A., Nielsen, A. T., Hentzer, M., Sternberg, C., Givskov, M., Ersboll, B. K. and Molin, S., 2000. Quantification of biofilm structures by the novel computer program COMSTAT. Microbiology (Reading, England) 146 (Pt 10), 2395-2407

169. Johansen, H. K., Kovesi, T. A., Koch, C., Corey, M., Hoiby, N. and Levison, H., 1998. *Pseudomonas aeruginosa* and *Burkholderia cepacia* infection in cystic fibrosis patients treated in Toronto and Copenhagen. Pediatric Pulmonology 26, 89-96

170. Lambertsen, L., Sternberg, C. and Molin, S., 2004. Mini-Tn7 transposons for site-specific tagging of bacteria with fluorescent proteins. Environmental microbiology 6, 726-732

171. Maddula, V. S. R. K., Zhang, Z., Pierson, E. A. and Pierson, L. S., 3rd, 2006. Quorum sensing and phenazines are involved in biofilm formation by *Pseudomonas chlororaphis* (*aureofaciens*) strain 30-84. Microbial Ecology 52, 289-301

172. Maddula, V. S. R. K., Pierson, E. A. and Pierson, L. S., 3rd, 2008. Altering the ratio of phenazines in *Pseudomonas chlororaphis* (aureofaceins) strain 30-84: Effects on biofilm formation and pathogen inhibition. Journal of bacteriology 190, 2759-2766

173. Mavrodi, D. V., Bonsall, R. F., Delaney, S. M., Soule, M. J., Phillips, G. and Thomashow, L. S., 2001. Functional analysis of genes for biosynthesis of pyocyanin and phenazine-1-carboxamide from *Pseudomonas aeruginosa* PAO1. Journal of bacteriology 183, 6454-6465

174. O'Toole, G. A. and Kolter, R., 1998. Flagellar and twitching motility are necessary for *Pseudomonas aeruginosa* biofilm development. Mol Microbiol 30, 295-304

175. O'Toole, G. A., Pratt, L. A., Watnick, P. I., Newman, D. K., Weaver, V. B. and Kolter, R., 1999. Genetic approaches to study of biofilms. Methods in enzymology 310, 91-109

176. Rashid, M. H. and Kornberg, A., 2000. Inorganic polyphosphate is needed for swimming, swarming, and twitching motilities of *Pseudomonas aeruginosa*. Proceedings of the National Academy of Sciences of the United States of America 97, 4885-4890

177. Shapiro, J. A., 1984. The use of Mudlac transposons as tools for vital staining to visualize clonal and non-clonal patterns of organization in bacterial growth on agar surfaces. Journal of general microbiology 130, 1169-1181

178. Singh, P. K., Schaefer, A. L., Parsek, M. R., Moninger, T. O., Welsh, M. J. and Greenberg, E. P., 2000. Quorum-sensing signals indicate that cystic fibrosis lungs are infected with bacterial biofilms. Nature 407, 762-764

179. Singh, P. K., Parsek, M. R., Greenberg, E. P. and Welsh, M. J., 2002. A component of innate immunity prevents bacterial biofilm development. Nature 417, 552-555

180. Aslund, F., K. D. Berndt, and A. Holmgren. 1997. Redox potentials of glutaredoxins and other thiol-disulfide oxidoreductases of the thioredoxin superfamily determined by direct protein-protein redox equilibria. J. Biol. Chem. 272:30780-30786.

181. Baron, S. S., and J. J. Rowe. 1981. Antibiotic action of pyocyanin. Antimicrob. Agents Chemother. 20:814-820.

182. Baron, S. S., G. Terranova, and J. J. Rowe. 1989. Molecular mechanism of the antimicrobial action of pyocyanin. Curr. Microbiol. 18:223-230.

183. Beifuss, U., and M. Tietze. 2005. Methanophenazine and other natural biologically active phenazines. Top. Curr. Chem. 244:77-113.

184. Benz, M., B. Schink, and A. Brune. 1998. Humic acid reduction by Propionibacterium freudenreichii and other fermenting bacteria. Appl. Environ. Microbiol. 64:4507-4512.

185. Bernofsky, C., and M. Swan. 1973. Improved cycling assay for nicotinamide adenine dinucleotide. Anal. Biochem. 53:452-458.

186. Bessette, P. H., F. Aslund, J. Beckwith, and G. Georgiou. 1999. Efficient folding of proteins with multiple disulfide bonds in the Escherichia coli cytoplasm. Proc. Natl. Acad. Sci. U.S.A 96:13703-13708.

187. Bunik, V. I., and C. Sievers. 2002. Inactivation of the 2-oxo acid dehydrogenase complexes upon generation of intrinsic radical species. Eur. J. Biochem. 269:5004-5015.

188. Byng, G. S., D. C. Eustice, and R. A. Jensen. 1979. Biosynthesis of phenazine pigments in mutant and wild-type cultures of Pseudomonas aeruginosa. J. Bacteriol. 138:846-852.

189. Chang, P. C., and A. C. Blackwood. 1969. Simultaneous production of three phenazine pigments by Pseudomonas aeruginosa Mac 436. Can. J. Microbiol. 15:439-444.

190. Clark Jr., L. C., R. Wolf, D. Granger, and Z. Taylor. 1953. Continuous recording of blood oxygen tensions by polarography. J. Appl. Physiol. 6:189-93.

191. Conway, T. 1992. The Entner-Doudoroff pathway: history, physiology and molecular biology. FEMS Microbiol. Rev. 103:1-28.

192. Cox, C. D. 1986. Role of pyocyanin in the acquisition of iron from transferrin. Infect. Immun. 52:263-270.

193. Cronan, J. e., X. Zhao, and Y. Jiang. 2005. Function, attachment and synthesis of lipoic acid in Escherichia coli. Adv. Microb. Physiol. 50:103-146.

194. Davis, G., and P. J. Thornalley. 1983. Free radical production from the aerobic oxidation of reduced pyridine nucleotides catalyzed by phenazine derivatives. Biochim. Biophys. Acta 724:456-464.

195. de Graef, M. R., S. Alexeeva, J. L. Snoep, and M. J. T. de Mottos. 1999. The steady-state internal redox state (NADH/NAD) reflects the external redox state and is correlated with catabolic adaptation in Escherichia coli. J. Bacteriol. 181:2351-2357.

196. de Kok, A., A. F. Hengeveld, A. Martin, and A. H. Westphal. 1998. The pyruvate dehydrogenase complex from Gram-negative bacteria. Biochim. Biophys. Acta 1385:353-366.

197. Dietrich, L. E. P., A. Price-Whelan, A. Petersen, M. Whiteley, and D. K. Newman. 2006. The phenazine pyocyanin is a terminal signalling factor in the quorum sensing network of Pseudomonas aeruginosa. Mol. Microbiol. 61:1308-1321.

198. Emde, R., and B. Schink. 1990. Oxidation of glycerol, lactate, and propionate by Propionibacterium freudenreichii in a poised-potential amperometric culture system. Arch. Microbiol. 153:506-512.

199. Emde, R., A. Swain, and B. Schink. 1989. Anaerobic oxidation of glycerol by Escherichia coli in an amperometric poised-potential culture system. Appl. Microbiol. Biotechnol. 32:170-175.

200. Eschbach, M., K. Schreiber, K. Trunk, J. Buer, D. Jahn, and M. Schobert. 2004. Long-term anaerobic survival of the opportunistic pathogen Pseudomonas aeruginosa via pyruvate fermentation. J. Bacteriol. 186:4596-4604.

201. Friedheim, E., and L. Michaelis. 1931. Potentiometric study of pyocyanin. J. Biol. Chem. 91:355-368.

202. Friedheim, E. A. H. 1931. Pyocyanin, an accessory respiratory pigment. J. Exp. Med. 54:207-221.

203. Fuhrer, T., E. Fischer, and U. Sauer. 2005. Experimental identification and quantification of glucose metabolism in seven bacterial species. J. Bacteriol. 187:1581-1590.

204. Fultz, M. L., and R. A. Durst. 1982. Mediator compounds for the electrochemical study of biological redox systems: a compilation. Anal. Chim. Acta 140:1-18.

205. Gardner, P. R. 1996. Superoxide production by the mycobacterial and pseudomonad quinoid pigments phthiocol and pyocyanin in human lung cells. Arch. Biochem. Biophys. 333:267-274.

206. Hassan, H. M., and I. Fridovich. 1979. Intracellular production of superoxide radical and of hydrogen peroxide by redox active compounds. Arch. Biochem. Biophys. 192:385-395.

207. Hassan, H. M., and I. Fridovich. 1980. Mechanism of the antibiotic action of pyocyanin. J. Bacteriol. 141:156-163.

208. Hassett, D. J., L. Charniga, K. Bean, D. E. Ohman, and M. S. Cohen. 1992. Response of Pseudomonas aeruginosa to pyocyanin: mechanisms of resistance, antioxidant defenses, and demonstration of a manganese-cofactored superoxide dismutase. Infect. Immun. 60:328-336.

209. Hassett, D. J., H. P. Schweizer, and D. E. Ohman. 1995. Pseudomonas aeruginosa sodA and sodB mutants defective in manganese- and iron-cofactored superoxide dismutase activity demonstrate the importance of the iron-cofactored form in aerobic metabolism. J. Bacteriol. 177: 6330-6337.

210. Hernandez, M. E., A. Kappler, and D. K. Newman. 2004. Phenazines and other redox-active antibiotics promote microbial mineral reduction. Appl. Environ. Microbiol. 70:921-928.

211. Hernandez, M. E., and D. K. Newman. 2001. Extracellular electron transfer. Cell. Mol. Life Sci. 58:1562-1571.

212. Ingledew, W. M., and J. J. Campbell. 1969. A new resuspension medium for pyocyanin production. Can. J. Microbiol. 15:595-598.

213. Jolley, K. A., D. G. Maddocks, S. L. Gyles, Z. Mullan, S. L. Tang, M. L. Dyall-Smith, D. W. Hough, and M. J. Danson. 2000. 2-Oxoacid dehydrogenase multienzyme complexes in the halophilic Archaea? Gene sequences and protein structural predictions. Microbiology 146:1061-1069.

214. Kerr, J. R., G. W. Taylor, A. Rutman, N. Hoiby, P. J. Cole, and R. Wilson. 1999. *Pseudomonas aeruginosa* pyocyanin and 1-hydroxyphenazine inhibit fungal growth. J. Clin. Pathol. 52:385-387.

215. Kito, N., Y. Ohnishi, M. Nagami, and A. Ohno. 1974. Reduction by a model of NAD(P)H: construction of electron bridges. Chemistry Letters: 353-356.

216. Kolter, R., D. A. Siegele, and A. Tormo. 1993. The stationary phase of the bacterial life cycle. Annu. Rev. Microbiol. 47:855-874.

217. Lau, G. W., D. J. Hassett, H. Ran, and F. Kong. 2004. The role of pyocyanin in *Pseudomonas aeruginosa* infection. Trends Mol. Med. 10:599-606.

218. Learoyd, S. A., R. G. Kroll, and C. F. Thurston. 1992. An investigation of dye reduction by food-borne bacteria. J. Appl. Bacteriol. 72:479-485.

219. Liberati, N. T., J. M. Urbach, S. Miyata, D. G. Lee, E. Drenkard, W. Gang, J. Villanueva, T. Wei, and F. M. Ausubel. 2006. An ordered, nonredundant library of *Pseudomonas aeruginosa* strain PA14 transposon insertion mutants. Proc. Natl. Acad. Sci. U.S.A 103:2833-2838.

220. Lies, D. P., M. E. Hernandez, A. Kappler, R. E. Mielke, J. A. Gralnick, and D. K. Newman. 2005. *Shewanella oneidensis* MR-1 uses overlapping pathways for iron reduction at a distance and by direct contact under conditions relevant for biofilms. Appl. Environ. Microbiol. 71:4414-4426.

221. Look, D. C., L. L. Stoll, S. A. Romig, A. Humlicek, B. E. Britigan, and G. M. Denning. 2005. Pyocyanin and its precursor phenazine-1-carboxylic acid increase IL-8 and intercellular adhesion molecule-1 expression in human airway epithelial cells by oxidant-dependent mechanisms. J. Immunol. 175:4017-4023.

222. Lyczak, J. B., C. L. Cannon, and G. B. Pier. 2002. Lung infections associated with cystic fibrosis. Clin. Microbiol. Rev. 15:194-222.

223. Mavrodi, D., W. Blankenfeldt, and L. S. Thomashow. 2006. Phenazine compounds in fluorescent *Pseudomonas* spp.: biosynthesis and regulation. Annu. Rev. Phytopathol. 44:417-445.

224. Mavrodi, D. V., R. F. Bonsall, S. M. Delaney, M. J. Soule, G. Phillips, and L. S. Thomashow. 2001. Functional analysis of genes for biosynthesis of pyocyanin and phenazine-1-carboxamide from *Pseudomonas aeruginosa* PAO1. J. Bacteriol. 183:6454-6465.

225. McKinlay, J. B., and J. G. Zeikus. 2004. Extracellular iron reduction is mediated in part by neutral red and hydrogenase in *Escherichia coli*. Appl. Environ. Microbiol. 70:3467-3474.

226. Mossner, E., M. Huber-Wunderlich, A. Rietsch, J. Beckwith, R. Glockshuber, and F. Aslund. 1999. Importance of redox potential for the in vivo function of the cytoplasmic disulfide reductant thioredoxin from *Escherichia coli*. J. Biol. Chem. 274:25254-25259.

227. O'Malley, Y. Q., K. J. Reszka, G. T. Rasmussen, M. Y. Abdalla, G. M. Denning, and B. E. Britigan. 2003. The *Pseudomonas* secretory product pyocyanin inhibits catalase activity in human lung epithelial cells. Am. J. Physiol. Lung Cell. Mol. Physiol. 285:L1077-L1086.

228. O'Malley, Y. Q., K. J. Reszka, D. R. Spitz, G. M. Denning, and B. E. Britigan. 2004. *Pseudomonas aeruginosa* pyocyanin directly oxidizes glutathione and decreases its levels in airway epithelial cells. Am. J. Physiol. Lung Cell. Mol. Physiol. 287:L94-L103.

229. Palmer, K. L., L. M. Mashburn, P. K. Singh, and M. Whiteley. 2005. Cystic fibrosis sputum supports growth and cues key aspects of *Pseudomonas aeruginosa* physiology. J. Bacteriol. 187:5267-5277.

230. Pierson, L. S., 3rd, V. D. Keppenne, and D. W. Wood. 1994. Phenazine antibiotic biosynthesis in *Pseudomonas aureofaciens* 30-84 is regulated by PhzR in response to cell density. J. Bacteriol. 176:3966-3974.

231. Price-Whelan, A., L. E. P. Dietrich, and D. K. Newman. 2006. Rethinking "secondary" metabolism: physiological roles for phenazine antibiotics. Nat. Chem. Biol. 2:71-78.

232. Rabaey, K., N. Boon, M. Hofte, and W. Verstraete. 2005. Microbial phenazine production enhances electron transfer in biofuel cells. Environ. Sci. Technol. 39:3401-3408.

233. Rahme, L. G., E. J. Stevens, S. F. Wolfort, J. Shao, R. G. Tompkins, and F. M. Ausubel. 1995. Common virulence factors for bacterial pathogenicity in plants and animals. Science 268:1899-1902.

234. Ran, H., D. J. Hassett, and G. W. Lau. 2003. Human targets of *Pseudomonas aeruginosa* pyocyanin. Proc. Natl. Acad. Sci. U.S.A 100:14315-14320.

235. Reszka, K. J., Y. O'Malley, M. L. McCormick, G. M. Denning, and B. E. Britigan. 2004. Oxidation of pyocyanin, a cytotoxic product from *Pseudomonas aeruginosa*, by microperoxidase 11 and hydrogen peroxide. Free Radical Biol. Med. 36:1448-1459.

236. Ruby, E. G., and K. H. Nealson. 1977. Pyruvate production and excretion by the luminous marine bacteria. Appl. Environ. Microbiol. 34:164-169.

237. San, K. Y., G. N. Bennett, S. J. Berrios-Rivera, R. V. Vadali, Y. T. Yang, E. Horton, F. B. Rudolph, B. Sariyar, and K. Blackwood. 2002. Metabolic engineering through cofactor manipulation and its effects on metabolic flux redistribution in *Escherichia coli*. Metab. Eng. 4:182-192.

238. Schreiber, K., N. Boes, M. Eschbach, L. Jaensch, J. Wehland, T. Bjarnsholt, M. Givskov, M. Hentzer, and M. Schobert. 2006. Anaerobic survival of *Pseudomonas aeruginosa* by pyruvate fermentation requires an Usp-type stress protein. J. Bacteriol. 188:659-668.

239. Singh, P. K., A. L. Schaefer, M. R. Parsek, T. O. Moninger, M. J. Welsh, and E. P. Greenberg. 2000. Quorum-sensing signals indicate that cystic fibrosis lungs are infected with bacterial biofilms. Nature 407:762-764.

240. Stams, A. J. M., F. A. M. de Bok, C. M. Plugge, M. H. A. van Eekert, J. Dolfing, and G. Schraa. 2006. Exocellular electron transfer in anaerobic microbial communities. Environ. Microbiol. 8:371-382.

241. Stewart-Tull, D. E. S., and A. V. Armstrong. 1971. The effect of 1-hydroxyphenazine and pyocyanin from *Pseudomonas aeruginosa* on mammalian cell respiration. J. Med. Microbiol. 5:67-73.

242. Sweet, W. J., and J. A. Peterson. 1978. Changes in cytochrome content and electron transport patterns in *Pseudomonas putida* as a function of growth phase. J. Bacteriol. 133:217-224.

243. Tabatabaie, T., J. D. Potts, and R. A. Floyd. 1996. Reactive oxygen species-mediated inactivation of pyruvate dehydrogenase. Arch. Biochem. Biophys. 336:290-296.

244. Thauer, R. K., K. Jungermann, and K. Decker. 1977. Energy conservation in chemotrophic anaerobic bacteria. Bacteriol. Rev. 41:100-180.
245. Trutko, S. M. 1989. The physiological role of phenazine pigments synthesized by the bacteria *Pseudomonas aureofaciens*. Biochemistry—Moscow 54:1092-1098.
246. Trutko, S. M., A. D. Garagulya, E. A. Kiprianova, and V. K. Akimenko. 1989. Physiological role of pyocyanin synthesized by *Pseudomonas aeruginosa*. Microbiologya 57:957-964.
247. Webb, M. 1968. Pyruvate accumulation in growth-inhibited cultures of *Aerobacter aerogenes*. Biochem. J. 106: 375-380.
248. Whiteley, M., K. M. Lee, and E. P. Greenberg. 1999. Identification of genes controlled by quorum sensing in *Pseudomonas aeruginosa*. Proc. Natl. Acad. Sci. U.S.A 96:13904-13909.
249. Williams, D. R., J. J. Rowe, P. Romero, and R. G. Eagon. 1978. Denitrifying *Pseudomonas aeruginosa*: some parameters of growth and active transport. Appl. Environ. Microbiol. 36:257-263.
250. Williams, H. D., J. E. A. Zlosnik, and B. Ryall. 2007. Oxygen, cyanide and energy generation in the cystic fibrosis pathogen *Pseudomonas aeruginosa*. Adv. Microb. Physiol. 52:1-71.
251. Wilson, R., D. A. Sykes, D. Watson, A. Rutman, G. W. Taylor, and P. J. Cole. 1988. Measurement of *Pseudomonas aeruginosa* phenazine pigments in sputum and assessment of their contribution to sputum sol toxicity for respiratory epithelium. Infect. Immun. 56:2515-2517.
252. Wimpenny, J. W. T., and A. Firth. 1972. Levels of nicotinamide adenine dinucleotide and reduced nicotinamide adenine dinucleotide in facultative bacteria and the effect of oxygen. J. Bacteriol. 111:24-32.
253. Worlitzsch, D., R. Tarran, M. Ulrich, U. Schwab, A. Cekici, K. C. Meyer, P. Birrer, G. Bellon, J. Berger, T. Weiss, K. Botzenhart, J. R. Yankaskas, S. Rondell, R. C. Boucher, and G. Doring. 2002. Effects of reduced mucus oxygen concentration in airway *Pseudomonas* infections of cystic fibrosis patients. J. Clin. Invest. 109:317-325.
254. Xu, K. D., P. S. Stewart, F. Xia, C. T. Huang, and G. A. McFeters. 1998. Spatial physiological heterogeneity in *Pseudomonas aeruginosa* biofilm is determined by oxygen availability. Appl. Environ. Microbiol. 64:4035-4039.

The invention claimed is:

1. A combination of products for interfering with viability of phenazine-producing bacteria, the combination of products comprising:
one or more agents able to inactivate a phenazine and/or a phenazine related pathway in the phenazine-producing bacteria, and
one or more antibiotics and/or one or more antimicrobials, for simultaneous combined or sequential use in the method comprising reducing the amount of phenazine in the phenazine-producing bacteria to reduce survivability and/or antibiotic resistance of the bacteria in a medium,
wherein the one or more agents comprise phenazine degrading agents capable of degrading phenazine, and
wherein the phenazine degrading agents comprise one or more phenazine-degrading proteins from *Mycobacteria* or *Streptomyces*.

2. The combination product of claim 1, wherein the phenazine-producing bacteria is *Pseudomonas aeruginosa*.

3. The combination product of claim 1, wherein the degrading phenazine occurs exogenously or endogenously.

4. The combination product of claim 1, wherein the one or more agents further comprise agents capable of chemically modifying phenazines.

5. The combination product of claim 1, wherein the one or more agents further comprise agents inhibiting the synthesis of phenazine in the phenazine-producing bacteria.

6. The combination product of claim 5, wherein the agents inhibiting the synthesis of phenazine is capable of inactivating one or more phenazine biosynthesis genes.

7. The combination product of claim 6, wherein the one or more phenazine biosynthesis genes are selected from the group consisting of PhzA, PhzB, PhzC, PhzD, PhzE, PhzF, PhzF1, PhzF2, PhzG, PhzG1, PhzG2, PhzM, PhzH, and PhzS.

8. The combination product of claim 6, wherein the agents inhibiting the synthesis of phenazine comprise small interfering RNA capable of suppressing the expression of one or more proteins in one or more phenazine biosynthesis pathways.

9. The combination product of claim 1, wherein the phenazine degrading agents degrade phenazine-1-carboxylic acid (PCA).

10. The combination product of claim 1, wherein the phenazine is pyocyanin.

11. The combination product of claim 1, wherein the phenazine is phenazine-1-carboxylic acid (PCA).

12. The combination product of claim 1, wherein the one or more agents further comprise inhibitors capable of blocking one or more phenazine exporters of the phenazine-producing bacteria.

13. The combination product of claim 1, wherein the one or more antibiotics comprise tobramycin.

14. The combination product of claim 1, further comprising one or more chelating agents capable of subtracting from the medium Fe(II) alone or in combination with Fe(III).

15. The combination product of claim 14, wherein the one or more chelating agents comprise one or more Fe(II)-specific chelating agents and/or one or more Fe(III)-specific chelating agents.

16. The combination product of claim 14, wherein the one or more chelating agents are selected from the group consisting of hemoglobin, transferrin, lactoferrin, conalbumin, ferritin, deferoxamine, deferiprone, deferasirox, 2,2-dipyridyl, 1,10-phenanthroline, and 3-(2-Pyridyl)-5,6-diphenyl-1,2,4-triazine-p,p'-disulfonic acid monosodium salt hydrate.

17. The combination product of claim 14, wherein the one or more chelating agents are in an amount of about 10 to about 1000 µM.

\* \* \* \* \*

SEQUENCE LISTING

```
<160> NUMBER OF SEQ ID NOS: 8

<210> SEQ ID NO 1
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 1
ccaggcaaat tctgttttat cagaccgctt ctgcgttctg atagcgctgg aactcgccac    60

<210> SEQ ID NO 2
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 2
gcttcaggtg ctggtacagt gcctgagtca tttccagttc c                         41

<210> SEQ ID NO 3
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 3
ggaactggaa atgactcagg cactgtacca gcacctgaag c                         41

<210> SEQ ID NO 4
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 4
ggaattgtga gcggataaca atttcacaca ggaaacagct ctgaagccga tgttgaccac    60
```

```
<210> SEQ ID NO 5
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 5
ccaggcaaat tctgttttat cagaccgctt ctgcgttctg atctgatcct cgtgcagagc        60

<210> SEQ ID NO 6
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 6
ggtctgcacc tgcaagtgca gggcggtacg ggaatc                                  36

<210> SEQ ID NO 7
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 7
gattcccgta ccgccctgca cttgcaggtg cagacc                                  36

<210> SEQ ID NO 8
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 8
ggaattgtga gcggataaca atttcacaca ggaaacagct cgtcaggttg agacagaacg        60
```